United States Patent
Terpetschnig et al.

(10) Patent No.: US 8,642,014 B2
(45) Date of Patent: Feb. 4, 2014

(54) LUMINESCENT COMPOUNDS

(75) Inventors: Ewald A. Terpetschnig, Urbana, IL (US); Leonid D. Patsenker, Kh arkov (UA); Oleksii Klochko, Kharkov (UA); Yuliia Kudriavtseva, Kharkov (UA); Anatoliy L. Tatarets, Kh arkov (UA); Inna G. Yermolenko, Kharkov (UA); Yevgen A. Povrozin, Kharkov (UA)

(73) Assignee: SETA BioMedicals, LLC, Urbana, IL (US)

( * ) Notice: Subject to any disclaimer, the term of this patent is extended or adjusted under 35 U.S.C. 154(b) by 369 days.

(21) Appl. No.: 12/512,972

(22) Filed: Jul. 30, 2009

(65) Prior Publication Data

US 2010/0266507 A1  Oct. 21, 2010

Related U.S. Application Data

(63) Continuation-in-part of application No. PCT/US2008/001274, filed on Jan. 30, 2008.

(60) Provisional application No. 60/887,311, filed on Jan. 30, 2007, provisional application No. 61/209,136, filed on Mar. 3, 2009.

(51) Int. Cl.
*A61B 5/00* (2006.01)
*C07D 513/00* (2006.01)
*C07D 245/00* (2006.01)
*F21V 9/16* (2006.01)
*G01N 1/30* (2006.01)

(52) U.S. Cl.
USPC ......... 424/9.6; 540/455; 540/460; 250/459.1; 435/40.5

(58) Field of Classification Search
None
See application file for complete search history.

(56) References Cited

U.S. PATENT DOCUMENTS 6,538,129 B1* 3/2003 Terpetschnig et al. ....... 536/26.6
2005/0202565 A1* 9/2005 Terpetschnig et al. .......... 436/56

OTHER PUBLICATIONS

Arunkumar et al, Squaraine-Derived Rotaxanes: Sterically Protected Fluorescent Near-IR Dyes, J. Am. Chem. Soc., vol. 127, No. 10, pp. 3288-3289 (2005).*
Leigh et al, The Mechanism of Formation of Amide-Based Interlocked Compounds: Prediction of a New Rotaxane-Forming Motif, Chem. Eur. J., vol. 10, Issue 20, pp. 4960-4969 (2004).*

* cited by examiner

*Primary Examiner* — Frederick Krass
*Assistant Examiner* — Dennis J Parad
(74) *Attorney, Agent, or Firm* — DASCENZO Intellectual Property Law, P.C.

(57) ABSTRACT

Luminescent reporter compounds that are rotaxanes having the structure

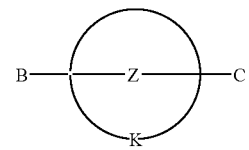

where B—Z—C is a reporter molecule based on a cyanine, squaric acid, or other reporter, and K is a macrocycle that encircles and interlocks with the reporter molecule. Applications of the reporter compounds are provided, as well as reactive intermediates used to synthesize the reporter compounds, and methods of synthesizing the reporter compounds.

41 Claims, 7 Drawing Sheets

US 8,642,014 B2

LUMINESCENT COMPOUNDS

CROSS-REFERENCES TO RELATED MATERIALS

The present application is a continuation-in-part of International Application Serial No. PCT/US2008/001274, filed Jan. 30, 2008, which designated the United States of America and was published in English on Aug. 7, 2008 as Publication No. WO 2008/094637, which claims priority under 35 U.S.C. §119(e) of U.S. Provisional Patent Application Ser. No. 60/887,311, filed Jan. 30, 2007, each of which is hereby incorporated by reference.

The present application further claims the benefit under 35 U.S.C. §119(e) of U.S. Provisional Patent Application Ser. No. 61/209,136 filed on Mar. 3, 2009, hereby incorporated by reference.

This application incorporates by reference in their entirety for all purposes all patents, patent applications (published, pending, and/or abandoned), and other patent and nonpatent references cited anywhere in this application. The cross-referenced materials include, but are not limited to, the following documents: Richard P. Haugland, HANDBOOK OF FLUORESCENT PROBES AND RESEARCH CHEMICALS ($6^{th}$ ed. 1996); JOSEPH R. LAKOWICZ, PRINCIPLES OF FLUORESCENCE SPECTROSCOPY ($2^{nd}$ ed. 1999); RICHARD J. LEWIS, SR., HAWLEY'S CONDENSED CHEMICAL DICTIONARY ($12^{th}$ ed. 1993).

TECHNICAL FIELD

The invention relates to compounds based on cyanines, squaric acid, among others. More particularly, the invention relates to compounds based on cyanines, squaric acid, among others that are useful as dyes and luminescent reporters.

BACKGROUND

Colorimetric and/or luminescent compounds may offer researchers the opportunity to use color and light to analyze samples, investigate reactions, and perform assays, either qualitatively or quantitatively. Generally, brighter, more photostable reporters may permit faster, more sensitive, and more selective methods to be utilized in such research.

While a colorimetric compound absorbs light, and may be detected by that absorbance, a luminescent compound, or luminophore, is a compound that emits light. A luminescence method, in turn, is a method that involves detecting light emitted by a luminophore, and using properties of that light to understand properties of the luminophore and its environment. Luminescence methods may be based on chemiluminescence and/or photoluminescence, among others, and may be used in spectroscopy, microscopy, immunoassays, and hybridization assays, among others.

Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including extinction coefficient, excitation and emission spectrum, Stokes' shift, luminescence lifetime, and quantum yield. An extinction coefficient is a wavelength-dependent measure of the absorbing power of a luminophore. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. A luminescence lifetime is the average time that a luminophore spends in the excited state prior to returning to the ground state. A quantum yield is the ratio of the number of photons emitted to the number of photons absorbed by a luminophore.

Luminescence methods may be influenced by extinction coefficient, excitation and emission spectra, Stokes' shift, and quantum yield, among others, and may involve characterizing fluorescence intensity, fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Luminescence methods have several significant potential strengths. First, luminescence methods may be very sensitive, because modern detectors, such as photomultiplier tubes (PMTS) and charge-coupled devices (CODs), can detect very low levels of light. Second, luminescence methods may be very selective, because the luminescence signal may come almost exclusively from the luminophore.

Despite these potential strengths, luminescence methods may suffer from a number of shortcomings, at least some of which relate to the luminophore. For example, the luminophore may have an extinction coefficient and/or quantum yield that is too low to permit detection of an adequate amount of light. The luminophore also may have a Stokes' shift that is too small to permit detection of emission light without significant detection of excitation light. The luminophore also may have an excitation spectrum that does not permit it to be excited by wavelength-limited light sources, such as common lasers and arc lamps. The luminophore also may be unstable, so that it is readily bleached and rendered nonluminescent. The luminophore also may have an excitation and/or emission spectrum that overlaps with the well-known autoluminescence of biological and other samples; such autoluminescence is particularly significant at wavelengths below about 600 nm. The luminophore also may be expensive, especially if it is difficult to manufacture. The luminophore may be highly quenched when labeled to proteins or other biomolecules at higher dye-to-biomolecule ratios.

ABBREVIATIONS

Figure 1:
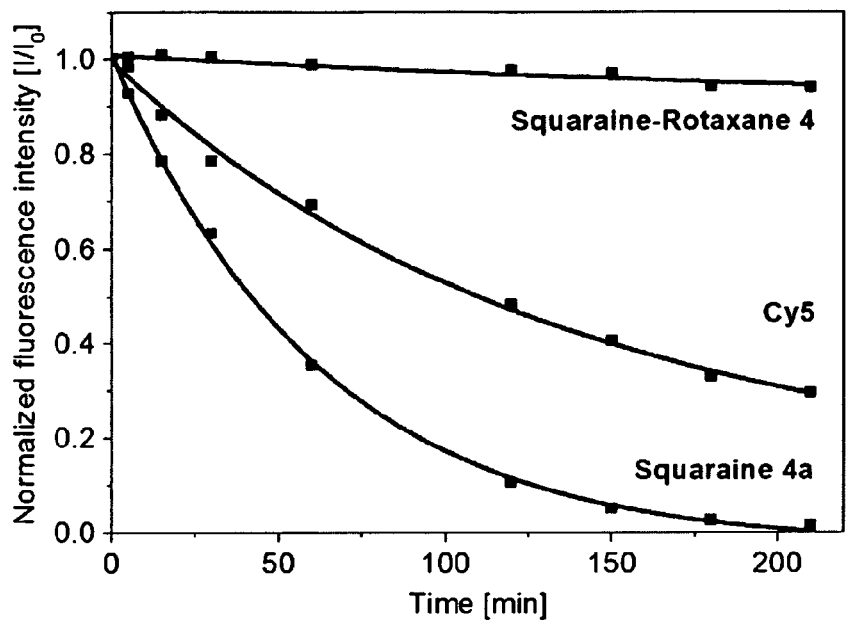
FIG. 1. A plot comparing the photostability (decrease of fluorescence intensity upon exposure to light of a 200 W Xenon lamp) of compounds 4 and 4a in water. Also shown is the relative photostability of the commercially available label Cy5.
Figure 2:
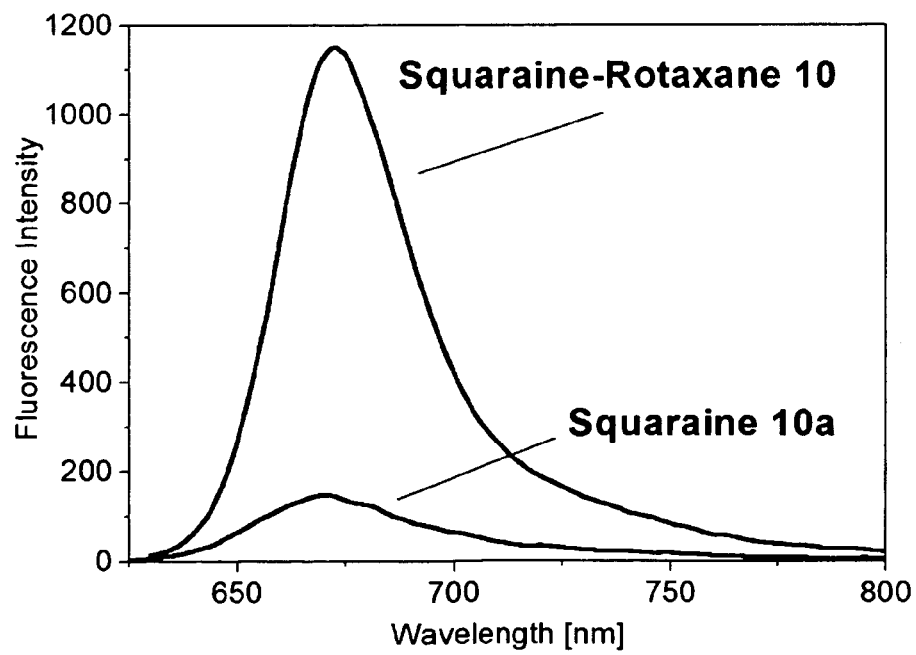
FIG. 2. A plot comparing the relative intensities of squaraine-rotaxane 10 and squaraine 10a in water.

The following abbreviations, among others, may be used in this application:

| Abbreviation | Definition |
| --- | --- |
| BSA | bovine serum albumin |
| Bu | butyl |
| DMF | dimethylformamide |
| D/P | dye-to-protein ratio |
| Et | ethyl |
| g | grams |
| h | hours |
| HSA | human serum albumin |
| L | liters |
| m | milli ($10^{-3}$) |
| M | molar |
| Me | methyl |
| mol | moles |
| M.P. | melting point |
| nm | nanometer ($10^{-9}$ meter) |
| NHS | N-hydroxysuccinimide |
| NIR | near infrared region |
| PBS | phosphate-buffered saline |
| Prop | propyl |
| TMS | tetramethylsilane |
| TSTU | N,N,N',N'-tetramethyl(succinimido)uronium tetrafluoroborate |
| μ | micro ($10^{-6}$) |

DESCRIPTION OF THE PREFERRED EMBODIMENTS

The invention relates generally to photoluminescent compounds and their synthetic precursors, and to methods of synthesizing and using such compounds. These photoluminescent compounds may be useful in both free and conjugated forms, as probes, labels, and/or indicators. This usefulness may reflect in part enhancement of one or more of the following: quantum yield, fluorescent lifetime, Stokes' shift, extinction coefficients, photostability and chemical stability. This usefulness also may reflect excitation and emission spectra in relatively inaccessible regions of the spectrum, including the red and near infrared.

More particularly, the invention provides rotaxane reporter compounds based on cyanines, squaric acid, among others, reactive intermediates used to synthesize the reporter compounds, and methods of synthesizing and using the reporter compounds, among others.

Rotaxanes are a class of mechanically-interlocked molecular complexes. In the case of rotaxanes, the complex includes an at least partially "dumbbell-shaped" molecule that is threaded through the central cavity of a macrocyclic molecule. Although there are typically no covalent bonds between the two components of the rotaxane, the two components remain interlocked, because the ends of the "dumbbell-shaped" molecule are larger than the internal diameter of the macrocycle cavity. Where the molecule threaded through the macrocycle is a luminescent reporter molecule, the presence of the macrocycle can confer enhanced stability on the reporter molecule.

The remaining discussion includes (1) an overview of structures, (2) an overview of synthetic methods, and (3) a description of the applications of the invention.

Overview of Structures

The reporter compounds relate generally to the following rotaxane structure:

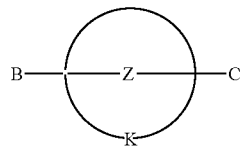

where B—Z—C is a reporter molecule and K is a macrocycle that encircles and interlocks with the reporter molecule.

The macrocycle K has the formula $K^1$, $K^2$, $K^3$, or K is a cyclodextrin, or is a macrocycle based on cucurbituryl or glycoluril, where $K^1$ is

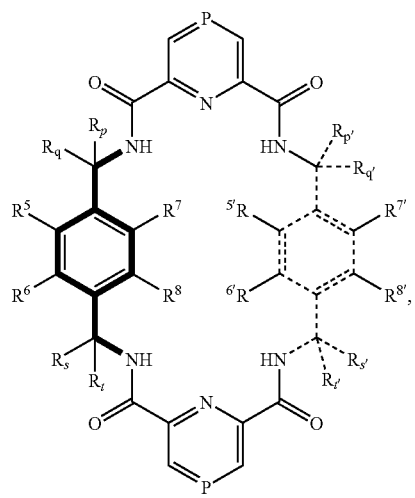

$K^2$ is

[structure of macrocycle with P-containing aromatic rings, amide linkages, and substituents $R_p$, $R_q$, $R_s$, $R_t$, $R_{p'}$, $R_{q'}$, $R_{s'}$, $R_{t'}$, $R^5$, $R^6$, $R^7$, $R^8$, $R^{5'}$, $R^{6'}$, $R^{7'}$, $R^{8'}$]

and
$K^3$ is

[structure of macrocycle with T-containing five-membered rings, amide linkages, and substituents $R_3$, $R_4$, $R_p$, $R_q$, $R_s$, $R_t$, $R_{p'}$, $R_{q'}$, $R_{s'}$, $R_{t'}$, $R^5$, $R^6$, $R^7$, $R^8$, $R^{5'}$, $R^{6'}$, $R^{7'}$, $R^{8'}$]

where $R^3$, $R^4$, $R^5$, $R^{5'}$, $R^6$, $R^{6'}$, $R^7$, $R^{7'}$, $R^8$ and $R^{8'}$ and $R_p$, $R_q$, $R_s$, $R_t$, $R_{p'}$, $R_{q'}$, $R_{s'}$, $R_{t'}$, are described in detail below.

T is O, S, N—H; L is a linker, $R^x$ is a reactive group; $S_c$ is a conjugated substance;

P is either $CR^3$, N, or $^+N$—$R^3$ or $^+O$;

$R^{\pm}$ is an ionic group;

Z is $$-\overset{R^\tau}{\underset{}{C}}=,$$

wherein B is $W^1$ and C is $W^2$ provided that Z is a single methine carbon residue ($-CR^\tau=$);

or Z is $$\overset{A}{\underset{D}{\overset{|}{\pi}}},$$

where $\pi$ is a four-membered aromatic ring and A, B, C and D are substituents of the four-membered ring;

wherein B and C are separated by one of substituents A or D, and wherein B is one of $W^2$, $W^4$, $W^6$, $W^8$, $W^{10}$, $W^{12}$, $W^{14}$, $W^{16}$ or $W^{18}$ and C is one of $W^1$, $W^3$, $W^5$, $W^7$, $W^9$, $W^{11}$, $W^{13}$, $W^{15}$ or $W^{17}$, in which case one of A or D is negatively charged; A and D are defined in detail below.

$W^1$, $W^2$, $W^3$, $W^4$, $W^5$, $W^6$, $W^7$, $W^8$, $W^9$, $W^{10}$, $W^{11}$, $W^{12}$, $W^{13}$, $W^{14}$, $W^{15}$, $W^{16}$, $W^{17}$ and $W^{18}$ have the formulae

[structures for $W^1$ through $W^7$ showing heterocyclic and aromatic cationic/substituted chromophore fragments with substituents $X^1$, $X^2$, $X^3$, $X^4$, Y, $R^1$, $CR^\alpha$, $CR^\beta$, $CR^\gamma$, $R^{10}$, $R^{10'}$, $R^{20}$, $R^{20'}$, $R^{21}$, $R^{21'}$, $R^{22}$, $R^{22'}$, $R^{23}$, $R^{23'}$, $R^{31}$, $R^{32}$, $R^{33}$, U]

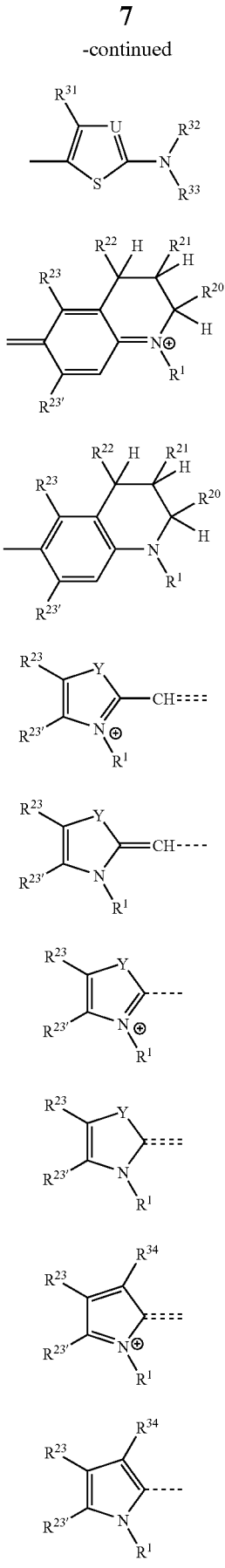

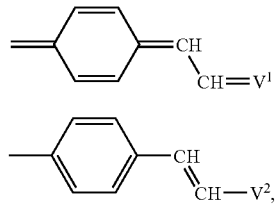

respectively.

The components $R^1$, $R^a$, $R^b$, $R^c$, $R^g$, $R^h$, $R^\alpha$, $R^\beta$, $R^\gamma$, $R^\tau$, $R^{20}$ to $R^{23}$, $R^{31}$, $R^{32}$, $R^{33}$, $R^{34}$, m, n, $X^1$, $X^2$, $X^3$, $X^4$, Y, U, $V^1$, $V^2$ and others are defined in detail in the Detailed Description. Alternatively, or in addition, the compound may include a reactive group and/or a carrier. Alternatively, or in addition, A, B, C, and D may be chosen so that the compound is photoluminescent.

The particular substituents on the substituted rings may be chosen quite broadly, and may include the various component listed above, among others. Selection of a particular combination of substituents may be used to fine-tune the spectral properties of the reporter compound, alter the hydrophilicity or hydrophobicity or the reporter compound, or otherwise tailor the properties of the reporter compound to a particular application.

The applications and methods relate generally to the synthesis and/or use of reporter compounds, especially those described above.

Reporter Compounds

Where the reporter compound is a colorimetric dye and/or a photoluminescent compound based on an aromatic center, B and C are typically chosen from $W^1$ and $W^2$, and B and C, are separated by A and D. In non-aromatic systems the following arrangement of substituents is possible:

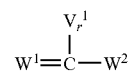

$V_r^1$ is selected from aliphatic, substituted aliphatic, reactive aliphatic groups among others.

Depending on the embodiment, A, B, C and D may be subject to additional limitations. In some embodiments, the compound also includes at least one of O, OR, S, Se, Te, N—$R^a$, C($R^b$)($R^c$). In other embodiments, at least one of $X^1$ through $X^4$ of $W^1$, $W^2$ or $W^3$ is or includes a heteroatom or a reactive linker. In yet other embodiments, the compound may include a reactive group and/or a carrier. The reporter compounds may be colorimetric dyes, useful as stains and for colorimetric detection. Alternatively or in addition, the reporter compounds may be photoluminescent, particularly fluorescent, and may have utility in photoluminescence assays and methods, as discussed above.

Important precursors for these rotaxanes are described in the experimental section.

Reactive Groups $R^x$

The substituents of Z may include one or more reactive groups, where a reactive group generally is a group capable of forming a covalent attachment with another molecule or substrate. Such other molecules or substrates may include proteins, carbohydrates, nucleic acids, and plastics, among others. Reactive groups vary in their specificity, and may preferentially react with particular functionalities and molecule types. Thus, reactive compounds generally include reactive groups chosen preferentially to react with functionalities found on the molecule or substrate with which the reactive compound is intended to react.

The compounds of the invention are optionally substituted, either directly or via a substituent, by one or more chemically reactive functional groups that may be useful for covalently attaching the compound to a desired substance. Each reactive group, or $R^x$, may be bound to the compound directly by a single covalent bond, or may be attached via a covalent spacer or linkage, L, and may be depicted as -L-$R^x$.

The reactive functional group of the invention $R^x$ may be selected from the following functionalities, among others: activated carboxylic esters, acyl azides, acyl halides, acyl halides, acyl nitriles, acyl nitriles, aldehydes, ketones, alkyl halides, alkyl sulfonates, anhydrides, aryl halides, aziridines, boronates, carboxylic acids, carbodiimides, diazoalkanes, epoxides, haloacetamides, halotriazines, imido esters, isocyanates, isothiocyanates, maleimides, phosphoramidites, silyl halides, sulfonate esters, and sulfonyl halides.

In particular, the following reactive functional groups, among others, are particularly useful for the preparation of labeled molecules or substances, and are therefore suitable reactive functional groups for the purposes of the reporter compounds:
a) N-hydroxysuccinimide esters, isothiocyanates, and sulfonylchlorides, which form stable covalent bonds with amines, including amines in proteins and amine-modified nucleic acids;
b) Iodoacetamides and maleimides, which form covalent bonds with thiol-functions, as in proteins;
c) Carboxyl functions and various derivatives, including N-hydroxybenztriazole esters, thioesters, p-nitrophenyl esters, alkyl, alkenyl, alkynyl, and aromatic esters, and acyl imidazoles;
d) Alkylhalides, including iodoacetamides and chloroacetamides;
e) Hydroxyl groups, which can be converted into esters, ethers, and aldehydes and iodoacetamides;
f) Aldehydes and ketones and various derivatives, including hydrazones, oximes, and semicarbozones;
g) Isocyanates, which may react with amines;
h) Activated C=C double-bond-containing groups, which may react in a Diels-Alder reaction to form stable ring systems under mild conditions;
i) Thiol groups, which may form disulfide bonds and react with alkylhalides (such as iodoacetamide);
j) Alkenes, which can undergo a Michael addition with thiols, e.g., maleimide reactions with thiols;
k) Phosphoramidites, which can be used for direct labeling of nucleosides, nucleotides, and oligonucleotides, including primers on solid or semi-solid supports;
l) Primary amines that may be coupled to variety of groups including carboxyl, aldehydes, ketones, and acid chlorides, among others;
m) Boronic acid derivatives that may react with sugars;
n) Pyrylium moieties react with primary amines;
o) Haloplatinates form stable platinum complexes with amines, thiols and heterocycles; and
p) Aryl halides react with thiols and amines.

R Groups

The R moieties associated with the various substituents of Z may include any of a number of groups, as described above, including but not limited to alicyclic groups, aliphatic groups, aromatic groups, and heterocyclic rings, as well as substituted versions thereof.

Aliphatic groups may include groups of organic compounds characterized by straight- or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked and may contain one or more heteroatoms (such as polyethers and polyamines, among others).

As used herein, "alicyclic groups" include hydrocarbon substituents that incorporate closed rings. Alicyclic substituents may include rings in boat conformations, chair conformations, or resemble bird cages. Most alicyclic groups are derived from petroleum or coal tar, and many can be synthesized by various methods. Alicyclic groups may optionally include heteroalicyclic groups that include one or more heteroatoms, typically nitrogen, oxygen, or sulfur. These compounds have properties resembling those of aliphatics and should not be confused with aromatic compounds having the hexagonal benzene ring. Alicyclics may comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aromatic groups may include groups of unsaturated cyclic hydrocarbons containing one or more rings. A typical aromatic group is benzene, which has a 6-carbon ring formally containing three double bonds in a delocalized ring system. Aromatic groups may be highly reactive and chemically versatile. Most aromatics are derived from petroleum and coal tar. Heterocyclic rings include closed-ring structures, usually of either 5 or 6 members, in which one or more of the atoms in the ring is an element other than carbon, e.g., sulfur, nitrogen, etc. Examples include pyridine, pyrole, furan, thiophene, and purine. Some 5-membered heterocyclic compounds exhibit aromaticity, such as furans and thiophenes, among others, and are analogous to aromatic compounds in reactivity and properties.

Any substituent of the compounds of the invention, including any aliphatic, alicyclic, or aromatic group, may be further substituted one or more times by any of a variety of substituents, including without limitation, F, Cl, Br, I, carboxylic acid, sulfonic acid, CN, nitro, hydroxy, phosphate, phosphonate, sulfate, cyano, azido, amine, alkyl, alkoxy, trialkylammonium or aryl. Aliphatic residues can incorporate up to six heteroatoms selected from N, O, S. Alkyl substituents include hydrocarbon chains having 1-22 carbons, more typically having 1-6 carbons, sometimes called "lower alkyl".

As described in WO 2001/11370, sulfonamide groups such as —$(CH_2)_n$—$SO_2$—NH—$SO_2$—R, —$(CH_2)_n$—CONH—$SO_2$—R, —$(CH_2)_n$—$SO_2$—NH—CO—R, and —$(CH_2)_n$—$SO_2$NH—$SO_3$H, where R is aryl or alkyl and n=1-6, can be used to reduce the aggregation tendency and have positive effects on the photophysical properties of cyanines and related dyes, in particular when these functionalities are directly associated with the benzazole ring in position 1 (the nitrogen atom in the azole ring).

Where a substituent is further substituted by a functional group $R^\pm$ that is ionically charged, such as, for example, a carboxylic acid, sulfonic acid, phosphoric acid, phosphonate or a quaternary ammonium group, the ionic substituent $R^\pm$ may serve to increase the overall hydrophilic nature of the compound.

As used herein, functional groups such as "carboxylic acid," "sulfonic acid," and "phosphoric acid" include the free acid moiety as well as the corresponding metal salts of the acid moiety, and any of a variety of esters or amides of the acid moiety, including without limitation alkyl esters, aryl esters, and esters that are cleavable by intracellular esterase enzymes, such as alpha-acyloxyalkyl ester (for example acetoxymethyl esters, among others).

The compounds of the invention are optionally further substituted by a reactive functional group $R^x$, or a conjugated substance $S_c$, as described below.

The compounds of the invention may be depicted in structural descriptions as possessing an overall charge, it is to be understood that the compounds depicted include an appropriate counter ion or counter ions to balance the formal charge present on the compound. Further, the exchange of counter ions is well known in the art and readily accomplished by a variety of methods, including ion-exchange chromatography and selective precipitation, among others.

Carriers and Conjugated Substances $S_c$

The reporter compounds of the invention, including synthetic precursor compounds, may be covalently or noncovalently associated with one or more substances. Covalent association may occur through various mechanisms, including a reactive functional group as described above, and may involve a covalent linkage, L, separating the compound or precursor from the associated substance (which may therefore be referred to as -L-$S_c$).

The covalent linkage L binds the reactive group $R^x$, the conjugated substance $S_c$ or the ionic group $R^\pm$ to the dye molecule, either directly (L is a single bond) or with a combination of stable chemical bonds, that include single, double, triple or aromatic carbon-carbon bonds; carbon-sulfur bonds, carbon-nitrogen bonds, phosphorus-sulfur bonds, nitrogen-nitrogen bonds, nitrogen-oxygen or nitrogen-platinum bonds, or aromatic or heteroaromatic bonds; L includes ether, thioether, carboxamide, sulfonamide, urea, urethane or hydrazine moieties. Preferable L's include a combination of single carbon-carbon bonds and carboxamide or thioether bonds.

Where the substance is associated noncovalently, the association may occur through various mechanisms, including incorporation of the compound or precursor into or onto a solid or semisolid matrix, such as a bead or a surface, or by nonspecific interactions, such as hydrogen bonding, ionic bonding, or hydrophobic interactions (such as Van der Waals forces). The associated carrier may be selected from the group consisting of polypeptides, polynucleotides, carbohydrates, nucleic acids, nucleotide triphosphates, polysaccharides, haptens, RNAs, PNAs, beads, microplate well surfaces, metal surfaces, semiconductor and non-conducting surfaces, nano-particles, and other solid surfaces.

The associated or conjugated substance may be associated with or conjugated to more than one reporter compound, which may be the same or different. Generally, methods for the preparation of dye-conjugates of biological substances are well-known in the art. See, for example, Haugland, MOLECULAR PROBES HANDBOOK OF FLUORESCENT PROBES AND RESEARCH CHEMICALS, Sixth Edition (1996), which is hereby incorporated by reference. Typically, the association or conjugation of a chromophore or luminophore to a substance imparts the spectral properties of the chromophore or luminophore to that substance.

Useful substances for preparing conjugates according to the present invention include, but are not limited to, amino acids, peptides, proteins, nucleosides, nucleotides, nucleic acids, carbohydrates, haptens, lipids, ion-chelators, nonbiological polymers, cells, and cellular components. The substance to be conjugated may be protected on one or more functional groups in order to facilitate the conjugation, or to insure subsequent reactivity.

Where the substance is a peptide, the peptide may be a dipeptide or larger, and typically includes 5 to 36 amino acids. Where the conjugated substance is a protein, it may be for example, an enzyme, an antibody, lectin, protein A, protein G, hormones, or a phycobiliprotein. The conjugated substance may be a nucleic acid polymer, such as for example DNA oligonucleotides, RNA oligonucleotides (or hybrids thereof), or single-stranded, double-stranded, triple-stranded, or quadruple-stranded DNA, or single-stranded or double-stranded RNA.

Another class of carriers includes carbohydrates that are polysaccharides, such as dextran, heparin, glycogen, starch and cellulose.

Where the substance is an ion chelator, the resulting conjugate may be useful as an ion indicator (calcium, sodium, magnesium, zinc, potassium and other important metal ions) particularly where the optical properties of the reporter-conjugate are altered by binding a target ion. Preferred ion-complexing moieties are crown ethers (U.S. Pat. No. 5,405,957) and BAPTA chelators (U.S. Pat. No. 5,453,517).

Other important carriers may include nanoparticles such as carbon-nanotubes, nanowires, silicon nanoparticles, quantum dots, gold and silver nanoparticles and other nanomaterials.

The associated or conjugated substance may be a member of a specific binding pair, and therefore useful as a probe for the complementary member of that specific binding pair, each specific binding pair member having an area on the surface or in a cavity which specifically binds to and is complementary with a particular spatial and polar organization of the other. The conjugate of a specific binding pair member may be useful for detecting and optionally quantifying the presence of the complementary specific binding pair member in a sample, by methods that are well known in the art.

Representative specific binding pairs may include ligands and receptors, and may include but are not limited to the following pairs: antigen-antibody, biotin-avidin, biotin-streptavidin, IgG-protein A, IgG-protein G, carbohydrate-lectin, enzyme-enzyme substrate; ion-ion-chelator, hormone-hormone receptor, protein-protein receptor, drug-drug receptor, DNA-antisense DNA, and RNA-antisense RNA.

Preferably, the associated or conjugated substance includes proteins, carbohydrates, nucleic acids, and nonbiological polymers such as plastics, metallic nanoparticles such as gold, silver and carbon nanostructures among others. Further carrier systems include cellular systems (animal cells, plant cells, bacteria). Reactive dyes can be used to label groups at the cell surface, in cell membranes, organelles, or the cytoplasm.

Finally these compounds can be linked to small molecules such as amino acids, vitamines, drugs, haptens, toxins, environmental pollutants.

Another important ligand is tyramine, where the conjugate is useful as a substrate for horseradish peroxidase. Additional embodiments are described in U.S. Patent Application Publication No. US 2002/0077487 A1, hereby incorporated by reference.

Synthesis a) Dye Components

The synthesis of the disclosed reporter compounds typically is achieved in a multi-step reaction, starting with the synthesis of a methylene base. The synthesis of suitable methylene bases can be achieved based on literature or novel methods. Generally, the spectral properties of the reporter compounds, including excitation and emission wavelengths for luminescent compounds, may be strongly dependent on the type of methylene base used. Typical starting materials include quarternized indolenines, benzthiazoles, benzoxazoles, benzimidazoles among others, and either squaric acid and its derivatives, or N,N'-diphenylformamidine or malonaldehyde bis(phenylimine)monohydrochloride.

For aniline-based squaraine dyes typical starting materials are various aniline-derivatives and squaric acid.

The dye molecules of this invention typically consist of a bridging unit and the heterocyclic bases $W^1$ and $W^2$, $W^3$ and $W^4$, $W^5$ and $W^6$, $W^7$ and $W^8$, $W^9$ and $W^{10}$, $W^{11}$ and $W^{12}$, $W^{13}$ and $W^{14}$, $W^{15}$, $W^{16}$, $W^{17}$ and $W^{18}$ or a combination thereof.

With regards to the aniline based dyes, the aniline-moiety may be directly connected to the squaraine center or like in $W^{17}$ and $W^{18}$ contain additional groups that help shifting the wavelength into the red region. When there is a bridging unit it is either a simple polymethine chain of various lengths or it can additionally contain an aromatic squaraine ring system. When the bridging unit is a polymethine chain the coupling agent can be N,N-diphenylformamidine, triethylorthoformate, or malonaldehyde bis(phenylimine) hydrochloride, 1,1,3-trimethoxypropane, 1,1,3,3-tetramethoxypropane and glutaconaldehyde dianil monohydrochloride.

Squaraine dyes are synthesized using squaric acid or one of its derivatives as starting materials and reacting them with a methylene base to form the dye.

The synthesis of starting materials and some of the most important precursors for the synthesis of cyanine and squaraine dyes are described in Example 1.

Squaric acid is a dibasic acid that undergoes a series of nucleophilic substitution reactions with various reagents, including amines, phenols, and CH-acidic compounds such as 1,2,3,3-tetramethyl-benzindole. The squaraine bridge in the resulting compounds stabilizes the conjugated chain and shifts the excitation and emission wavelength of these dyes as compared to cyanine-based dyes. The exchange of the oxygen in the squaraine moiety by an imino (=N—R), sulfur (=S), or a methylene (=CR$_2$) moiety was also shown to be a pathway to dyes with useful luminescent properties. The spectral properties of squaraine dyes are modified by thio-, imino- and methylene-derivatization of the squaraine bridge.

In general squaraine-based markers exhibit low to moderate quantum yields in water ($\phi$=0.05-0.3) and very high quantum yields (up to $\phi$=0.7) when covalently on non-covalently bound to biomolecules or in organic solvents. The absorption and emission wavelengths of the reporter compounds may be tuned by variation of the methylene base (e.g. indolenine vs. benzthiazole) and by an increase or decrease of the length of the conjugated carbon chain. Thus, the indolenine-squaraines absorb around 635 nm to 650 nm in water. The absorption and emission spectra of benzothiazolium and benzoselenazolium based dyes are shifted towards longer wavelengths. The emission maxima for benzothiazole based squaraine dyes in organic solvents are around 680 nm to 690 nm and can be found beyond 700 nm for benzoselenazole derivatives.

Benzoxazole and oxazole based squaraines absorb and emit even at shorter wavelengths than indolenine-based squaraines. The synthesis of benzoxazole-squaraines and other squaraines based on five-membered heterocyclic rings that absorb and emit between 500 and 600 nm is described in WO 2003/087052.

Importantly, the Stokes' shift in longer wavelength-emitting benzo-selenazolim and thiazolium dyes is larger, which helps to increase the sensitivity of a fluorescent measurement. Nevertheless, the photostability of these dyes are comparably lower as for the indolenine based dyes. Encapsulation by rotaxane-formation helps to improve on the photostabilities of squaraine dyes which is exemplified in FIG. 1.

Starting materials for the synthesis of squaraines are described in Example 1. The synthesis of cyanine dyes that include a cycloalkene-bridging element are described in U.S. Patent Application Publication No. US2004/0014981 A1 and by J. Flanagan et al. in Bioconjugate Chem. 8, 751-756 (1997), which are hereby incorporated by reference.

To enhance water-solubility, sulfonic acid or other groups such as including quaternary ammonium, polyether, carboxyl, and phosphate, among others, may be introduced into the heterocyclic ring systems. In order to facilitate covalent attachment to proteins, reactive N-hydroxy-succinimide ester (NHS ester) or other reactive derivatives may be synthesized.

The synthesis of cyanine dyes is described in Mujumdar et al., Bioconjugate Chem. 4(2) 105-111 (1993), and in several other patent applications (U.S. Patent Application Publication No. US2002/0077487 A1, U.S. Pat. No. 5,569,587, U.S. Pat. No. 5,672,027, U.S. Pat. No. 5,808,044, each incorporated by reference). The cyanine dyes incorporated in this invention may exhibit absorption maxima in the range between 500 and 850 nm. In addition to a variety of other structural parameters, the selection of a monomethine, trimethine, or pentamethine linkages permits the spectral properties of the resulting compound to be altered according to the characteristics desired. For example, where the remainder of the compound is held constant, shifting from a monomethine to a trimethine, to a pentamethine linkage in a $W^1$ or $W^2$ substituent typically results in a shift of the absorption and emission wavelengths of the resulting compounds to progressively longer wavelengths. The absorption maxima can be fine-tuned by additional introduction of functional groups to match the emission lines of a frequency-doubled Nd-Yag laser (532 nm), Kr-ion laser (568 and 647 nm), the HeNe laser (543 nm and 633 nm) and diode lasers (370 nm, 405 nm, 436 nm, 635 nm, 650 nm, 780 nm etc.). Unlike some squaraines, cyanine dyes exhibit a lesser tendency to change their quantum yields upon changing the environment (e.g. labelling to a protein).

Many compounds of the invention have an overall electronic charge. It is to be understood that when such electronic charges are present, that they are balanced by an appropriate counter-ion, which may or may not be identified.

b) Rotaxanes

The encapsulation procedures that are utilized to synthesize the rotaxanes of this invention depend on the type of the encapsulating species used: one way to synthesize these rotaxanes is using the templated amide macrocyclization chemistry developed by Leigh et al. [Angew. Chem. Int. Ed. 36(7), 728-732 (1997); Chem. Eur. J. 2004, 10, 4960-4969].

In this approach the dye component is dissolved in an inert solvent (depending on solubility of the compounds chloroform, or solvent mixtures might be used) and then titrated with equimolar amounts of diacid dichloride and xylylenediamine (e.g. 2,6 pyridinedicarbonyl dichloride or isophthaloyl dichloride and p-xylylenediamine) in presence of NEt$_3$ as base. Depending on the nature of the rotaxanes formed under these conditions they are purified either by reversed-phase or silica column chromatography. The reported synthetic yields are around 5 and 30%.

An encapsulation procedure for a non-reactive, aniline-type squaraine dye was reported by Arunkumar et al. in Chem. Eur. J. 2006, 12, 4684-4690.

Another way to produce water-soluble encapsulated dyes was described by Anderson at al. in Angew. Chem. Int. Ed. Engl. 1997, 36 (12), 1310-13. In this procedure the dye is synthesized in the presence of cyclodextrins (α-CD, β-CD) or a synthetic cyclophane macrocycle at 0-5° C. Paper chromatography was used to purified these compounds that were isolated in 12 and 15% yields. The hydrophobic effect was used to direct the synthesis of azo-dye rotaxanes with both CD and cyclophane macrocycles. In most solvents all of these rotaxanes were more soluble than the non-rotaxanated dyes and in addition they exhibited a lesser tendency to aggregate than their non-rotaxanated analogues. These dyes can also be encapsulated with macrocycles based on cucurbituryl or glycoluril.

There are several important factors that need to be considered when synthesizing novel Leigh-type aminde rotaxane, structures:

Aniline-based squaraines containing ortho-hydroxy groups do not form rotaxanes. This can most likely be attributed to sterical hindrance caused by the o-hydroxy groups of the aniline ring:

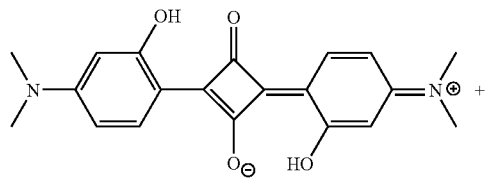

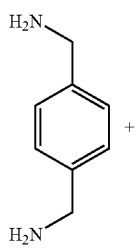

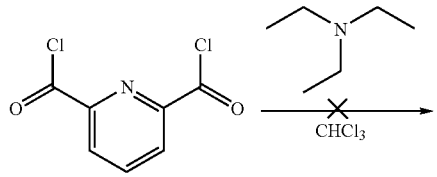

-continued

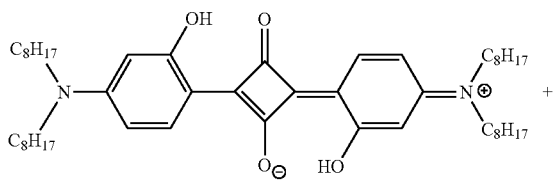

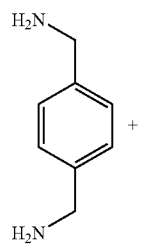

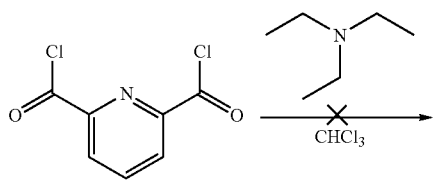

Also in the rotaxane-synthesis with indolenine-, benzthiazole-, and selenazole-type squaraine dyes sterical considerations need to be considered: Reactions of hydrophobic, indolenine-based squaraines containing either methyl or long-chain alkyl groups at the indolenine-nitrogen did not yield rotaxanes, which is evidence that sterical considerations indeed may play an important role.

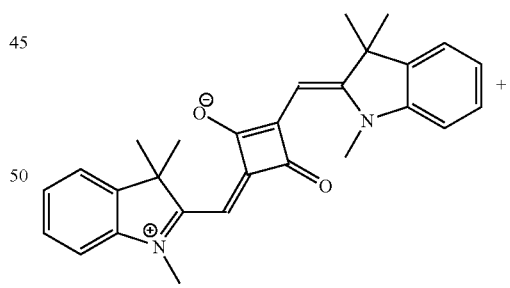

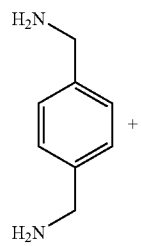

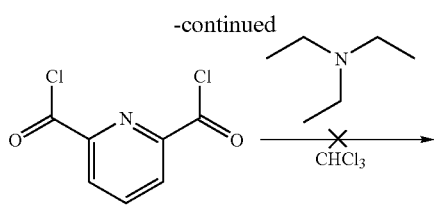

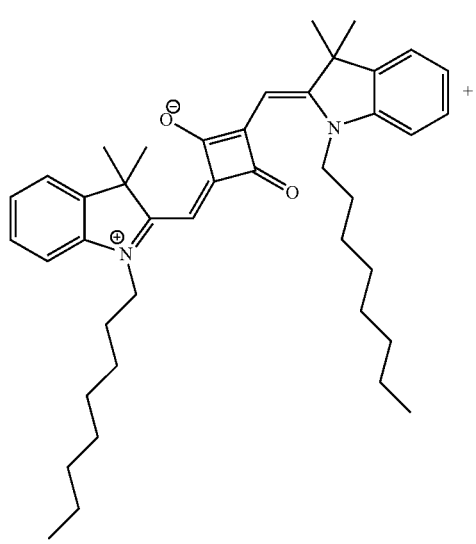

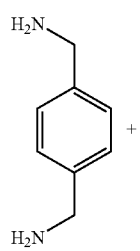

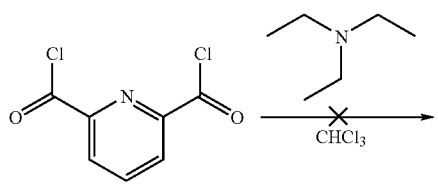

On the other hand, NH-substituted indolenines-, N-alkyl-benzothiazole- and N-alkyl-benzoselenazole-based squaraines form rotaxanes with very favorable spectral and photophysical properties (see below).

It is also understood that the building blocks in Leigh-type aminde rotaxanes are exchangeable and they can be substituted with a variety of substituents:

Dimethoxy-substituted versions of p-xylylenediamine, synthesized via reduction of 2,5-dicyano-hydrochinon-dimethylether with LiAlH$_4$ have been described by Schill et al. in Liebigs Ann. Chem. 1973, 2055. A nitro-derivative of p-xylylenediamine that can be reduced to a reactive amino-function after the rotaxane ring is synthesized was described by Lustig in Chem. Ber. 28, 2987 (1985).

The pyridine heterocycle of the dicarbonyl dichloride component in rotaxanes can be replaced with other heterocyclic components such as a thiophene, pyrrol or furan. 2,5-thiophene-dicarbonyl dichloride is commercially available from Aldrich. 3,4-dimethoxy-2,5-furandicarboxylic acid, the precursor for the synthesis of the acid chloride is also available from Aldrich and can be converted into the acid chloride by treatment with PCl$_5$ or acetyl chloride according to Klinkhardt, J. Prakt. Chem. (2), 25, 1882, 51 or Lewkowski, Pol. J. Chem. 75, 12, 1943-46 (2001). The 1H-pyrrole-2,5-dicarbonyl dichloride synthesis from dicarboxylic acid precursors which are available from Aldrich is described by Zielinski et al., Tetrahedron 61 (16), 4081-90 (2005). Starting materials like 3,4-Diethyl-1H-pyrrole-2,5-dicarboxylic acid (L164216), 3,4-Ethylenedioxypyrrole-2,5-dicarboxylic acid (637203), 4-Methyl-3-(2-nitroethyl)-2,5-pyrroledicarboxylic acid (S951072), 3,4-Bis(2,2,3,3,4,4,4-heptafluoro butyl)-1H-pyrrole-2,5-dicarboxylic acid (L165859) are available from Aldrich. Other precursors are described in Example 1.

Spectral and Photophysical Properties

The macrocyclic encapsulation procedure helps to improve on the aggregation tendencies and the quenching effect that causes a reduction in quantum yield in aqueous solution. In addition such encapsulation may yield luminescent compounds that have longer luminescent lifetimes in water as compared to conventional non-encapsulated dyes. Such encapsulation procedure could also help to improve in the properties of cyanine dyes in particular where such encapsulation prevents the occurrence of photo-induced isomerization reactions.

Dye compositions that are described in this invention can be encapsulated to yield luminescent compounds with improved properties for luminescence detection in for bioanalytical and imaging applications.

The novel dye compositions that are introduced herein are aimed at improving the shortcomings of cyanines, in particular squaraine dyes such as short lifetimes and low quantum yields in aqueous solution. The short lifetime and low quantum yields can mostly be attributed to quenching and aggregation of the dye molecules in aqueous solution. The novel structural features that are introduced in this invention might also help to reduce the self-aggregation and quenching tendencies of these labels. Further these dye compositions exhibit improved chemical and photochemical stability. Most importantly, the invention aims at producing luminescent bio- and protein-conjugates that are less prone to reducing their quantum yields at higher dye-to-protein ratios as is the case with many other luminescent labels, including squaraines. The effects of the encapsulation can be clearly demonstrated with compounds 10b and 12, where a Q.Y. increase of 8- and 20-fold, respectively, are observed.

The following examples should help to demonstrate the favorable properties that are obtained when squaraine dyes (both aniline and non-aniline type) are "rotaxanated":

The chemical structures of dyes 4a and the rotaxane 4 are shown below. Both, 4a and 4 contain the same symmetrical 5-sulfo-substituted squaraine dye but surprisingly have very different photophysical properties (see Table below):

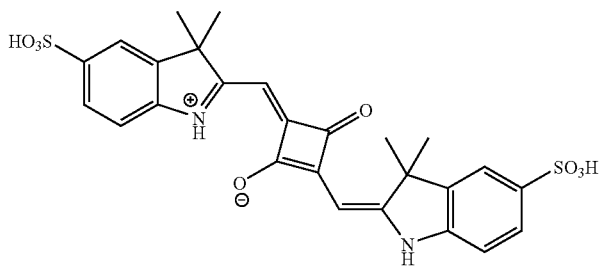 [SMILES: CC1(C)C(/C=C2/C(=O)C(/C=C3/Nc4ccc(S(=O)(=O)O)cc4C3(C)C)=C2[O-])=[NH+]c2ccc(S(=O)(=O)O)cc21]

4a

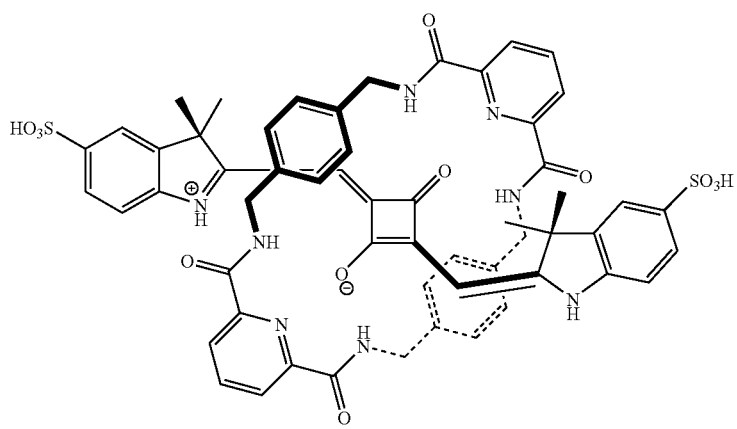

4

| Dye | λ_max (abs) | λ_max (em) | Solvent | Stokes' Shift Δλ | Photo-stability $t_{1/2}$ [min] | Quantum Yield [%] | Lifetime [ns] |
|---|---|---|---|---|---|---|---|
| 4a | 637 | 654 | water | 17 | ~40 | 26 | 1.56 |
| 4 | 640 | 656 | water | 16 | ~2000 | 40 | 2.4 |

While the absorption, emission wavelengths and Stokes' shifts of squaraine dye 4a and squaraine-rotaxane 4 are similar, squaraine 4a exhibits a mean fluorescence lifetime of 3.3 ns in water, while the lifetime of rotaxane 4 is in the order of 4.4 ns. Moreover, the rotaxane 4 has an approximately 50% higher quantum yield in water as compound to 4a. The quantum yield of 40% that was determined for the rotaxane-dye 4 in water represents an extremely high value, and is even higher than the quantum yield for one of the brightest commercially available cyanine dyes (Alexa Fluor 647) which is reported to be 33% in aqueous solution. The squaraine-rotaxane also has a substantially higher photostability as can be seen from FIG. 1 and the reported half-lifetimes ($t_{1/2}$) of these compounds upon exposure to light.

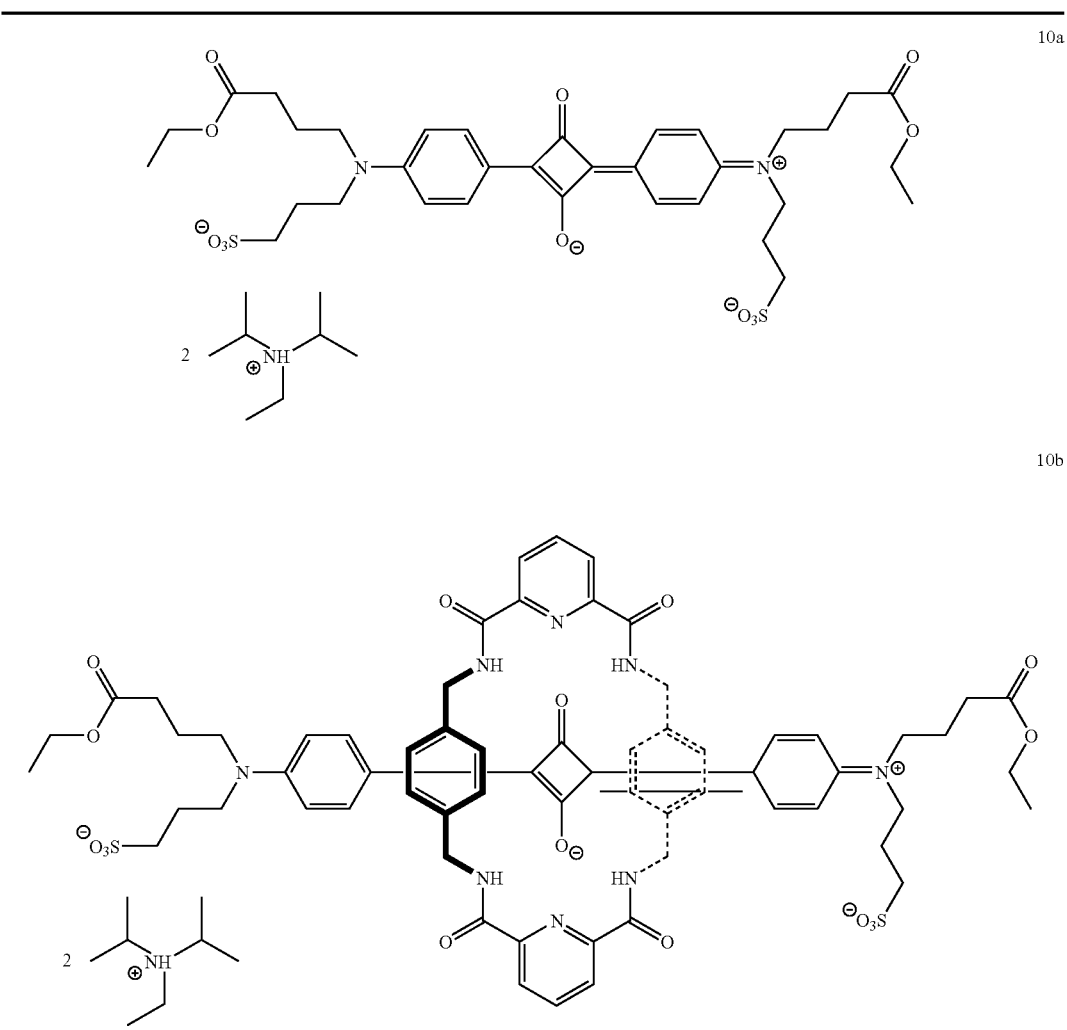

| Dye | $\lambda_{max}$ (abs) | $\lambda_{max}$ (em) | Solvent | Stokes' Shift $\Delta\lambda$ | Photo-stability $t_{1/2}$ [min] | Quantum Yield [%] | Lifetime [ns] |
|---|---|---|---|---|---|---|---|
| 10a | 644 | 670 | water | 26 | 80 | 3 | 0.05 |
| 10b | 655 | 673 | water | 18 | >2000 | 25 | 0.90 |
| 10-IgG | 657 | 675 | PB 7.4 | 18 | >2000 | 31 | 1.83 |

Figure 3:
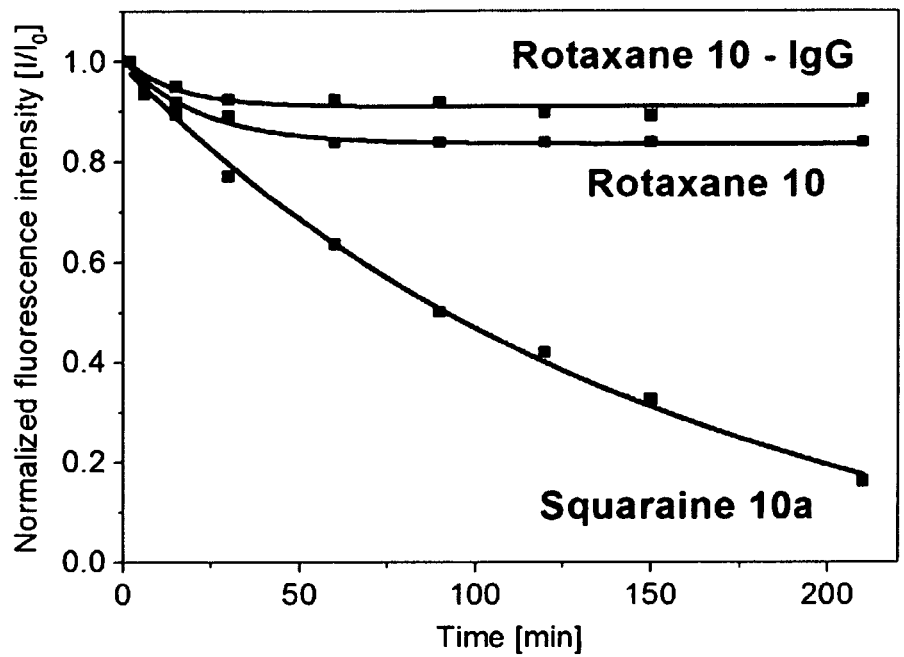
FIG. 3. A plot comparing the photostability (decrease of fluorescence intensity upon exposure to light of a 200 W Xenon lamp) of rotaxane 10, squaraine 10a and rotaxane conjugate 10-IgG in aqueous buffer.

A similar behaviour is also exhibited by aniline-based squaraines. Rotaxane-formation leads to a bathochromic shift of the absorption and emission maxima in rotaxane 10b as compared to the free squaraine dyes 10a. Upon rotaxination the aniline-squaraine 10a shows a dramatic increase in quantum yield from 3% to 25% in water, which is accompanied by a lifetime change from 1.5 to 2.3 ns. Importantly also the photostability of aniline-type squaraines increases substantially upon rotaxination (FIG. 3).

The photophysical, spectral and chemical properties of rotaxanes are also strongly dependent on the type of rotaxane: As compared to basic benzene-type bridging units as shown in rotaxane 10b, anthracene-based bridging units as shown in 12 seem to protect provide better protection of the squaraine dye in aqueous solution, which is evidenced by the remarkable increase in quantum yield of 12 as compared to 10b:

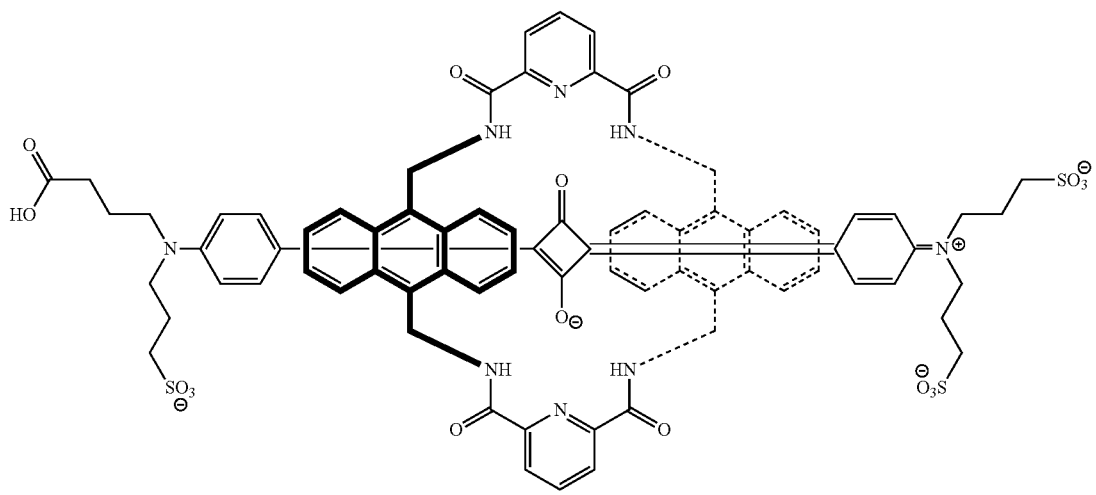

12

| Dye | $\lambda_{max}$ (abs) | $\lambda_{max}$ (em) | Solvent | Stokes' Shift $\Delta\lambda$ | Photo-stability $t_{1/2}$ [min] | Quantum Yield [%] | Lifetime [ns] |
| --- | --- | --- | --- | --- | --- | --- | --- |
| 10a | 644 | 670 | water | 26 | 80 | 3 | 0.05 |
| 12 | 665 | 716 | water | 51 | >2000 | 61 | 3.1 |
| 12-IgG | 664 | 709 | buffer | 45 | >2000 | 38 | 3.3 |

The photophysical properties of these rotaxanes even though they are compositions of 2 separate molecules appear to be as if they were coming from one molecule: e.g. the anthracene based molecules have a second small absorption band in the range between 300-400 nm stemming from the anthracene moiety. If excited at this wavelength no emission from the anthracene moiety but only emission from the squaraine dye is observed, which indicates that the energy transfer efficiency between the anthracene and the squaraine unit is very high. It is also understood that by changing the diamine moiety in the ring system one can generate rotaxanes that absorb at various wavelengths by still keeping the same emission wavelength of the encapsulated squaraine moiety. Thereby fluorophores with different excitation but the same emission maxima can be designed and synthesized.

Durene-based rotaxanes as described in Example 14 show extremely high extinction coefficients in the order of 370,000 [$M^{-1} \cdot cm^{-1}$], including extremely high quantum yields in water as compared to the parent unrotaxaneted squaraine dye. The fluorescence lifetime was measured to be 3.1 ns in water, a 6100% increase over the 50 ps lifetime of the parent squaraine dye.

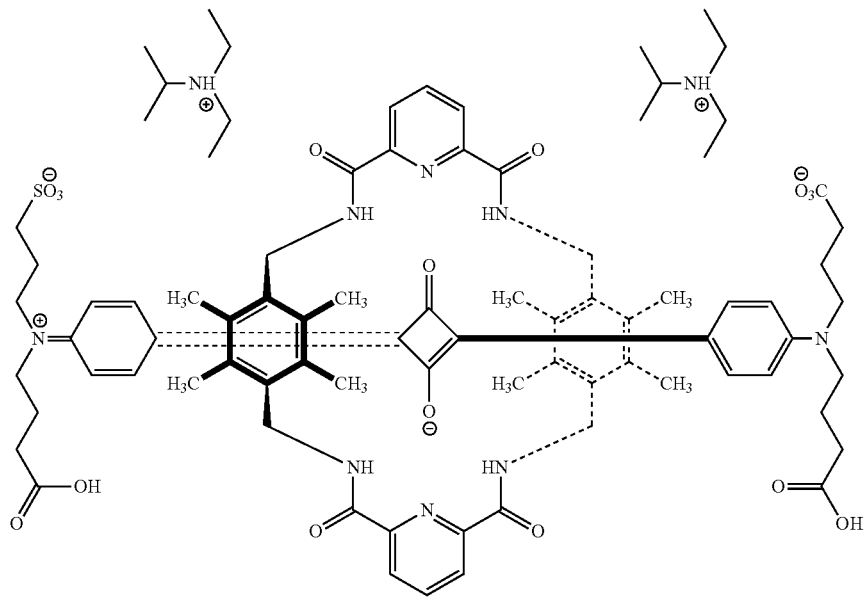

15

| Dye | $\lambda_{max}$ (abs) | $\epsilon$ | $\lambda_{max}$ (em) | Solvent | Stokes' Shift $\Delta\lambda$ | Photo-stability $t_{1/2}$ [min] | Quantum Yield [%] | Lifetime [ns] |
|---|---|---|---|---|---|---|---|---|
| 10a | 644 | 200,000 | 670 | water | 26 | 80 | 3 | 0.05 |
| 15 | 650 | 368,000 | 694 | water | 44 | >2000 | 60 | 3.1 |

It is understood that the benzene ring in p-xylenediamine can be replaced by a variety of other ring-systems such as anthracene, naphthalene, ring substituted aromatic and heterocyclic ring systems that will have an impact on the spectral as well as photophysical and chemical properties of these rotaxanes. Moreover, this outer ring-system could be a part of an aromatic or heterocyclic ring system that is a sensor molecule itself and that changes its properties with the analyte concentration thereby changing/influencing the photophysical properties of the core squaraine system. Importantly the extremely small band width at half max (30-40 nm) of the emission spectrum that was observed for one of these rotaxanes (14) demonstrates the multiplexing potential of these dyes.

Increased brightness, chemical and photostability and increased Stokes' shifts are desirable features for fluorescent labels because they both permit enhanced detection, and therefore allow more sensitive measurements. Both, aniline and non-aniline type squaraines show improved features upon encapsulation by a rotaxane structure. Finally, in order to make these rotaxanes cell-permeable while still keeping them water-soluble, ionic substituents such as sulfo and phosphate groups can be replaced with methyl- or ethyl-phosphonate groups which are neutral and therefore enable penetration of such compounds through the cell membrane while at the same time facilitating water-solubility.

Example 1

Synthesis of Precursors and Intermediates

This section describes the synthesis of various precursors and intermediates for the synthesis of novel cyanine dyes. p-hydrazinobenzenesulfonic acid (Illy et al., J. Org. Chem. 33, 4283-4285 (1968)), 2,3,3-trimethylindole-5-sulfonic acid potassium salt (1a), 1-(5-carboxypentyl)-2,3,3-trimethyl-3H-5-indoliumsulfonate (1b), 1-(4-sulfonatobutyl)-2,3,3-trimethylindoleninium-5-sulfonate (1h) (Mujumdar et al., Bioconjugate Chem. 4(2), 105-111 (1993)), and 1,2,3,3-tetramethylindoleninium-5-sulfonate (1c) were synthesized using literature procedures. 1d-1f are synthesized according to the procedures provided in U.S. Patent Application Publication No. US2002/0077487 A1. 1-(2-phosphonethyl)-2,3,3-trimethylindoleninium-5-sulfonate (1i) is described in PCT Patent Application Publication No. WO 2001/36973.

The synthesis of unsymmetrical squaraine dyes is described in S. Yagi et al., J. Chem. Soc., Perkin Trans. 1, 599-603 (2000). The synthesis of sulfonated benz-indolenines and other cyclo-condensed heterocycles is described in U.S. Patent Application Publication No. US 2002/0077487 A1 and U.S. Pat. No. 6,140,494 and by S. Mujumdar et al., Bioconjugate Chem. 7, 356-362 (1996).

It is also understood that the additional aromatic ring can be fused at different positions onto the parent heterocycle (see WO 2002/26891 A1) and Mujumdar et al., Bioconjugate Chem. 7, 356-362 (1996).

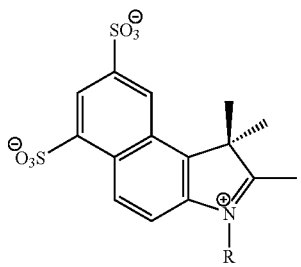

The synthesis of azolium compounds containing additional heteroatoms is also described in U.S. Patent Application Publication No. US2002/0077487 A1, hereby incorporated by reference.

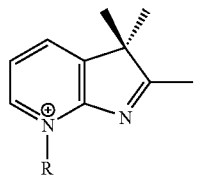

The synthesis of other fluorescent dyes and dye precursors is described in U.S. Patent Application Publication Nos. US2005/0202565, US2004/0166515 and US2002/0147354, each incorporated by reference. Other squaraines and precursors are described in U.S. Pat. No. 6,417,402. Starting materials for the synthesis of the rotaxane ring systems (2,6 pyridinedicarbonyl dichloride or isophthaloyl dichloride and p-xylylenediamine) including a variety of cyclodextrins including cucurbituryl and glycoluril are available from Aldrich. Additional precursors are described below.

Synthesis of 2,3,3-trimethylindole-5-sulfonic acid, potassium salt (1a)

Synthesis of p-Hydrazinobenzenesulfonic acid 33 g of sodium carbonate was added to a suspension of 104 g (0.6 mol) of p-aminobenzenesulfonic acid in 400 mL of hot water. The solution was cooled to 5° C. in an ice-bath, and 70 g of concentrated sulfuric acid were added slowly under rapid stirring. A solution of 42 g of sodium nitrite in 100 mL of water was then added under cooling. A light yellow diazo-compound precipitate formed, which was filtered and washed with water, but not dried.

The wet diazo-compound was added under stirring and cooling (5° C.) to a solution of 170 g of sodium sulfite in 500 mL of water. The solution, which turned orange, was stirred under cooling for 1 h, and then heated to reflux. Finally, 400 mL of concentrated hydrochloric acid were added. The solution turned yellow, and the product precipitated as a white solid. For complete decoloration, 1-2 g of powdered zinc were added. The reaction mixture was cooled overnight, and the precipitate was filtered, washed with water, and dried in an oven at 100° C.

Yield: 96 g (85%), white powder; M.P.=286° C. (Lit.=285° C.); $R_f$: 0.95 (RP-18, water:MeOH 2:1).

Synthesis of 2,3,3-trimethylindole-5-sulfonic acid 1a 18.2 g (0.12 mol) of p-hydrazinobenzenesulfonic acid and 14.8 g (0.17 mol) of isopropylmethylketone were stirred in 100 mL of glacial acetic acid at room temperature for 1 h. The mixture was then refluxed for 4 h. The mixture was cooled to room temperature, and the resulting pink solid precipitate was filtered and washed with ether.

The precipitate was dissolved in methanol, and a concentrated solution of potassium hydroxide in 2-propanol was added until a yellow solid completely precipitated. The precipitate was filtered, washed with ether, and dried in a desiccator over $P_2O_5$.

Yield: 20.4 g (71%), off-white powder; M.P.=275° C.; $R_f$: 0.40 (silica gel, isopropanol:water:ammonia=9:0.5:1).

1-(5-carboxypentyl)-2,3,3-trimethyl-3H-5-indolium-sulfonate (1b)

15.9 g (57 mmol) of 2,3,3-trimethylindolenium-5-sulfonic acid potassium salt 1a and 12.9 g (66 mmol) of 6-bromohexanoic acid were refluxed in 100 mL of 1,2-dichlorobenzene for 15 min under a nitrogen atmosphere. The solution was cooled to room temperature, and the resulting pink precipitate was filtered, washed with chloroform, and dried.

Yield: 15.8 g (58%), pink powder; $R_f$: 0.75 (RP-18, MeOH:water 2:1).

Synthesis of 1,2,3,3-tetramethylindolium-5-sulfonate (1c)

1.1 g of 2,3,3-trimethylindoleninium-5-sulfonate were suspended in 30 mL of methyl iodide. The reaction mixture was heated to boiling for 25 h in a sealed tube. After the mixture was cooled, excess methyl iodide was decanted, and the residue was suspended in 50 mL of acetone. The solution was filtered, and the residue was dried in a desiccator over $CaCl_2$. The resulting light yellow powder was used without further purification.

Yield: 90%, light yellow powder.

Synthesis of 3-(5-carboxypentyl)-2,3-dimethyl-5-sulfo-1-(3-sulfopropyl) indolium sodium salt (1d), (Scheme I)

A mixture of 25 g of ethyl 2-methylacetoacetate (I), 64 ml of 21% sodium ethoxide solution in ethanol and 34 mL of ethyl-6-bromohexanoate is refluxed in 200 mL of ethanol overnight. The mixture is filtered and the solvent is removed under reduced pressure. The residue is partitioned between 1 M HCl and chloroform.

The organic layer is dried over magnesium sulfate and purified on silica gel using 1:10 ethyl acetate/hexane as the eluent to yield 22 g of ethyl 2-(5-carboethoxypentyl)-2-methylacetoacetate (IIa).

The above compound is dissolved in 300 ml of methanol. A solution of 10 g NaOH in 100 mL water is added. The mixture is heated at 50° C. overnight. The solution is reduced to about 50 mL, acidified to pH 1 and extracted with ethyl acetate. The organic phase is collected, dried over $MgSO_4$ and evaporated to yield 13.5 g of 7-methyl-8-oxononanoic acid (IIIa).

The nonanonic acid is refluxed in 110 mL of acetic acid with 13.5 g of 4-hydrazinobenzenesulfonic acid for 4 hours. The acetic acid is evaporated and the product is purified on silica gel to yield 23 g of the product (IVa).

To the methanol solution of 11 g of Compound IVa is added 3.4 g of anhydrous sodium acetate. The mixture is stirred for five minutes. The solvent is evaporated and the resulting sodium salt is heated with 24.4 g of propane sultone at 110° C. for 1 hour to generate the final product 1d.

Synthesis of 3-(6-hydroxyhexyl)-2,3-dimethyl-5-sulfo-1-(3-sulfopropyl) indolium, sodium salt (1e)

Another starting material 1e is synthesized analogously using ethyl 2-methylacetoacetate and 6-benzoyl-1-bromo-hexane in the presence of 1.2 equivalents of sodium hydride in THF according to 1d. After isolating the 3-(6-hydroxy-hexyl)-2,3-dimethyl-5-sulfo-indolium, inner salt (the hydroxy group is again protected and the compound is quarternized using propanesultone. Deprotection is achieved using dilute NaOH.

1f is synthesized analogously taking into account the more polar nature of the sulfonic groups that are introduced either by reaction with 2-bromo-ethane-sulfonic acid, propane- or butanesultone. Sulfogroups can also be introduced by reaction of a 3-carboxy-alkyl-substituted compound like 1d with taurine according to Terpetschnig et al., Anal. Biochem. 217, 197-204 (1994).

Using 4-hydrazino-benzoic acid as described in Anal. Biochem. 217, 197-204 (1994) or 4-hydrazino-phenyl-acetic acid as described in Cytometry 11(3), 418-30 (1990) and reacting them in a Fischer indole synthesis with 7-methyl-8-oxononanonic acid or one of the other functionalized precursors as described above, 5-carboxy-derivatizated indoles that contain a spacer group in position 3 can be synthesized.

Other starting materials that contain functional groups in both $R_3$ and $R_4$ can be synthesized accordingly and used as starting materials for cyanine dyes of this invention. $R_3$ and $R_4$ can also be a part of an aliphatic ring system as described in U.S. Patent Application Publication No. US2002/0077487 A1.

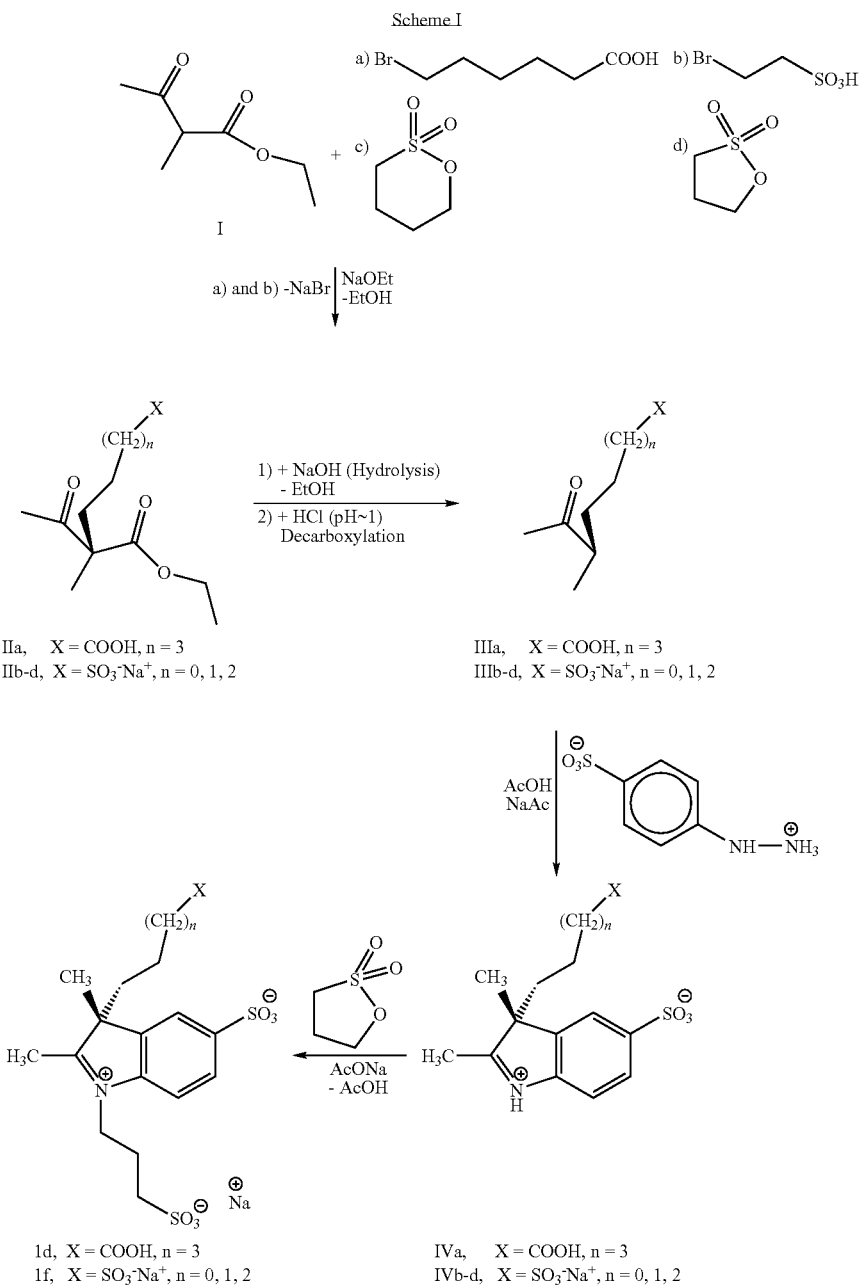

Selected indolenine-type precursors are summarized in the table below:

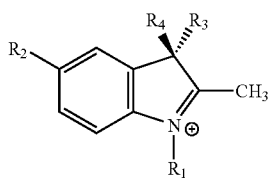

| 1 | $R_1$ | $R_2$ | $R_3$ (x = 2, 3, 4) | $R_4$ | (Patent) Literature |
|---|---|---|---|---|---|
| a | none | $SO_3^-$ | $CH_3$ | $CH_3$ | US2005/0202565 |
| b | $(CH_2)_5COOH$ | $SO_3K$ | $CH_3$ | $CH_3$ | US2004/0166515 |
| c | $CH_3$ | $SO_3^-$ | $CH_3$ | $CH_3$ | Bioconj. Chem. 4(2), 105, 1993 |
| d | $(CH_2)_3SO_3Na$ | $SO_3^-$ | $(CH_2)_5COOH$ | $CH_3$ | US2002/0077487 |
| e | $(CH_2)_3SO_3Na$ | $SO_3^-$ | $(CH_2)_6OH$ | $CH_3$ | US2002/0077487 |
| f | none or $(CH_2)_3SO_3^-$ | $SO_3^-$ | $(CH_2)_4SO_3Na$ | $CH_3$ | WO 2004/039894 |
| g | none or $(CH_2)_4SO_3^-$ | COOH | $CH_3$ | $CH_3$ | Anal. Biochem. 217, 197-204 (1994) |
| h | $(CH_2)_3SO_3Na$ | $SO_3^-$ | $CH_3$ | $CH_3$ | U.S. Pat. No. 6,140,494 |
| i | $(CH_2)_2PO(OH)_2$ | $SO_3^-$ | $CH_3$ | $CH_3$ | WO 2001/36973 |
| j | none | $CH_2$—COOH | $CH_3$ | $CH_3$ | U.S. Pat. No. 4,981,977 |

Synthesis of Aniline Precursors

Aniline-type squaraines and precursors are described in U.S. Pat. Nos. 5,101,015, 5,039,818, 5,416,214, 4,830,786 and 6,417,402 and U.S. Patent Application Publication No. US2002/0147354, and in references listed therein. Additional precursors and dyes are described in the Examples below. The synthesis of unsymmetrical squaraine dyes is described in S. Yagi et al., J. Chem. Soc., Perkin Trans. 1, 599-603 (2000).

Synthesis of a Disulfonated Aniline-Derivative

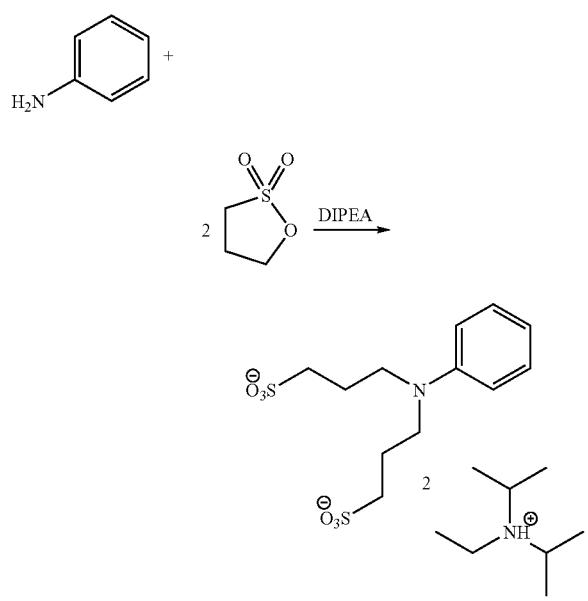

A mixture of aniline (7 mmol), N,N-diisopropylethylamine (DIPEA, 18 mmol) and propane sultone (16 mmol) was heated in a pressure tube in 10 mL of acetonitrile at 120-130° C. for 9 h under argon atmosphere. The solvent was evaporated and ethylacetate was added. The precipitated DIPEA bromide was filtered off and the filtrate was evaporated. The residue was treated with ether to give di[ethyl (diisopropyl)ammonium] 3-(3-sulfonatopropylanilino)-1-propanesulfonate as a white or pinky-white solid. Yield: 94%.

New Aniline-Precursors

Starting materials for the synthesis of novel aniline-type squaraine-rotaxanes dyes that are claimed in this application are described here. It should be also noted that the procedures for the synthesis of squaraines including the subsequent conversion to Leigh-type aminde-rotaxanes follows a standard protocol that sometimes require adjustments in regards to the solvent, temperature and/or the reaction time. Several of these procedures are described in the Experimental part below or in the cited literature references.

Synthesis of Sulfonated Benzylaniline-Intermediates

The synthesis of 4-(bromomethyl)benzenesulfonic acid for novel polysulfonated aniline-based rotaxanes from p-toluenesulfonyl chloride is achieved according to a procedure described by Yee et al., J. Med. Chem. 1990, 33, 2437-2451 and L. Blangey, et al., Helv. Chim. Acta, 1942, 25, 1162. Di-benzylated anilines are synthesized according to literature procedures (see above).

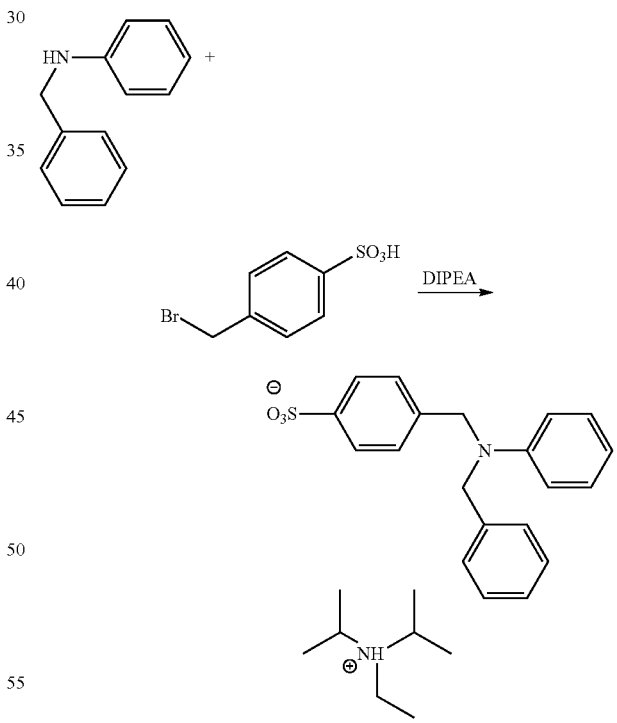

A mixture of the N-benzyl-aniline (1.0 mmol), 4-(bromomethyl)benzenesulfonic acid (1.2 mmol) and N,N-diisopropylethylamine (DIPEA, 2.2 mmol) was heated in 10 mL of acetonitrile at 120-130° C. for 9 h in a pressure tube under argon atmosphere. The solvent was removed under reduced pressure and ethyl acetate was added. The precipitated DIPEA bromide was filtered and the filtrate was evaporated. After drying, the raw product was used without further purification.

Synthesis of Thiophene-Intermediates

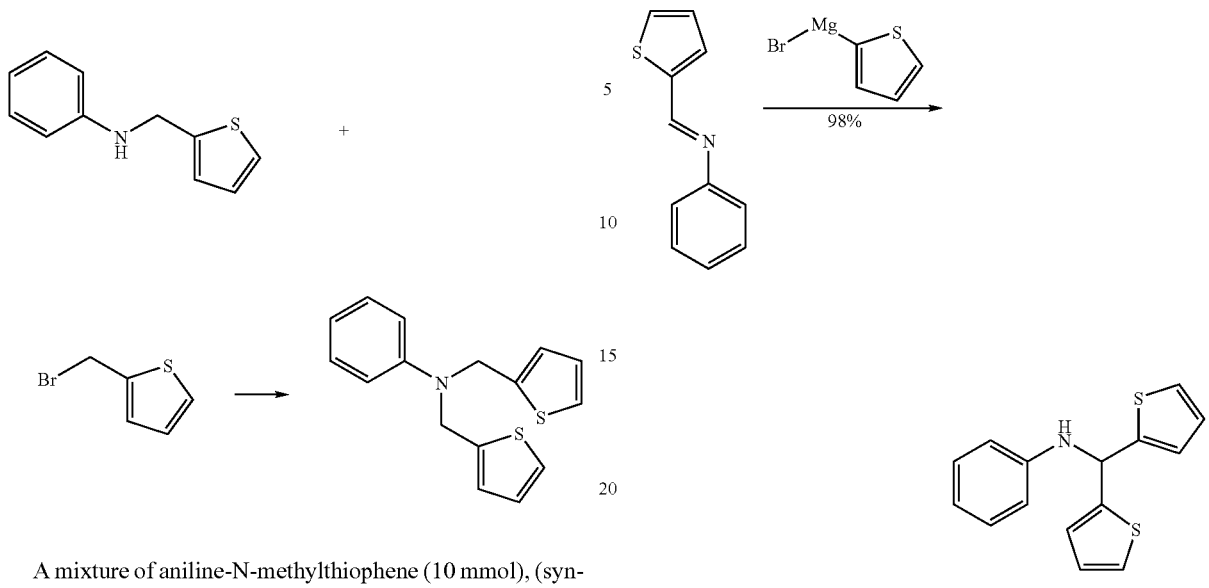

A mixture of aniline-N-methylthiophene (10 mmol), (synthesized 2-formyl-thiophene and aniline), 2-bromomethylthiophene (12 mmol) and N,N-diisopropylethylamine (DIPEA, 22 mmol) was heated in 10 mL of acetonitrile at 120-130° C. for 9 h in a pressure tube under argon atmosphere. The solvent was removed under reduced pressure and ethyl acetate was added. The precipitated DIPEA bromide was filtered and the filtrate was evaporated. After drying, the raw product was purified by flash chromatography on silica gel, eluent: hexane/triethylamine.

A mixture of 2-(2-thienylmethylanilinomethyl)thiophene (1.83 mmol) and squaric acid (0.92 mmol) was refluxed in a mixture of n-butanol (15 mL) and toluene (30 mL) for 12 h. After cooling, the solvent was removed on a rotary evaporator, and the residue was purified by column chromatography using silica gel (gradient 0-2% MeOH in CHCl3) to yield the relevant squaraine dye.

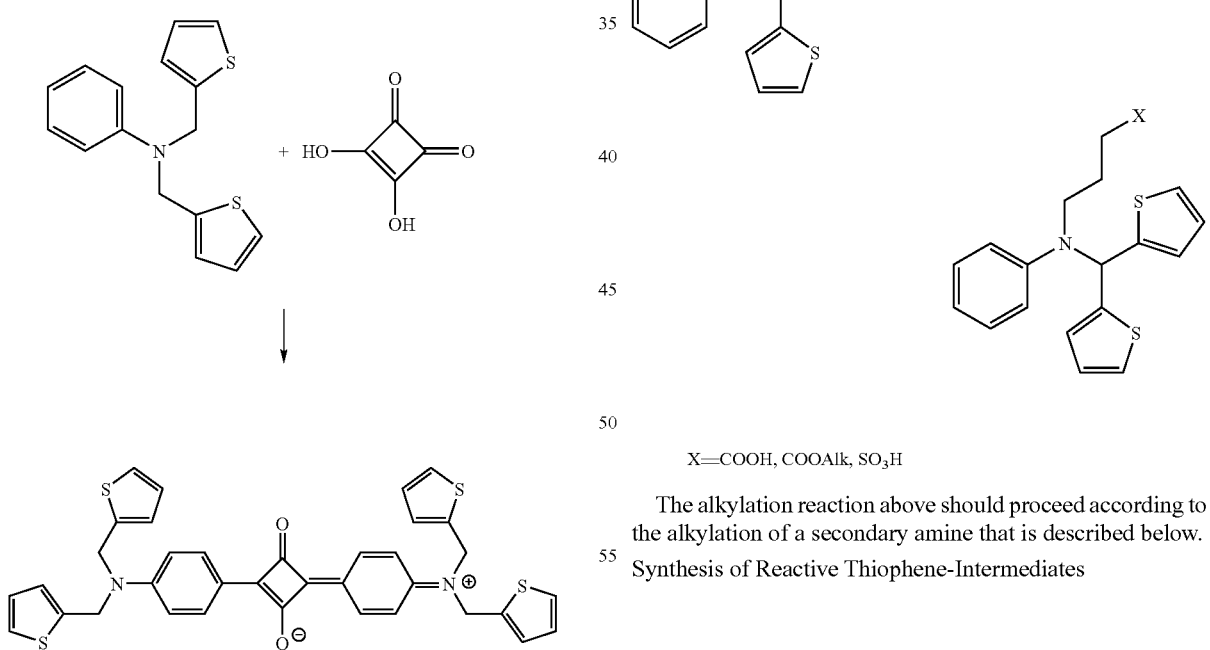

X=COOH, COOAlk, SO3H

The above reaction is described in J. Org. Chem. 1989, 54, 6120-6123. 2-thienyl-magnesium bromide can be replaced by any heterocycle-magnesium bromide.

The alkylation reaction above should proceed according to the alkylation of a secondary amine that is described below.

Synthesis of Reactive Thiophene-Intermediates

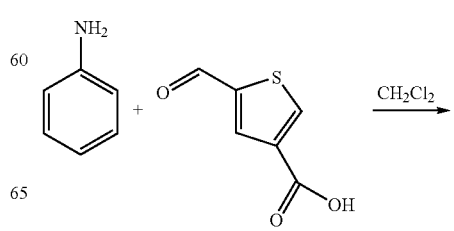

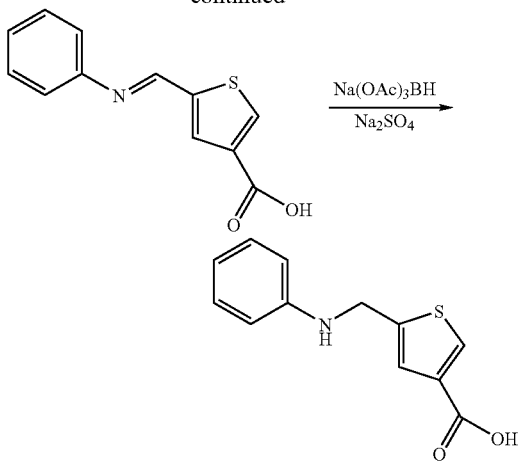

To a solution of aniline (0.24 mmol) in 1,2-dichloroethane (4 mL) were sequentially added 5-formyl-3-thiophenecarboxylic acid (0.045 g, 0.29 mmol) and sodium sulfate (150 mgs) under a nitrogen atmosphere at room temperature as described in J. Med. Chem. 49 (24), 6946 (2006). The contents were stirred at room temperature for twenty hours and sodium triacetoxyborohydride (0.075 g, 0.336 mmol) was added. The reaction was allowed to continue at room temperature for six hours and quenched by the addition of water (15 mL). Dichloromethane (15 mL) was added, and sulfurdioxide gas was bubbled through the reaction mixture for ten minutes and the contents transferred into a separating funnel. The organic layer was separated, washed with brine (2×20 mL), dried over sodium sulfate, concentrated under reduced pressure and purified by silica gel column chromatography using dichloromethane and MeOH to yield the title compound as a solid.

Synthesis of Novel N-Disubstituted Anilines

A mixture of aniline-N-methyl-thiophene (10 mmol), 1,3-propansultone or 4-(2-bromoethyl)-1-benzenesulfonic acid (12 mmol) and N,N-diisopropylethylamine (DIPEA, 12 mmol) was heated in 10-15 mL of acetonitrile in a pressure tube at 120-130° C. for 9 h under argon atmosphere. The solvent was removed under reduced pressure and crude product was purified by flash chromatography using silica gel.

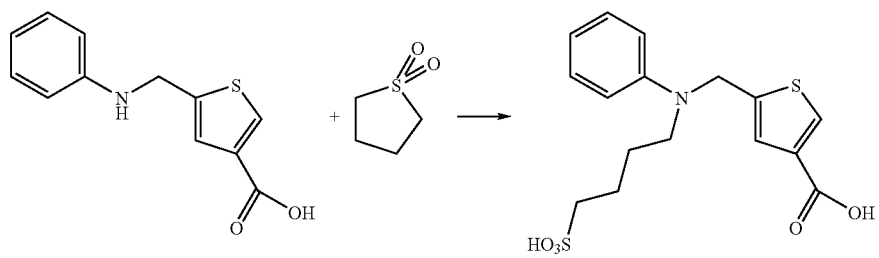

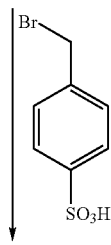

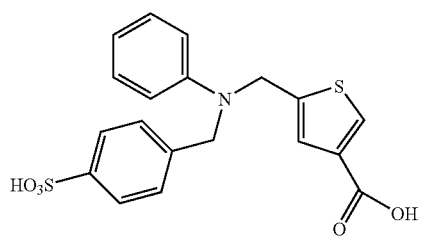

Synthesis of Anilino-Pyridine Precursors

The synthesis of 3-anilinomethylpyridine precursors should proceed similar to the synthesis of N-benzylaniline described in Example 7 except with nicotin-aldehyde as the reagent:

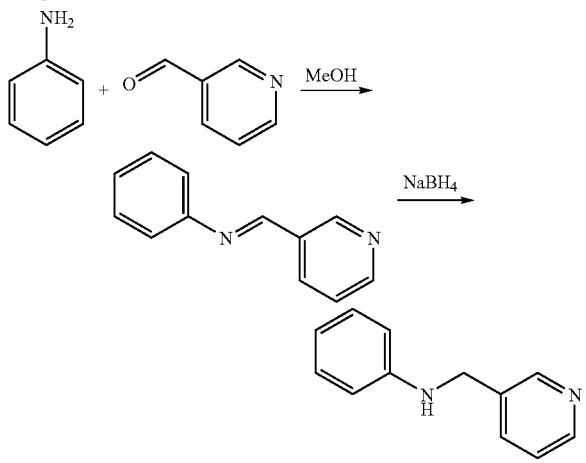

Synthesis of a Reactive Anilino-Pyridine Precursor

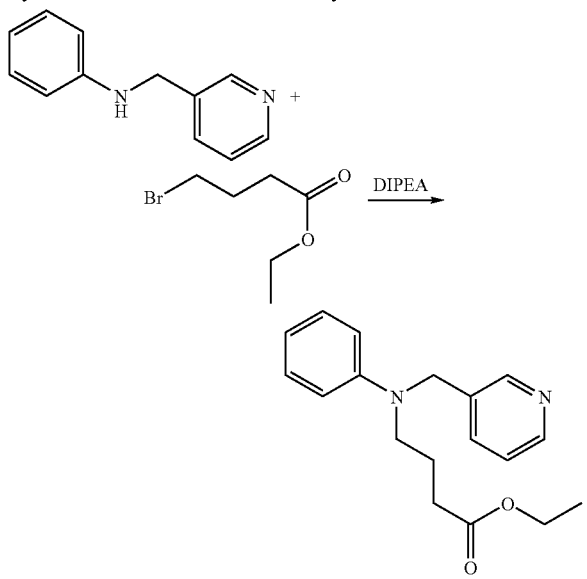

A mixture of 3-anilinomethylpyridine (12 mmol), ethyl 4-bromobutanoate (14.4 mmol) and N,N-diisopropylethylamine (DIPEA, 26 mmol) is heated in 15 mL of acetonitrile at 120-130° C. for 9 h in a pressure tube under argon atmosphere. The solvent was removed under reduced pressure and ethyl acetate was added. The precipitated DIPEA bromide was filtered and the filtrate was evaporated. After drying, the raw product was purified by flash chromatography on silica gel.

Julolidine-Based Squaraines

Julolidine is commercially available from Aldrich. A dihydroxy-substituted julolidine, 2,3,6,7-tetrahydro-1H,5H-benzo<ij>quinolizine-2,6-diol, was described Silhankova et al., Collect. Czech. Chem. Commun. 50(5) 1048-1056 (1985).

Thiophene-Type Squaraines

The synthesis of thiophene- and thiazole-heterocycle-containing squaraine dyes were described by D. Keil and H. Hartmann in Liebigs Ann. 1995, 979-984.

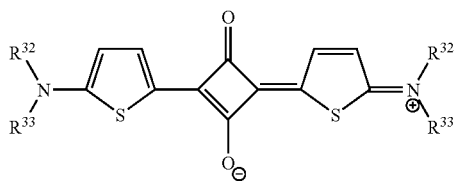

Long-Wavelength Squaraines

The synthesis of long-wavelength squaraine precursors including substituted squaric acid precursors are described in the dissertation of R. Petermann from the University of Mainz, Fachbereich Chemie und Pharmazie, with the title "Squaraine mit verlaengerter Konjugation", Mainz 2001. Water-soluble versions of these long-wavelength squaraine dyes can be synthesized according to procedures provided in there by introducing sulfa groups into the alkyl-amino groups, which is described below.

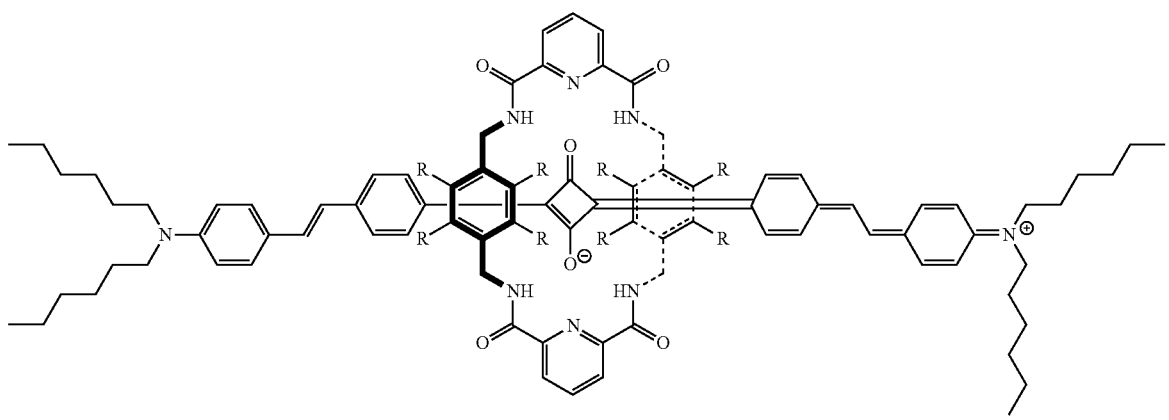

R = H, Me

Short-Wavelength Squaraines

The synthesis of squaraine dyes with 5-membered heterocycles showing absorption and emission in the shorter wavelength region are described in WO 2003/080752. Other short wavelength squaraine precursors are described by Treibs and Jacob, Liebigs Ann. Chem. 712, 123-137 (1968) and Treibs and Jocob, Angew. Chem. 77, 680 (1965). Water soluble versions of these dyes are obtained by introduction of ionic species into the heterocyclic system.

Synthesis of Unsymmetrical Squaraines

The general methods and procedures to synthesize unsymmetrical squaraines are described by S. Yagi et al., J. Chem. Soc., Perkin Trans. 1:599 (2000). Condensation of tertiary aromatic amine with squaric acid dichloride in methylene dichloride at room temperature results in a monosquaraine which, after hydrolysis, can be further condensed with a second tertiary aromatic amine under reflux in a butanol-toluene mixture to give the unsymmetrical squaraine (examples for a charged ionic hydrophilic and neutral hydrophilic compound are below):

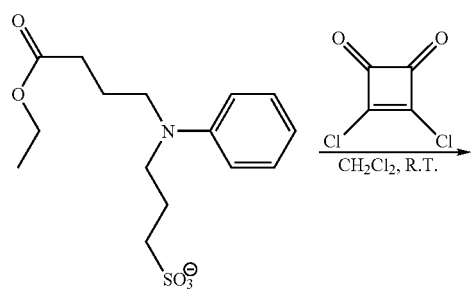

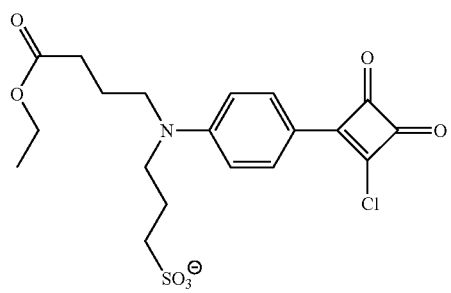

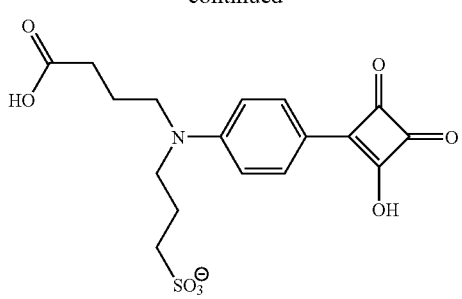

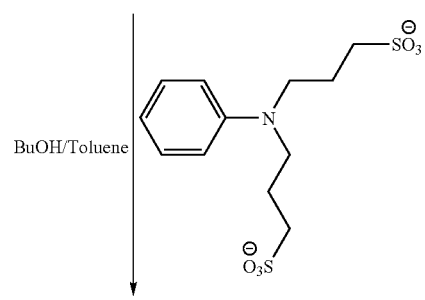

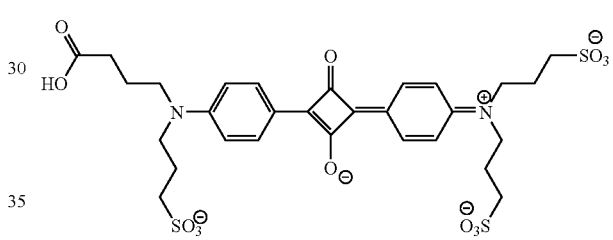

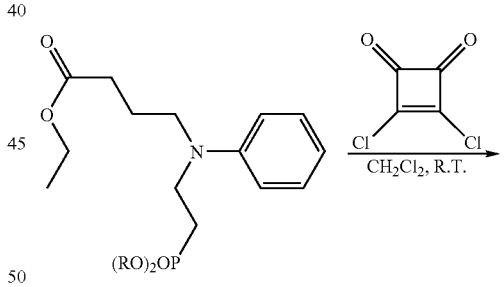

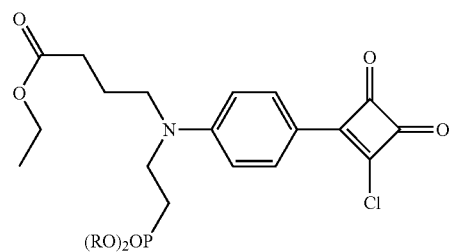

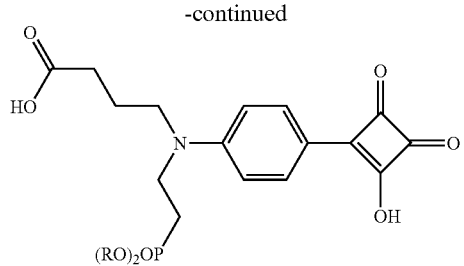
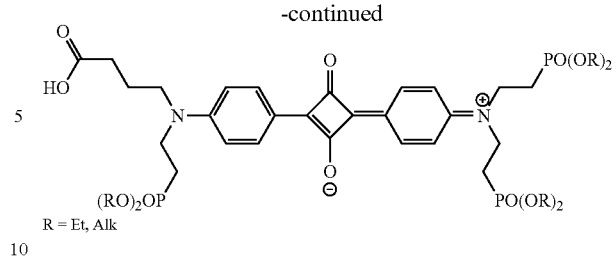
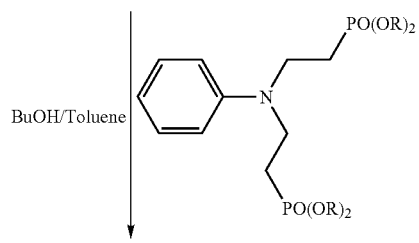
Another approach to synthesizing unsymmetrical squaraines is based on the reaction of squaric acid with both aniline-type ligands in a 1:1 ratio and purifying out the unsymmetrical dye from a mixture with two symmetrical dyes.
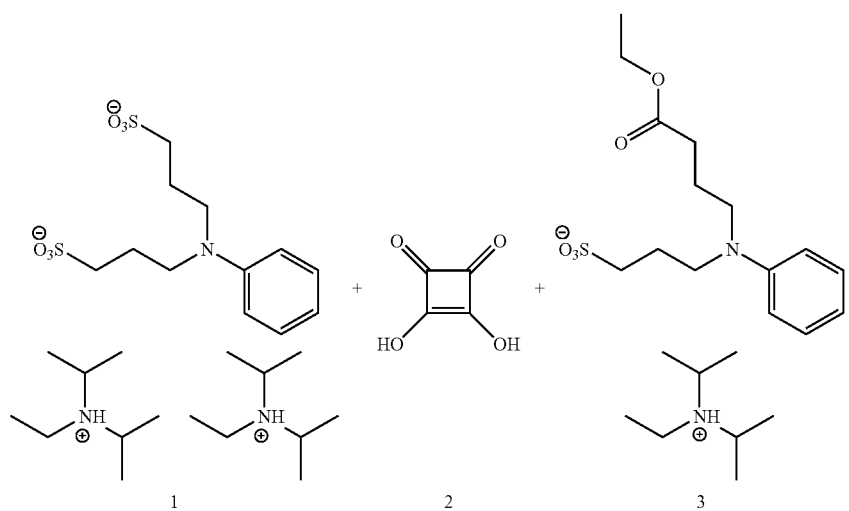
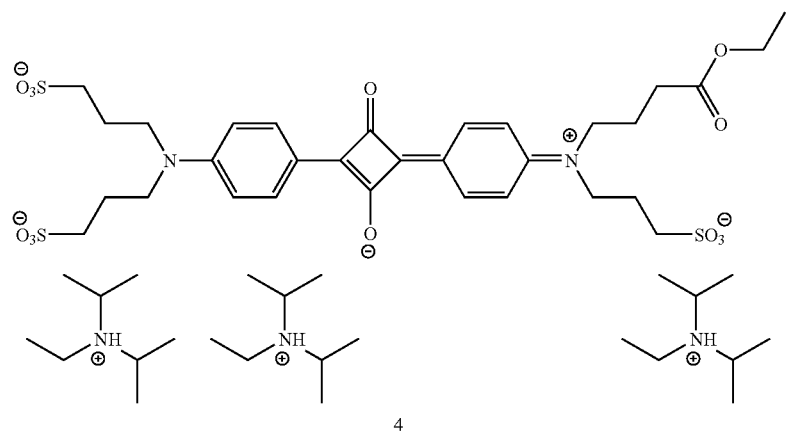

Squaric Acid Precursors

Compounds 2a and 2b are commercially available. 1,3-Dithiosquaric acid disodium salt (2c) and triethylammonium 2-butoxy-3-dicyanomethylene-4-oxo-1-cyclobuten-1-olate (2d) were synthesized according to Seitz et al., Chem. Ber. 112, 990-999, (1979) and Gerecht et al., Chem. Ber. 117, 2714-2729 (1984), respectively.

The 3-cyanoimino-4-oxo-1-cyclobutene-1,2-diolate (2e) is synthesized starting from dibutylsquarate according to the procedure of K. Köhler et al. Chem. Ber. 118, 1903-1916 (1985).

| 2 | $R_1$ | $R_2$ | $R_3$ | $R_4$ |
|---|---|---|---|---|
| a | O | O | OH | OH |
| b | O | O | $OC_4H_9$ | $OC_4H_9$ |
| c | S | O | $S^-Na^+$ | $O^-Na^+$ |
| d | O | $C(CN)_2$ | $OC_4H_9$ | $O^-HNEt_3^+$ |
| e | N—CN | O | $O^-K^+$ | $O^-K^+$ |

Synthesis of Intermediates for Ring-Substituted Squaraines

The syntheses of these intermediates are described in Tatarets et al., Analytica Chimica Acta 570, 214-223 (2006), Tatarets et al., Dyes & Pigments 64, 125-134 (2005), and in International Patent Application Serial No. PCT/US2003/010995.

Synthesis of Precursors for Leigh-Type Amide Rotaxanes

Synthesis of 1,4-Bis(aminomethyl)-2,5-dimethoxybenzene

The starting material 1,4-dibromo-2,5-dimethoxybenzene is commercially available from Aldrich: catalog number: 461105. The dicyano compound was synthesized from this starting material by reacting it with CuCN according to Neidlein et al., Chem. Ber. 119(3). 844-849 (1986), in N-methylpyrrolidone at 190° C. and the 1,4-bis(aminomethyl)-2,5-dimethoxybenzene (CAS registry number: 2745-67-7) is synthesized via reduction with $LiAlH_4$ in ether, analogously to Sasaki et al., J. Org. Chem., 65 (2), 275-283 (2000).

Synthesis of Modified Rotaxane Ring-Structures

A possible route to a more hydrophilic rotaxane macrocycle that contains hydroxy-methyl groups is described by Fieser et al. in Am. Soc. 68 (1946), 2249.

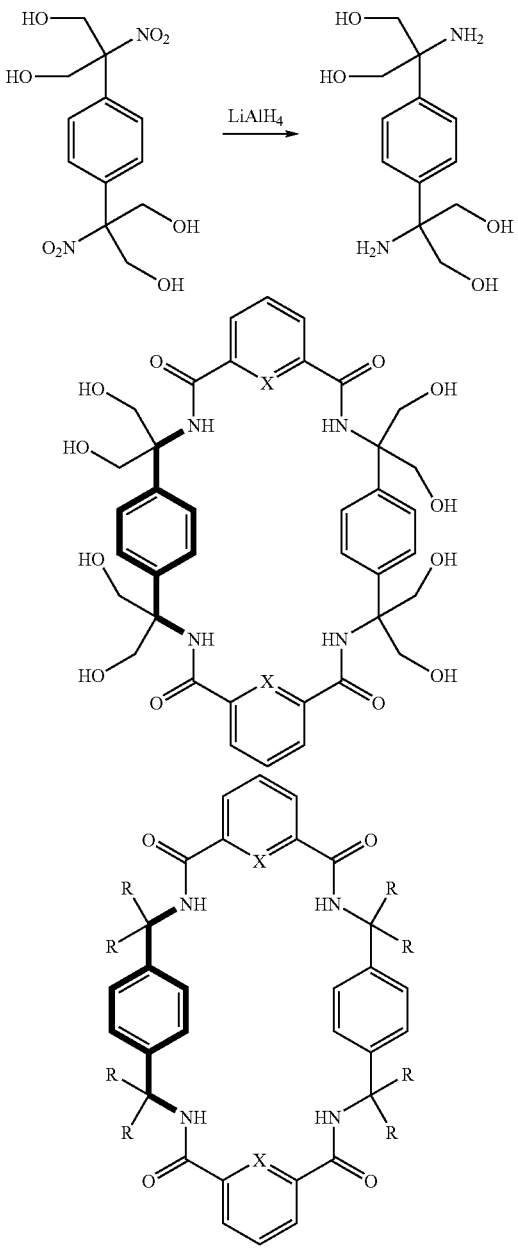

Other amide-type rotaxane structures for the synthesis of squaraine-rotaxanes are listed under Example 14.

Synthesis of ring-substituted 2,6-pyridine-dicarboxylic acid dichlorides

These starting materials are described in the following references: The synthesis of 4-methoxy-pyridine-2,6-dicarbonyl dichloride was described by Haldar et al., Tetrahedron 63 (27), 6322-6330 (2007). The synthesis of 4-(3-cyanopropoxy)-pyridine-2,6-dicarbonyl dichloride by Chaubet et al., Tetrahedron Lett. 31(40), 5729-5732 (1990). 4-hydroxy-pyridine-2,6-dicarbonyl dichloride was described by Barsu et al., Chem. Commun. 45, 4744-4746 (2006). The synthesis of 4-chloro-, 4-methoxy- and 4-nitro-pyridine-2,6-dicarbonyl dichloride was described by Bradshaw et al., J. Am. Chem. Soc. 102 (2) 467-474 (1980). It is understood that the nitro-group can be reduced to an amino-group and the amino-group can subsequently be protected with a group that is easily cleaved after rotaxane formation. A large number of protecting groups for various amino-groups are available from the literature. The amino-group can also be converted into an isothiocynate, which reacts readily with amines. These are just a few examples of ring-substituted starting materials that can be utilized as precursors to synthesize reactive and hydrophilic rotaxane structures.

Compounds Py1 and Py2 (Chelidamic Acid) are available from Aldrich. The synthesis of compound Py3 is described in U.S. Pat. No. 4,940,796. The synthesis of compounds Py4 and Py5 are described in J. Org. Chem. 63(1), 27-35 (1998). Dichloride Py6 can be synthesized from the acid Py5 according to conventional procedures using a chlorinating agent. Other substituted pyridines such as Py7 and Py8 can be synthesized via substitution of the chlorine in Py4 with primary or secondary amines.

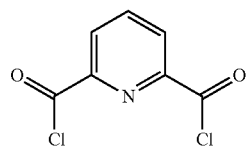

Py1

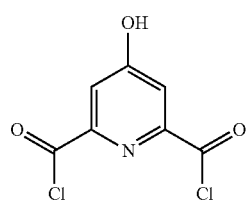

Py2

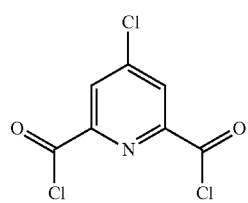

Py3

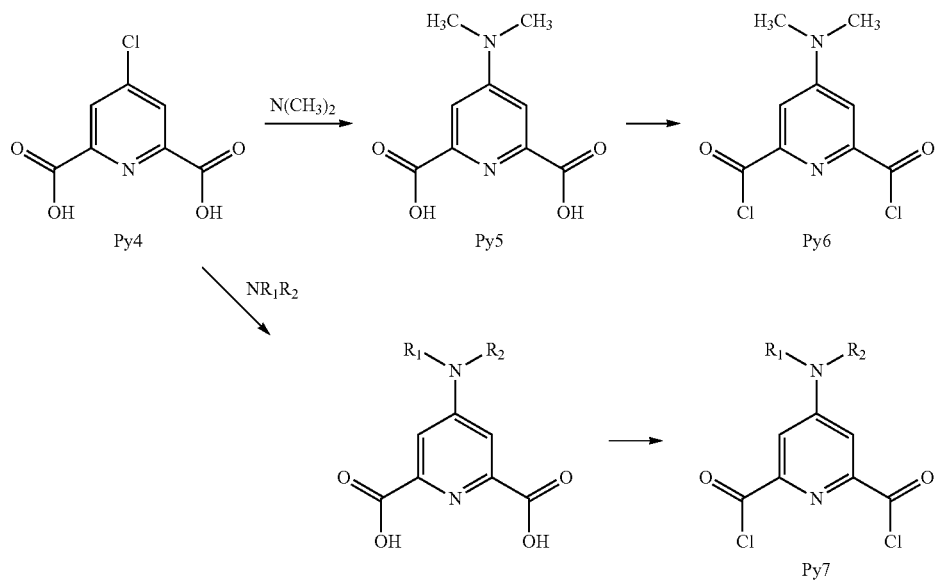

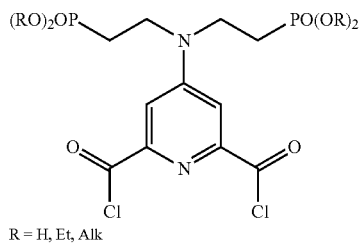

R = H, Et, Alk

Compound Py4 can also be used to synthesize alkoxy derivatives such as Py9:

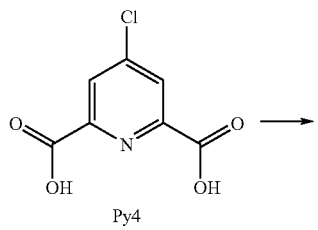

Py4

Synthesis of Di-(Aminomethyl) Substituted Compounds—Intermediates for Rotaxane Macrocycles 2,3,6,7-tetrahydrofuro[2',3':4,5]benzo[b]furan (THFBF) can be synthesized from 1,4-hydroquinone according to J. Chem. Soc., Perkin Trans. 1, 841-848 (1982) or J. Med. Chem. 39, 2953-2961 (1996):

Py8

Bromomethylation of THFBF followed by substitution of bromine with nitrogen gives 8-aminomethyl-2,3,6,7-tetrahydrofuro[2',3':4,5]benzo[b]furan-4-ylmethan amine (di(aminomethyl)-THFBF) useful for synthesis of rotaxane macrocycles:

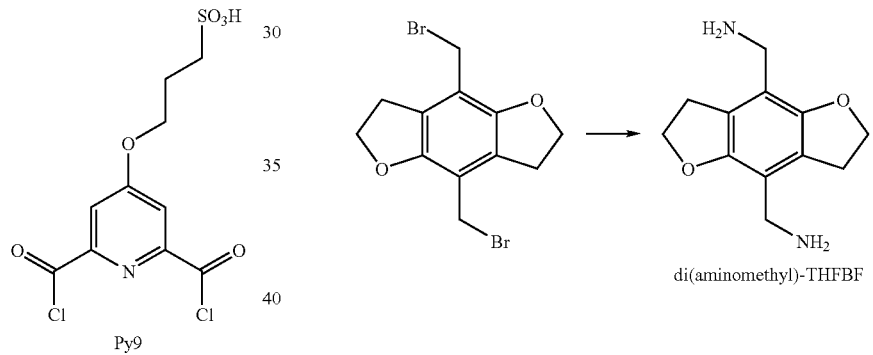

di(aminomethyl)-THFBF

Bromomethylation and amination can be done according to J. Am. Chem. Soc. 129, 15054-15059 (2007).

Oxidation of di(aminomethyl)-THFBF e.g. with dichloro dicyanoquinone (DDQ) gives 8-aminomethylfuro[2',3':4,5]benzo[b]furan-4-ylmethanamine.

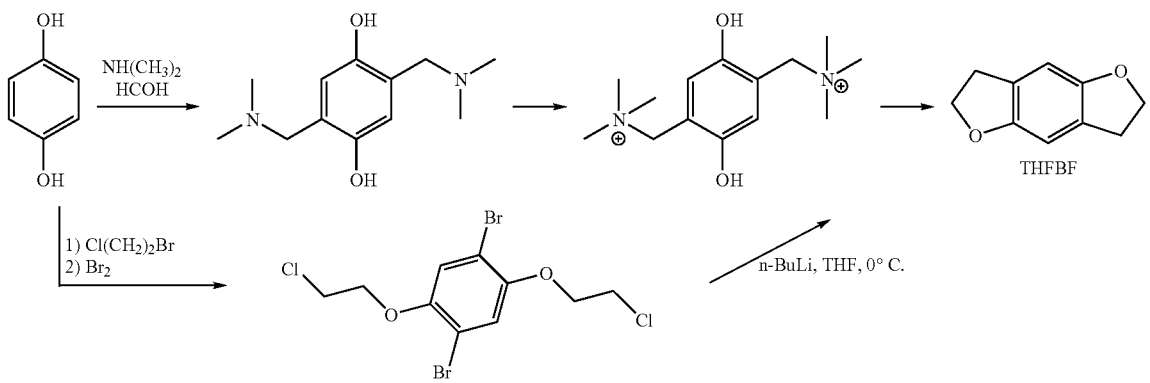

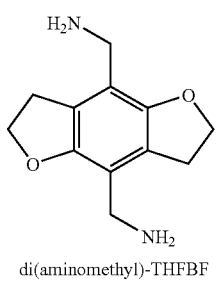
di(aminomethyl)-THFBF

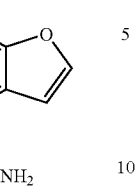

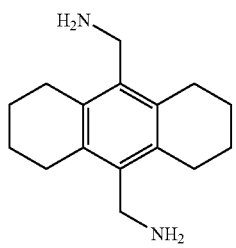
b

The above method can be used to synthesize other di(aminomethyl) derivatives as shown in the following scheme:

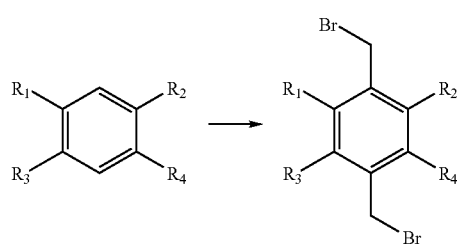

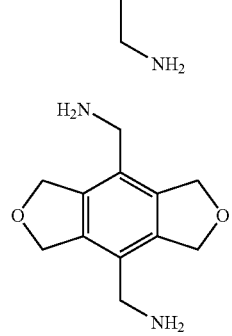
c d

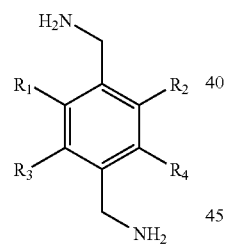

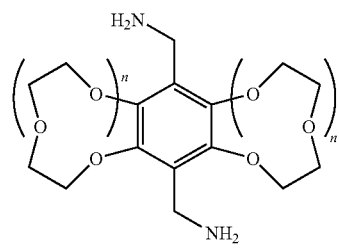
e

The synthesis of compound a is described in A. W. Van der Made, and R. H. Van der Made J. Org. Chem. 58 (5), 1262-1263 (1993) (DOI: 10.1021/jo00057a046). Starting materials for a-c are available from Aldrich:

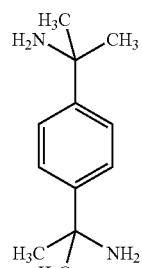
f a

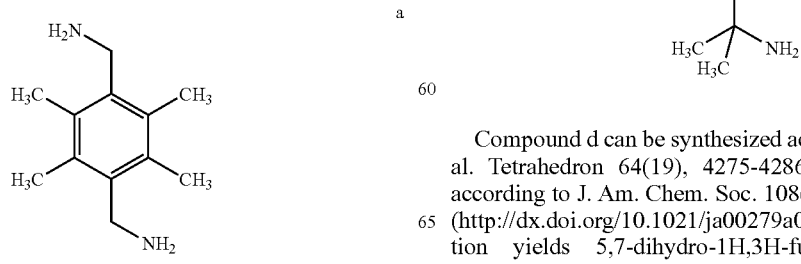

Compound d can be synthesized according to D. Garcia et al. Tetrahedron 64(19), 4275-4286 (2008). Bromination according to J. Am. Chem. Soc. 108(19), 6045-6046 (1986) (http://dx.doi.org/10.1021/ja00279a066), and heterocyclization yields 5,7-dihydro-1H,3H-furo[3,4-f]isobenzofuran (FBF). Compound g can be obtained analogously.

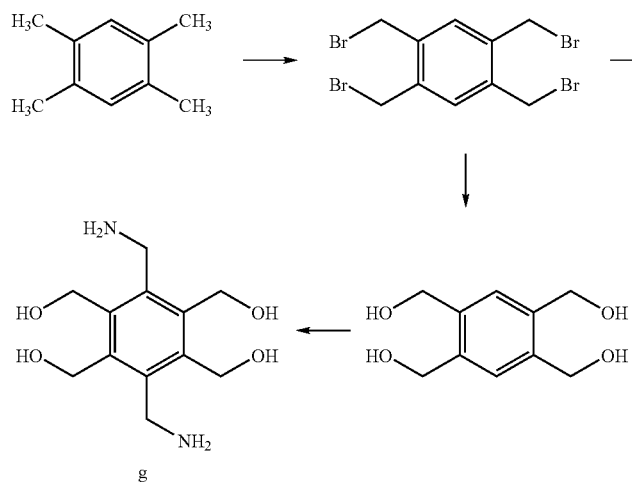
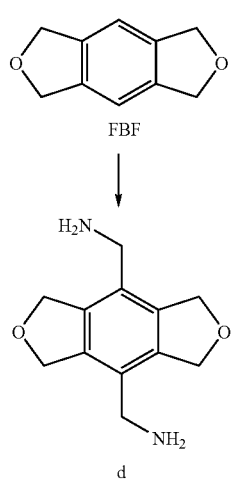

Alternatively, compound FBF can be obtained by the reduction of 1,2,3,4-benzenetetracarboxylic dianhydride (available from Aldrich):

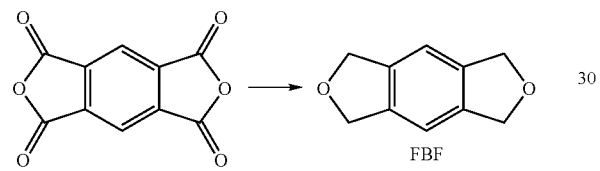

Compound e can be obtained using procedures described in Tetrahedon Lett. 35(39), 7255-7258 (1994).

Compound f is synthesized starting from 1,4-diisopropylbenzene (commercially available from Aldrich) according to the following scheme:

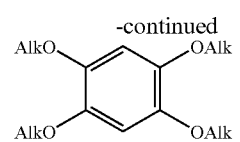
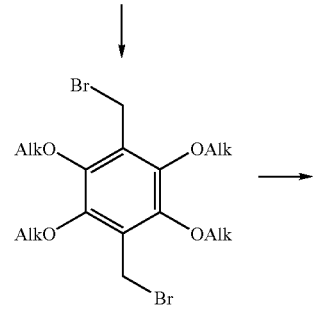

The same approach can be applied to synthesize the di-(aminomethyl) derivative h (J. Chem. Soc. Perkin Trans. 2, 229-240 (1996)). The starting material 2,5-dihydroxy-1,4-benzoquinone is available from Aldrich.

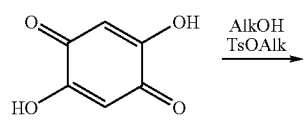
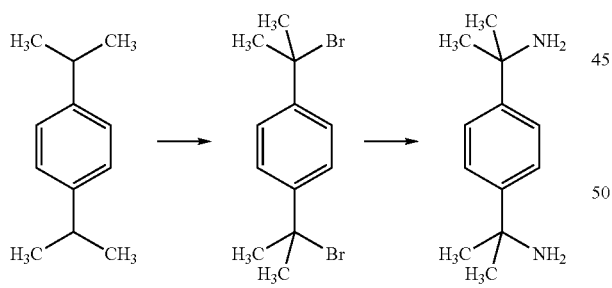

Example 2

Synthesis of the Hydrophobic Squaraine-Rotaxane 3

Squaraine dye 3a is synthesized analogously to procedures that are described in U.S. Patent Application Publication No. US2005/0202565. 3a: $\lambda_{max}$(abs) 647 nm (DMF/water=1:1), $\lambda_{max}$(em) 666 nm (DMF/water=1:1), Q.Y. 29% (DMF/water=1:1), $\lambda_{max}$(abs) 645 nm (DMF/water=1:2), $\lambda_{max}$(em) 664 nm (DMF/water=1:2):

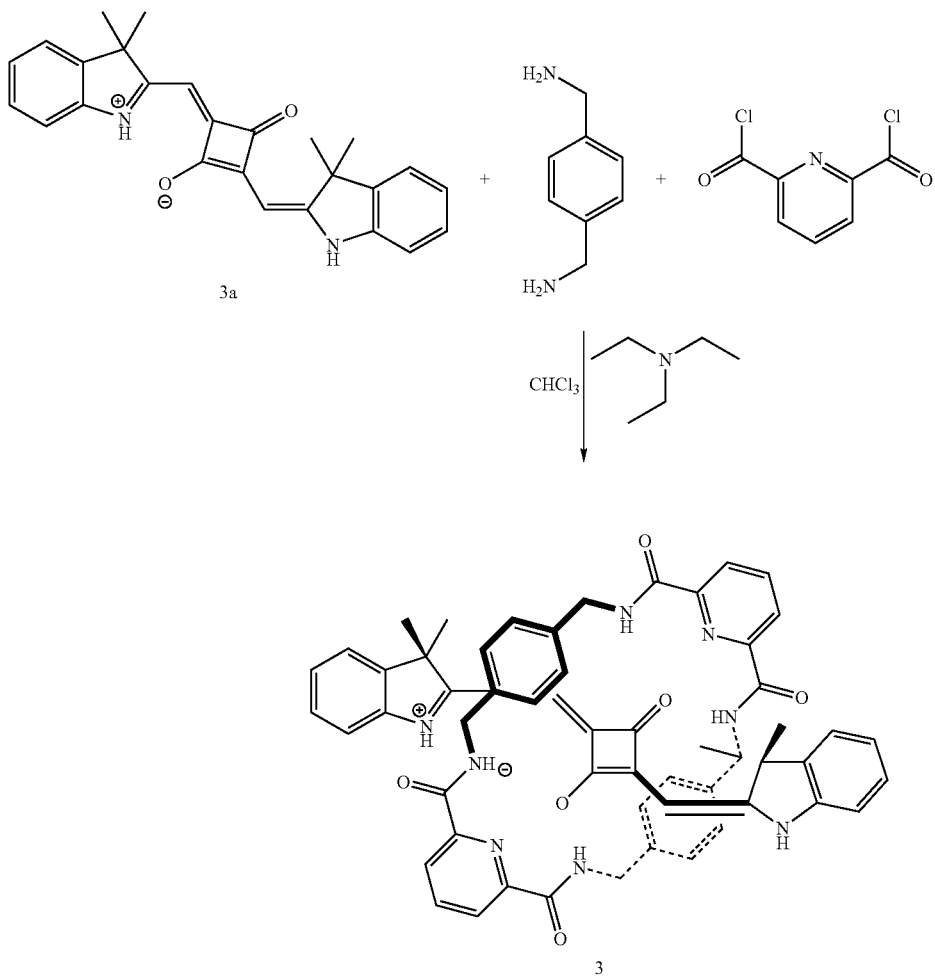

Clear solutions of 2,6-pyridinedicarbonyl dichloride (1.28 mmol) in 5 mL of chloroform and p-xylylenediamine (1.28 mmol) in 5 mL of chloroform were simultaneously added dropwise over 5 h to a stirred solution of 3a (0.32 mmol) and triethylamine (3.2 mmol) in 40 mL of $CHCl_3$. After overnight stirring, the mixture containing rotaxane 3 and polymer co-products was filtered, washed with chloroform (100 mL) to extract rotaxane 3, and the filtrate was concentrated. Purification of the crude product by column chromatography using silica gel (gradient 0-1.5% of MeOH n $CH_2Cl_2$) gave rotaxane 3. $\lambda_{max}$ (abs): 642 nm (DMF/water=1:2), $\lambda_{max}$(em): 659 nm (DMF/water=1:2); Q.Y. 35% (DMF/water=1:2): $^1$H-NMR $\delta_H$ (200 MHz, $CDCl_3$): 11.94 (s, 2H), 9.69 (d, J=9.7 Hz, 4H), 8.59 (d, J=7.5 Hz, 4H), 8.22 (t, J=7.5 Hz, 2H), 7.35-7.05 (m, 8H), 6.88 (s, 8H), 5.45 (d, J=10.3 Hz, 2H), 5.38 (d, J=10.3 Hz, 2H), 4.78 (s, 2H), 3.78 (d, J=14.5 Hz, 4H), 1.58 (s, 12H).

Example 3

Synthesis of Squaraine-Rotaxane 4

Squaraine dye 4a was synthesized as described in U.S. Patent Application Publication No. US2005/0202565. 4a: $\lambda_{max}$ (abs)=638 nm, $\lambda_{max}$ (em)=654 nm, Q.Y.: 25% (water), $\tau$=1.56 ns (water).

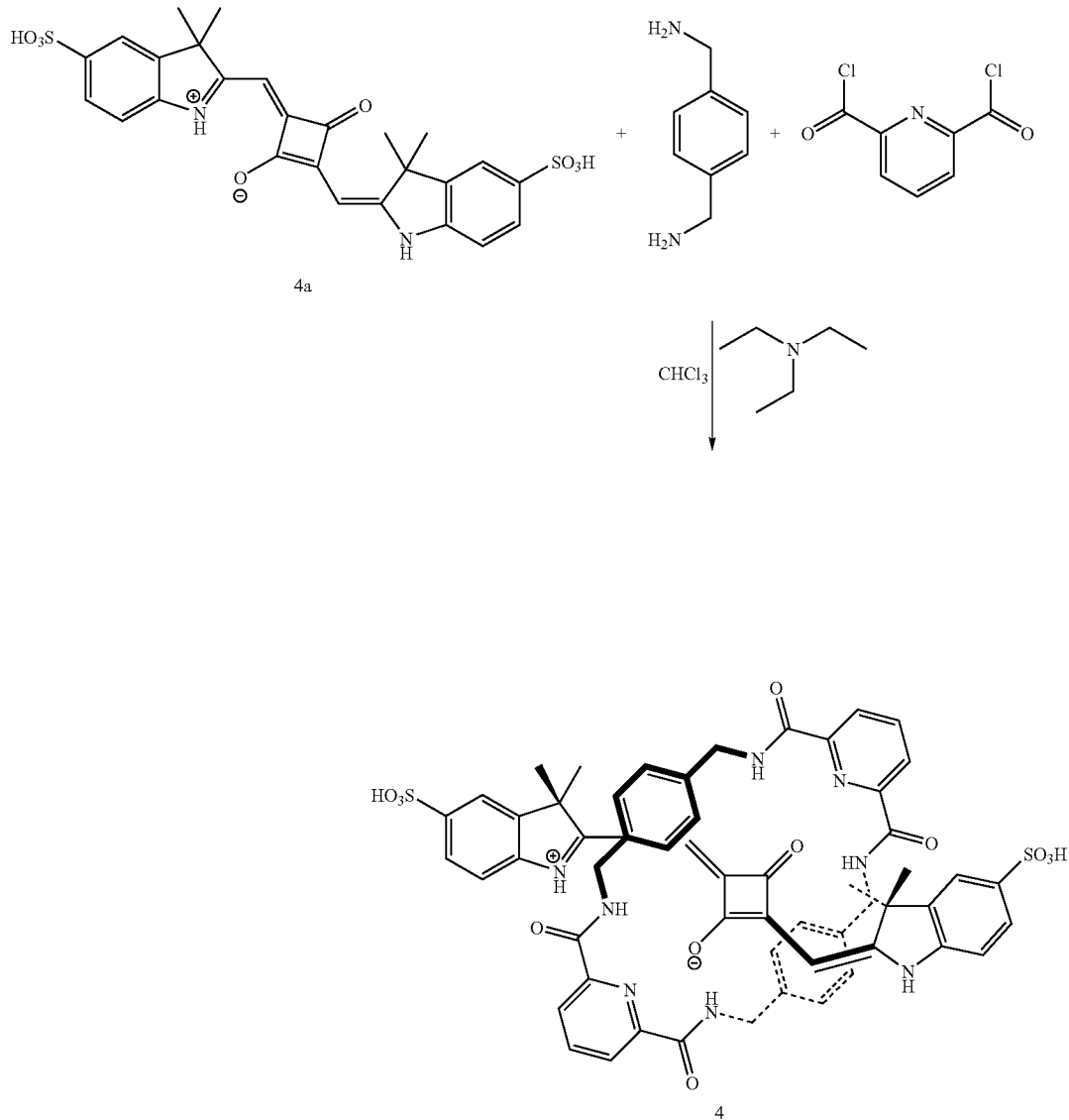

Clear solutions of 2,6-pyridinedicarbonyl dichloride (1.28 mmol) in 5 mL of chloroform and p-xylylenediamine (1.28 mmol) in 5 mL of chloroform were simultaneously added dropwise over a period of 5 h to a stirred solution of 4a (0.32 mmol) and triethylamine (3.2 mmol) in 40 mL of CHCl$_3$ and 1.5 ml of methanol. After overnight stirring, the mixture containing rotaxane 4 and polymer co-products was filtered, washed with chloroform (100 mL) to extract rotaxane 4, and the filtrate was concentrated. The crude product was column purified (RP-18, MeOH/water, gradient) to give rotaxane 4. $\lambda_{max}$(abs)=640 nm (water), $\lambda_{max}$(em)=656 nm (water), Q.Y.: 40% (water), τ=2.4 ns (water).

Example 4

Synthesis of Squaraine-Rotaxane 5

Squaraine dye 5a was synthesized analogously as described in Terpetschnig et al., Dyes & Pigments 21 (3), 227-234 (1993). $\lambda_{max}$(abs)=681 nm, $\lambda_{max}$(em)=697 nm, Q.Y.: 58% (chloroform). $\tau_1$=0.6 ns (2%), $\tau_2$=3.42 (98%), $\tau_{mean}$=3.36 ns (chloroform).

Clear solutions of 2,6-pyridinedicarbonyl dichloride (1.28 mmol) in 5 mL of chloroform and p-xylylenediamine (1.28 mmol) in 5 mL of chloroform were simultaneously added dropwise over 5 h to a stirred solution of 5a (0.32 mmol) and triethylamine (3.2 mmol) in 40 mL of CHCl$_3$ and 1.5 mL of methanol. After overnight stirring, the mixture containing rotaxane 5 and polymer co-products was filtered, washed with chloroform (100 mL) to extract rotaxane 5, and the filtrate was concentrated. The crude product was column purified (RP-18, 0-1.5% MeOH in CHCl$_3$, gradient) to give rotaxane 5. $\lambda_{max}$(abs)=676 nm, $\lambda_{max}$(em)=690 nm, Q.Y. 59% (CHCl$_3$); $\tau_1$=0.86 ns (2%), $\tau_2$=3.59 ns (98%) %, $\tau_{mean}$=3.52 (CHCl$_3$).

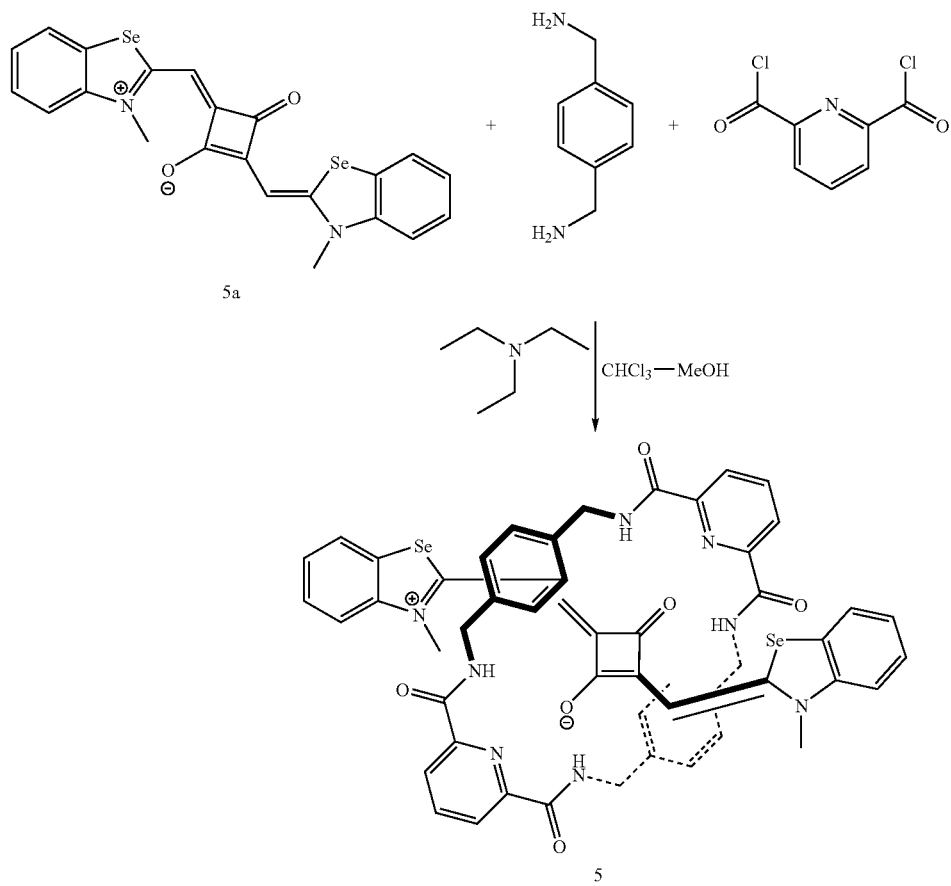

Example 5

Synthesis of Rotaxane 6

Squaraine dye 6a was synthesized analogously as described in Terpetschnig et. al., Dyes & Pigments 21 (3), 227-234 (1993). $\lambda_{max}$ (abs)=681 nm, $\lambda_{max}$(em)=, 698 nm, Q.Y.: 57% (chloroform).

Clear solutions of 2,6-pyridinedicarbonyl dichloride (1.28 mmol) in 5 mL of chloroform and p-xylylenediamine (1.28 mmol) in 5 mL of chloroform were simultaneously added dropwise over 5 h to a stirred solution of squaraine dye 6a (0.32 mmol) and triethylamine (3.2 mmol) in 40 mL of $CHCl_3$ and 1.5 mL of methanol. After stirring overnight, the mixture containing rotaxane 6 and polymer co-products was filtered, washed with chloroform (100 mL) to extract rotaxane 6, and the filtrate was concentrated. Purification of the crude product by column chromatography using Silica Gel (gradient 0-1.5% MeOH in $CHCl_3$) gave rotaxane 6. 6: $\lambda_{max}$(abs)=661 nm, $\lambda_{max}$ (em)=674 nm, Q.Y.: 66% ($CHCl_3$).

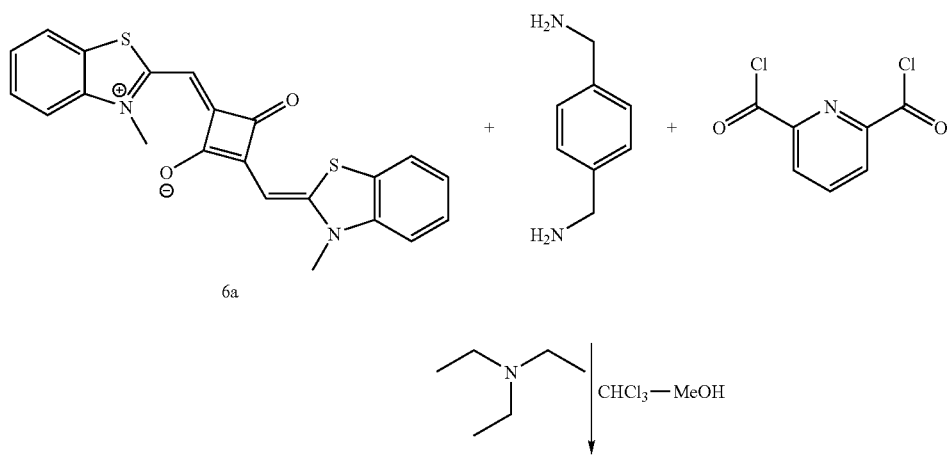

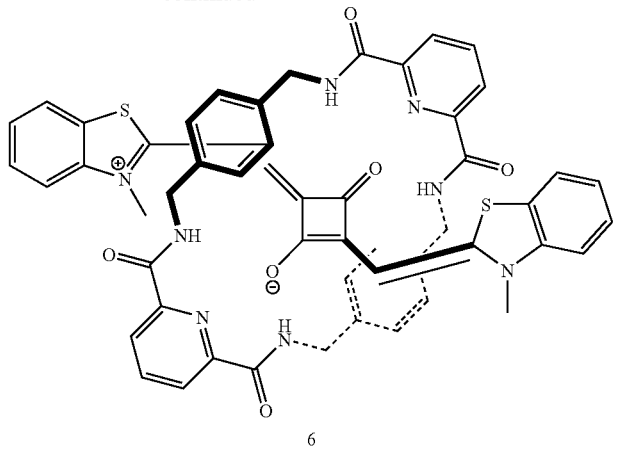

6

Example 6

Synthesis of Squaraine-Rotaxane Dye 7

Squaraine Dye 7a

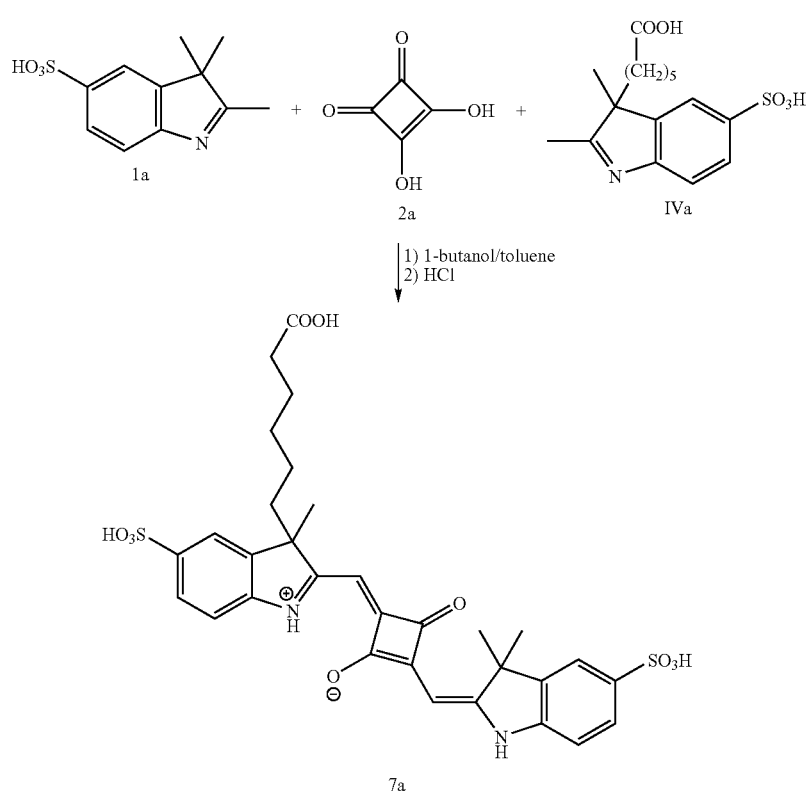

A mixture of 350 mg (1.47 mmol) of 2,3,3-trimethyl-3H-5-indolesulfonic acid (1a), 500 mg (1.47 mmol) of 6-(2,3-dimethyl-5-sulfo-3H-3-indolyl) hexanoic acid (IVa), and 220 mg (1.92 mmol) of 3,4-dihydroxy-3-cyclobutene-1,2-dione 2a was heated at reflux in a mixture of 30 mL of 1-butanol and 10 mL of toluene for 15 h with a Dean-Stark trap. The solvent was removed under reduced pressure and the obtained residue was refluxed with 70 mL of 0.2 M HCl for an hour and then water was removed under reduced pressure. Crude product was twice purified by a column chromatography (Silica gel 60 RP-18, 0-5% methanol-water) to give 65 mg (6.7%) of 7a; $\delta_H$ (200 MHz, DMSO-$d_6$) 12.78 (2H, broad s, NH), 7.66 (1H, s, arom H), 7.61 (1H, s, arom H), 7.56 (2H, dd, 8.5, 1.2 Hz, arom H), 7.16 (2H, d, 8.1 Hz, arom H), 5.58 (1H, s, CH), 5.54 (1H, s, CH), 2.07 (2H, t, 6.9 Hz, $CH_2$COOH), 2.02-1.74 (2H, m, C$\underline{H}_2$), 1.44 (6H, s, (C$\underline{H}_3$)$_2$), 1.42 (3H, s, (C$\underline{H}_3$)$_2$), 1.37-1.05

(4H, m, CH$_2$), 1.00-0.45 (2H, m, CH$_2$). $\lambda_{max}$ (abs): 638 nm, $\lambda_{max}$ (em): 655 nm, (PBS); Q.Y.: 31% (PBS).

Squaraine-Rotaxane 7

Solutions of 2,6-pyridinedicarbonyl dichloride (1.28 mmol) in 5 mL of chloroform and p-xylylenediamine (1.28 mmol) in 5 mL of chloroform were simultaneously added dropwise over a period of 5 h to a stirred solution of 7a (0.32 mmol) and triethylamine (3.2 mmol) in 40 mL of CHCl$_3$ and 1.5 mL of methanol. After stirring overnight, the mixture containing rotaxane 7 and polymer co-products was filtered, washed with methanol/water 1:1 (100 mL) to extract rotaxane 7, and the filtrate was concentrated. The crude product was column purified (RP-18, MeOH/water, gradient) to give rotaxane 7. $\lambda_{max}$(abs): 642 nm (water); $\lambda_{max}$(em): 658 nm.

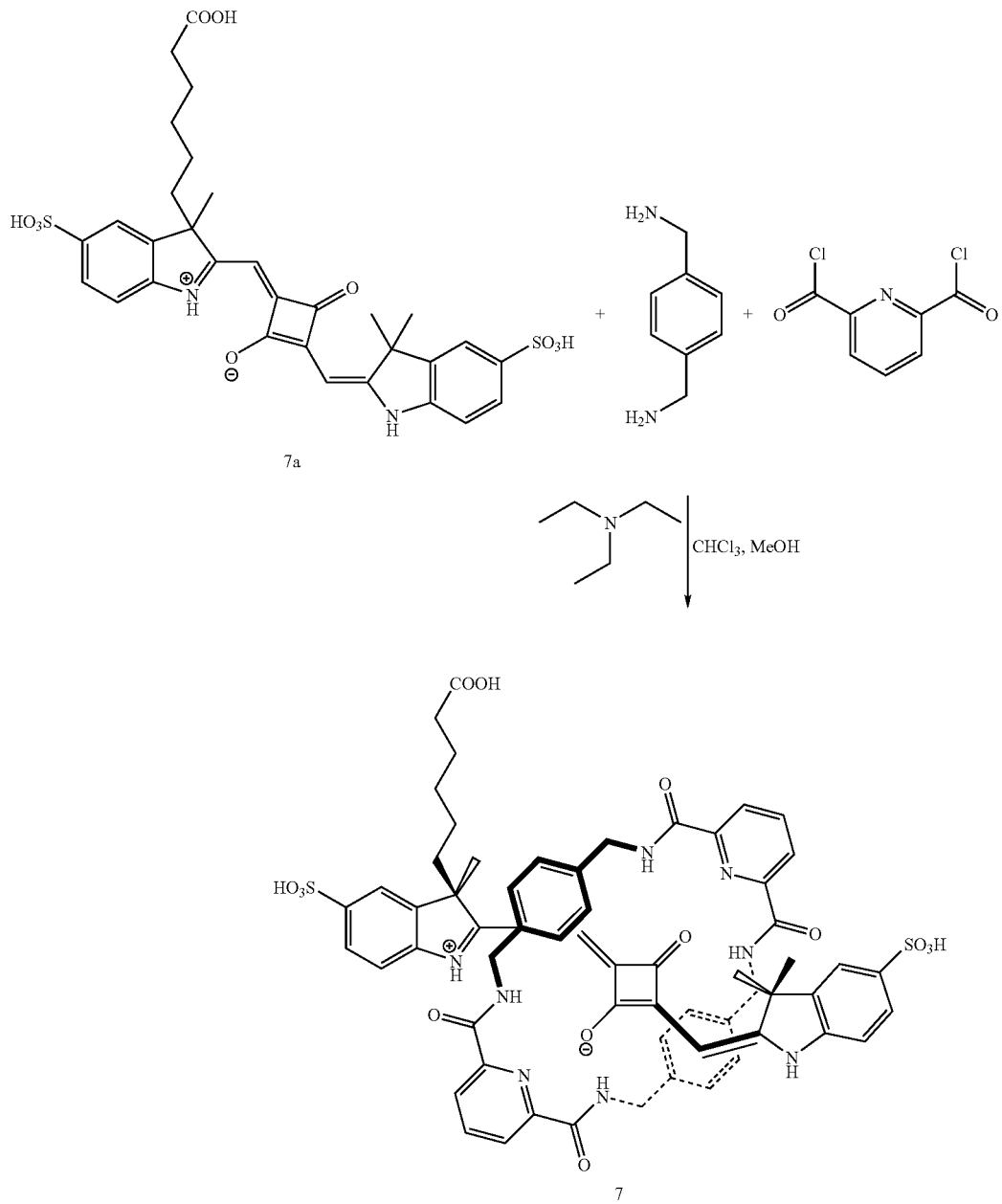

Synthesis of NHS-Ester 7b with TSTU 25.0 µmol of compound 7 (32.22 µmol) TSTU, and 6.5 µL (37.32 µmol) of DIPEA were dissolved in 3 mL of DMF. The solution was stirred at room temperature for 3 h. The reaction was monitored by TLC (RP-18, acetonitrile-water). After completion, the reaction mixture was sealed under argon and stored in the refrigerator until further use. To isolate the solid NHS ester, the solvent was removed under reduced pressure and the residue washed several times with ether.

Example 7

Synthesis of Squaraine-Rotaxane 8 a) Synthesis of N-diphenylmethanimine

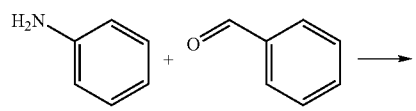

Aniline (53.7 mmol) was added under stirring to benzaldehyde 2 (53.7 mmol), stirred for 15 min and treated with 8 mL of 96% ethanol. After the crystalline N-diphenylmethanimine is formed, it was filtered and recrystallized from 10 mL of 85% aq. ethanol to give N-diphenylmethanimine with 70% yield.

b) Synthesis of N-benzyl-aniline

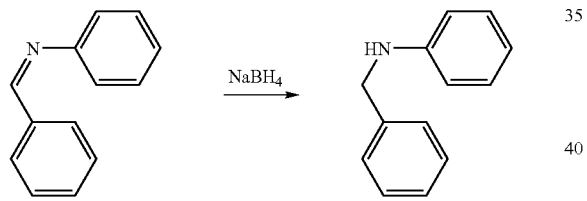

66.21 mmol of sodium borohydride were added over 3 h at room temperature to a solution of N-diphenylmethanimine (16.55 mmol) in 50 mL of methanol. The mixture was stirred for 3 h, diluted with 200 mL of water and the crude N-benzyl-aniline was extracted with methylene chloride. The product was recrystallized from hexane to give N-benzyl-aniline with 84% yield. M.P.: 38° C.

c) Synthesis of 6-Benzylanilinohexanoic acid

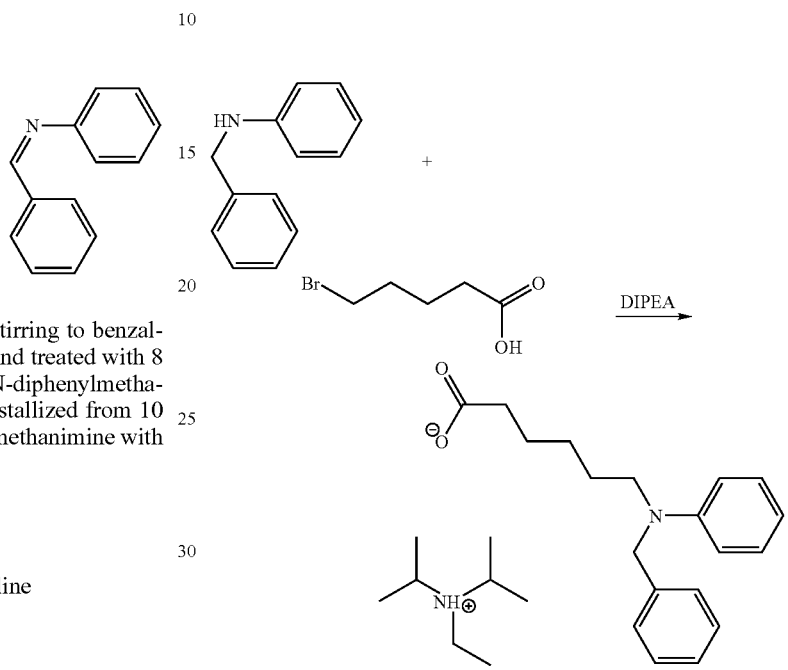

A mixture of N-benzylaniline (10 mmol), 6-bromohexanoic acid 5 (12 mmol) and N,N-diisopropylethylamine (DIPEA, 22 mmol) was heated in 10 mL acetonitrile at 120-130° C. for 6 h in a pressure tube under argon atmosphere. The solvent was evaporated and ether was added. The precipitated DIPEA bromide was filtered and the filtrate was evaporated. The isolated 6-benzylanilinohexanoic acid was dried under vacuum and used for further synthesis without purification.

d) Synthesis of Squaraine Dye 8a

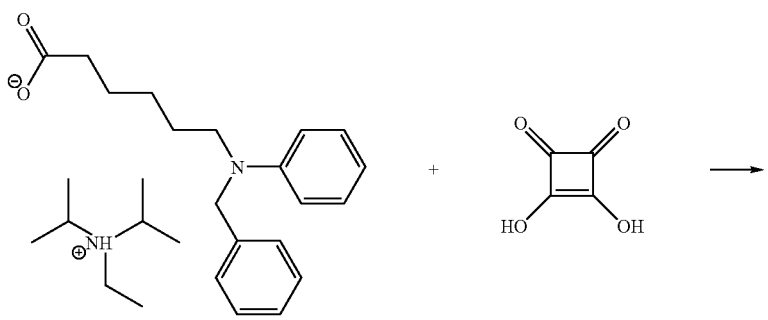

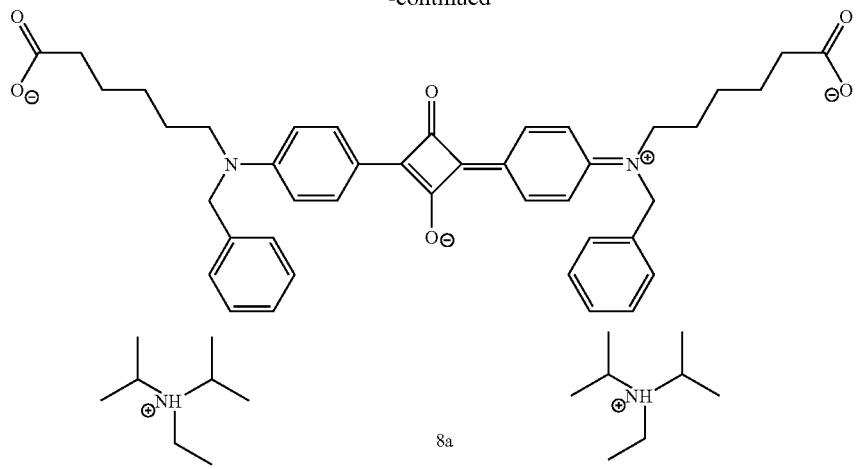

8a

A mixture of the anilinohexanoic acid (1.83 mmol) and squaric acid (0.92 mmol) was refluxed in a mixture of n-butanol (15 mL) and toluene (30 mL) for 12 h. The deep green reaction mixture was concentrated and the crude product was precipitated with the addition of 30-40 mL ether. After filtering, the product was washed several times with ether to yield the dark green squaraine dye as a solid. Purification of the crude product by column chromatography using silica gel (gradient 0-1.5% MeOH in CHCl3) gave squaraine 8a. Yield: 20%. $\lambda_{max}$ (abs): 634 nm (CHCl$_3$), $\lambda_{max}$ (em): 652 nm (CHCl$_3$).

e) Synthesis of Squaraine-Rotaxane 8

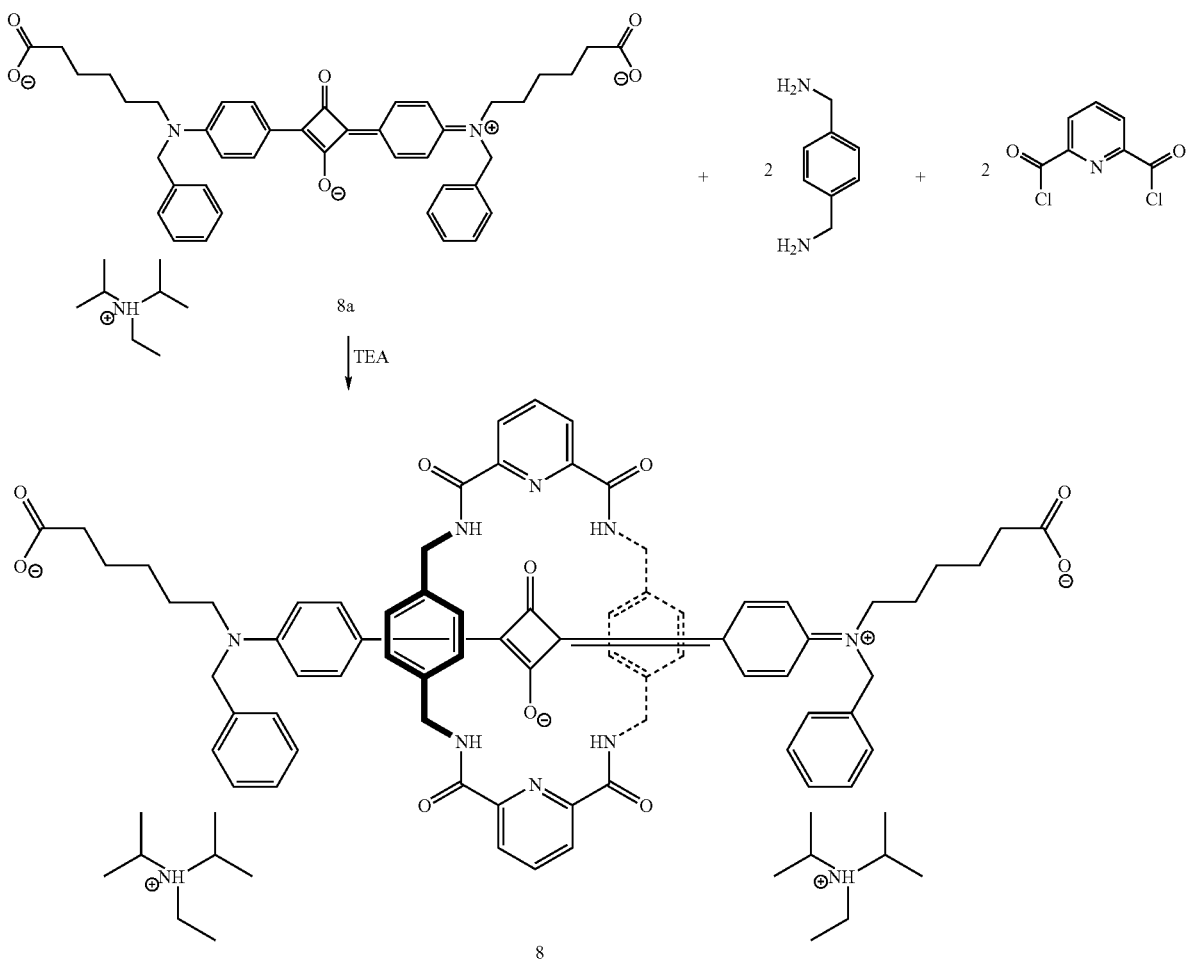

8

Clear solutions of 2,6-pyridinedicarbonyl dichloride 10 (1.28 mmol) in 5 mL of chloroform and p-xylylenediamine (1.28 mmol) in 5 mL of chloroform were simultaneously added dropwise over 5 h to a stirred solution of squaraine 8a (0.32 mmol) and triethylamine (3.2 mmol) in 40 mL of CHCl$_3$. After overnight stirring, the mixture containing rotaxane 8 and polymer co-products was filtered, washed with chloroform (100 mL) to extract rotaxane 8, and the filtrate was concentrated. Purification of the crude material by column chromatography using silica gel (gradient, 0-1.5% of MeOH in CHCl$_3$) gave the rotaxane 8. 8: $\lambda_{max}$ (abs): 645 nm (CHCl$_3$), $\lambda_{max}$ (em): 660 nm (CHCl$_3$); Q.Y.: 70% (CHCl$_3$).

Example 8

Synthesis of Rotaxane 9 a) Synthesis of ethyl 4-(3-ethyloxycarbonylpropylanilino)butanoate

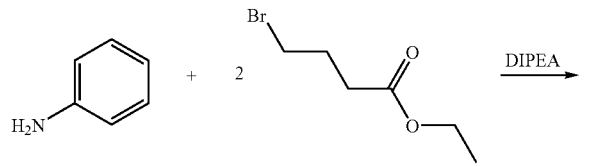

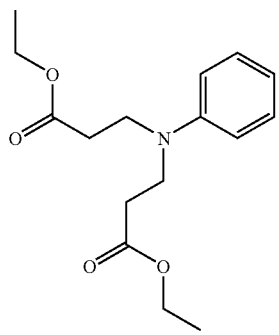

A mixture of aniline (7 mmol), N,N-diisopropylethylamine (DIPEA, 18 mmol) and ethyl 4-bromobutanoate (16 mmol) was heated in 10 mL acetonitrile at 120-130° C. for 9 h in a pressure tube under argon atmosphere. The solvent was evaporated and ethylacetate was added. The precipitated DIPEA bromide was filtered off and the filtrate was evaporated. The residue of ethyl 4-(3-ethyloxycarbonylpropylanilino)butanoate was dried in a vacuum-desiccator and used for further synthesis without purification.

b) Synthesis of Squaraine Dye 9a

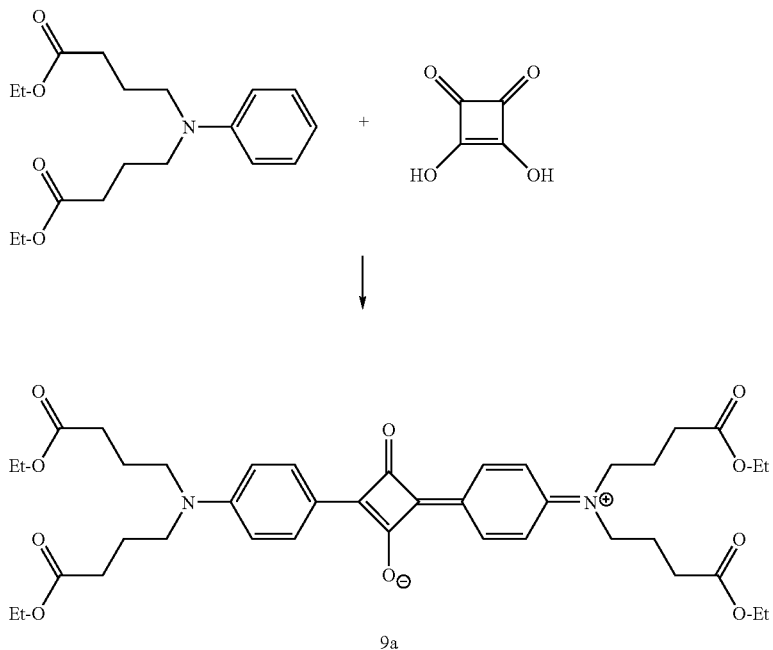

A mixture of ethyl 4-(3-ethyloxycarbonylpropylanilino)butanoate (1.83 mmol) and squaric acid (0.92 mmol) was refluxed in a mixture of n-butanol (15 mL) and toluene (30 mL) for 12 h. After cooling, the solvent was removed on a rotary evaporator, and the residue was purified by column chromatography using silica gel (gradient 0-2% MeOH in CHCl$_3$) to give squaraine 9a. 9a: $\lambda_{max}$ (abs): 633 nm (CHCl$_3$).

c) Synthesis of Squaraine-Rotaxane Dye 9b

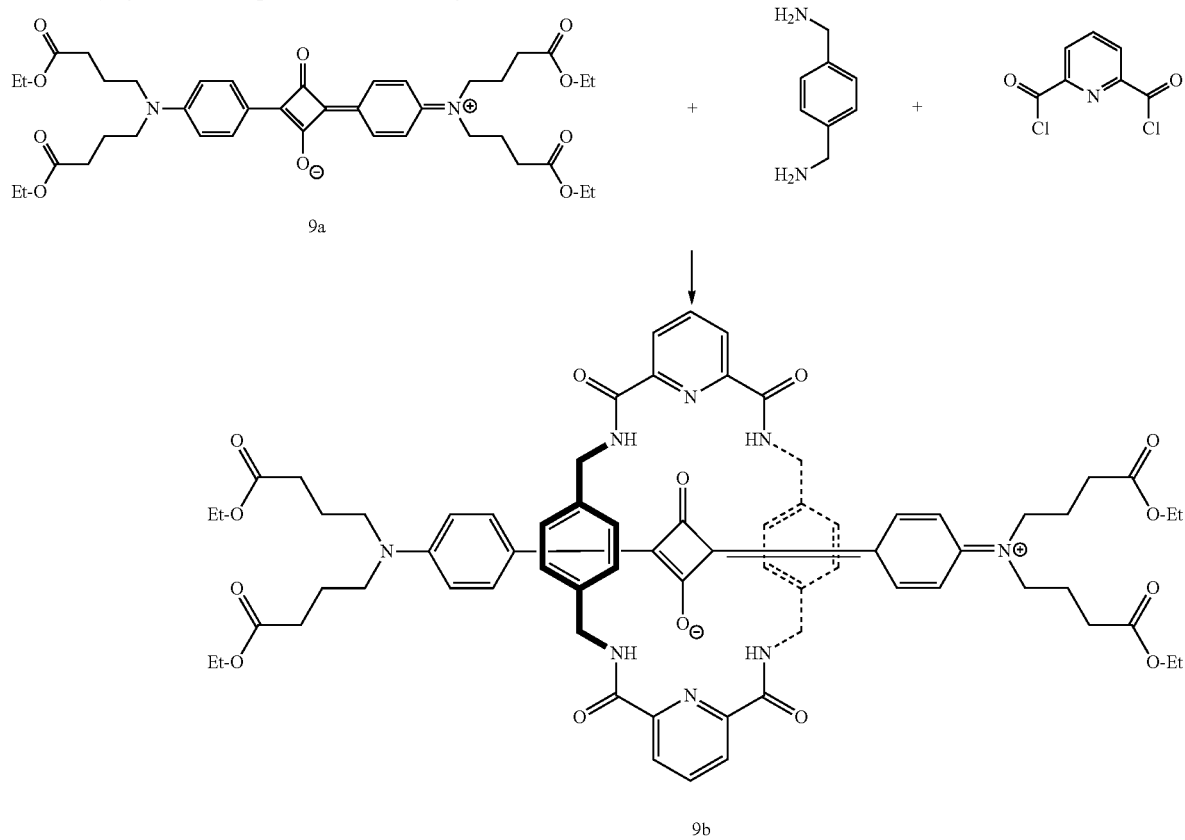

Clear solutions of 2,6-pyridinedicarbonyl dichloride (1.26 mmol) in 5 mL of chloroform and p-xylylenediamine (1.28 mmol) in 5 mL of chloroform were simultaneously added dropwise over 5 h to a stirred solution of squaraine 9a (0.32 mmol) and triethylamine (3.2 mmol) in 40 mL of CHCl$_3$. After overnight stirring, the mixture containing rotaxane 9b and polymer co-products was filtered off, washed with chloroform (100 mL) to extract rotaxane 9b, and the filtrate was concentrated. Crude product was column purified using silica gel (gradient 0-2% MeOH in CHCl$_3$) to give rotaxane 9b. $\lambda_{max}$ (abs): 644 nm (CHCl$_3$).

d) Synthesis of Squaraine-Rotaxane Dye 9

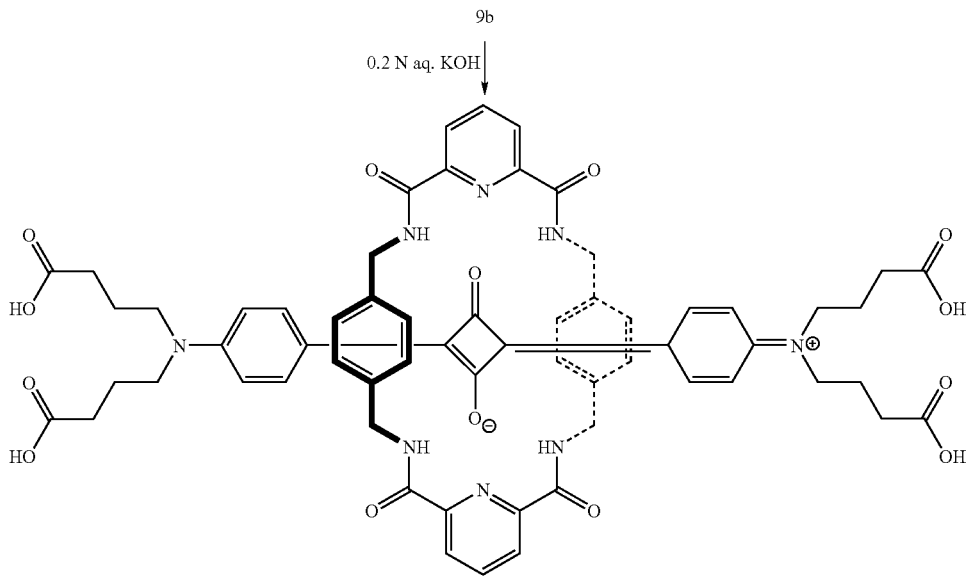

2 mmol of dye 9b were stirred for 3 h at room temperature in the mixture of 25 mL of ethanol and 25 mL of 0.2 N aqueous solution of KOH. Then the mixture was neutralized with 0.2 N HCl and the resulted solution was column purified (RP-18; methanol/water, gradient) to give squaraine-rotaxane 9.

Example 9

Synthesis of Squaraine-Rotaxane 10 a) Synthesize of 3-phenylammonio-1-propanesulfonate

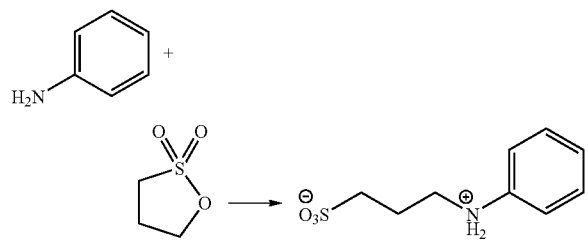

A mixture of aniline (7 mmol) and propane sultone (10 mmol) was heated in 10 mL of acetonitrile at 12.0-130° C. for 9 h in a pressure tube under argon atmosphere. The product was allowed to cool to room temperature and the solid of 3-phenylammonio-1-propanesulfonate was filtered and air-dried. Yield: 95%.

b) Synthesis of 3-(3-ethyloxycarbonylpropylanilino)-1-propanesulfonate

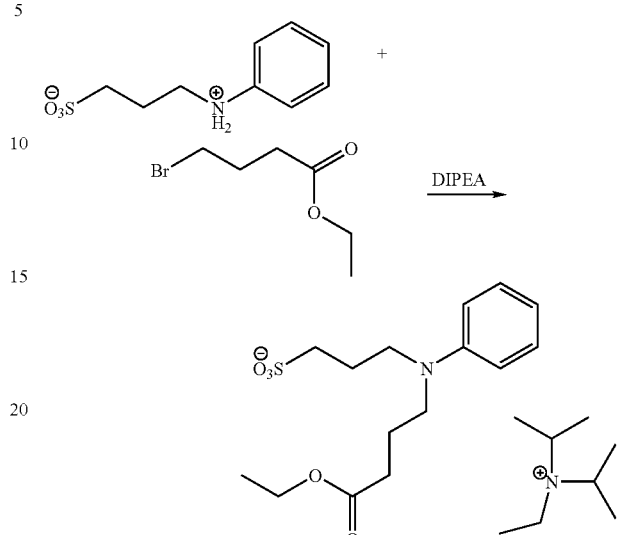

A mixture of 3-phenylammonio-1-propanesulfonate (10 mmol), ethyl 4-bromobutanoate (12 mmol) and N,N-diisopropylethylamine (DIPEA, 22 mmol) was heated in 10 mL acetonitrile at 120-130° C. for 6 h in a pressure tube under argon atmosphere. The solvent was removed under reduced pressure and ethyl acetate was added. The precipitated DIPEA bromide was filtered and the filtrate was evaporated. The residue of ethyl-diisopropyl-ammonium 3-(3-ethyloxycarbonylpropylanilino)-1-propanesulfonate was dried under vacuum and used for further synthesis without purification.

c) Synthesis of Squaraine Dye 10a

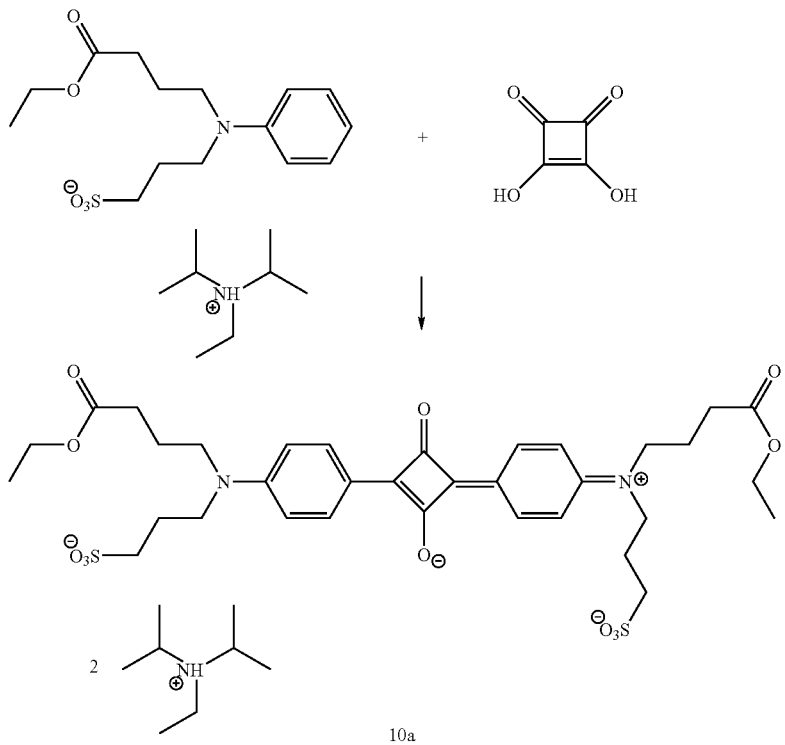

10a

A mixture of dialkylaniline (1.83 mmol) and squaric acid (0.92 mmol) was refluxed in a solvent-mixture of n-butanol (15 mL) and toluene (30 mL) for 12 h. Then the deep green reaction mixture was concentrated and the crude product was precipitated by adding 30-40 mL of ether. After filtering, the product was washed several times with ether to yield the dark green squaraine dye 10a as a solid. Yield: 30%. $\lambda_{max}$ (abs): 644 nm, $\lambda_{max}$ (em): 670 nm, Q.Y.: 3% (water).

d) Synthesis of Squaraine-Rotaxane 10b

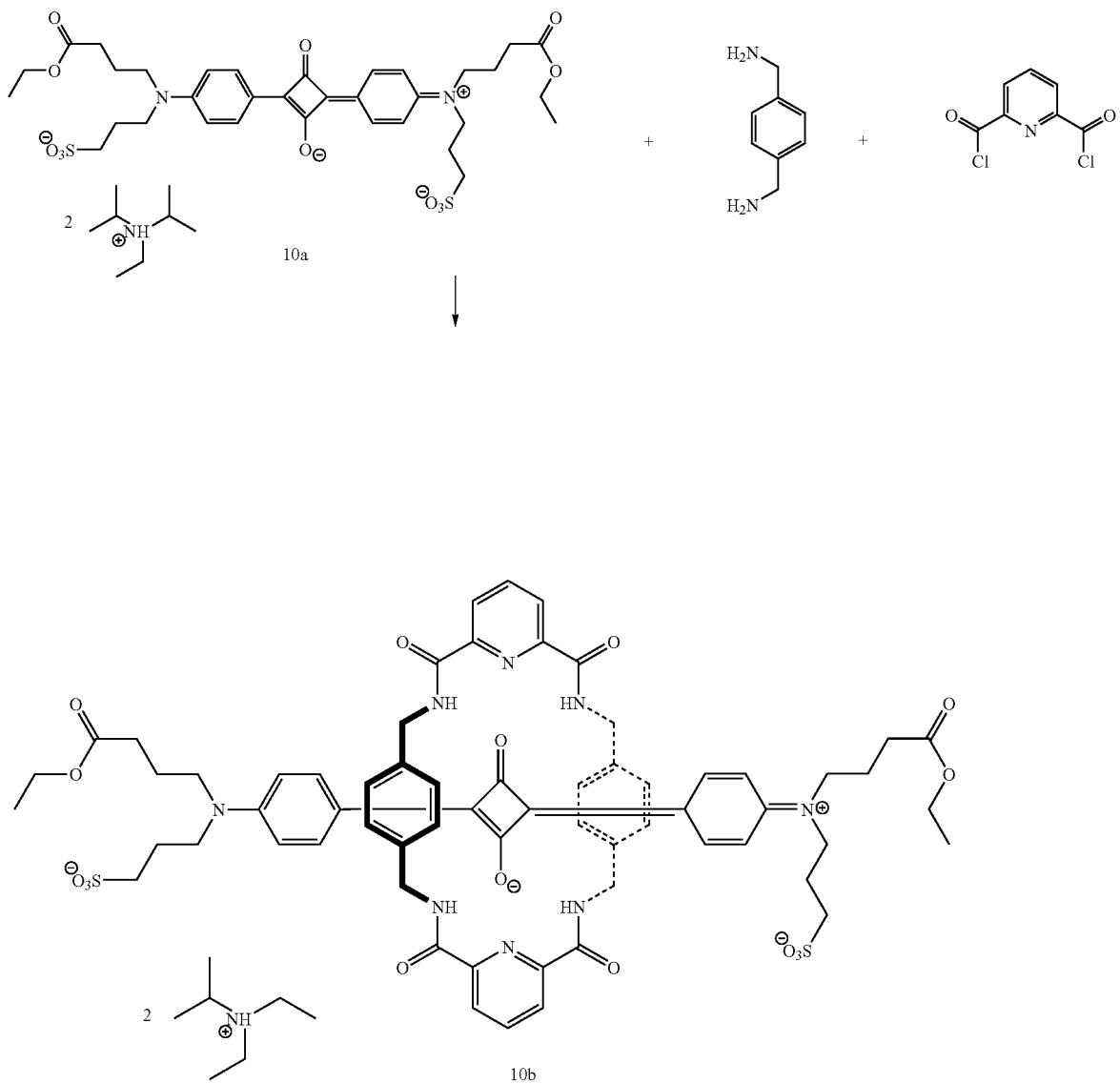

Clear solutions of 2,6-pyridinedicarbonyl dichloride (1.28 mmol) in 5 mL of chloroform and p-xylylenediamine (1.28 mmol) in 5 mL of chloroform were simultaneously added dropwise over a 5 h period to a stirred solution of 10a (200 mg, 0.32 mmol) and triethylamine (3.2 mmol) in 40 mL of CHCl$_3$. After stirring overnight, the reaction mixture was filtered to remove any polymeric materials, and the resulting crude product was column purified (RP-18, methanol/water gradient) to yield 10b. $\lambda_{max}$ (abs): 656 nm, $\lambda_{max}$ (em): 674 nm.

e) Synthesis of Squaraine-Rotaxane Dye 10
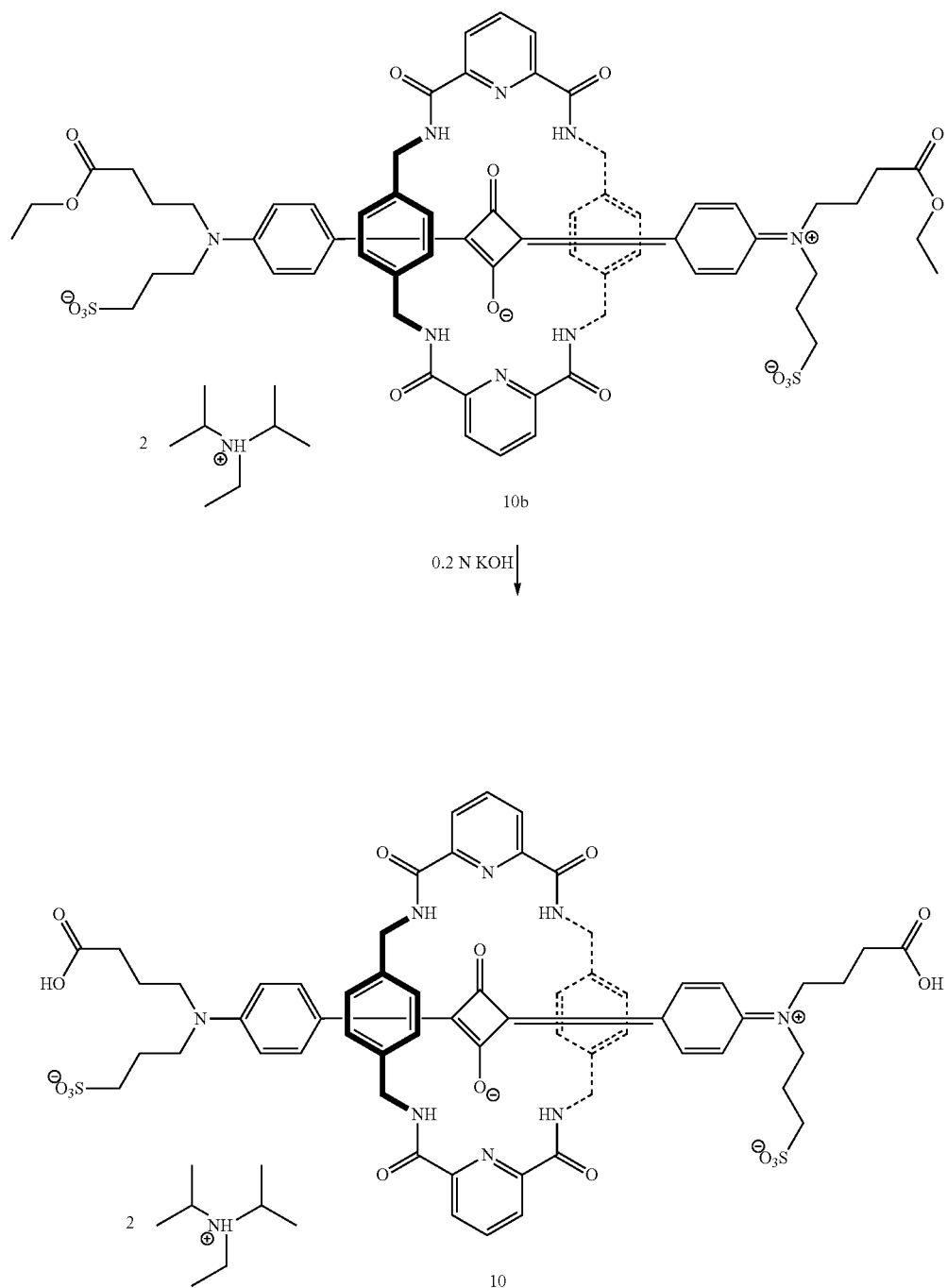
2 mmol 10b were stirred for 3 h at room temperature in 50 mL of 0.2 N aqueous solution of KOH. Than the mixture was neutralized with 0.2 N HCl and the resulting solution was column purified (RP-18; methanol/water, gradient) to yield squaraine-rotaxane, 10. $\lambda_{max}$ (abs): 655 m, $\lambda_{max}$ (em): 673 nm, Q.Y.: 25% (water).

Synthesis of the NHS Ester of Rotaxane 10

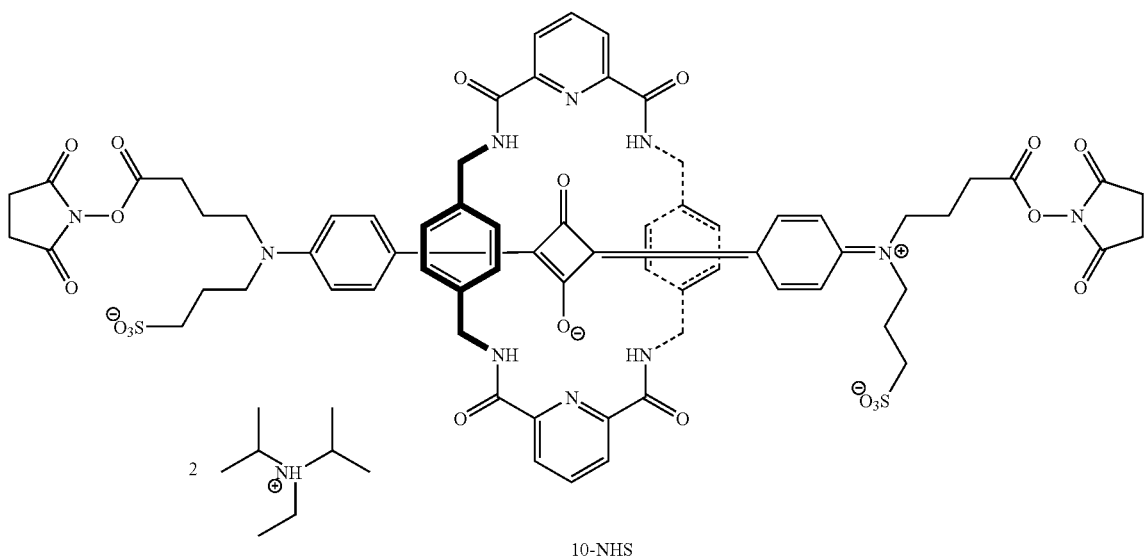

10-NHS 5.2 mg (2.97 µmol) of 10, 3.0 mg (10 µmol) of TSTU, and 13.0 mg (10 µmol) of DIPEA were dissolved in 1 mL of DMF. The solution was stirred at room temperature for 4 h to give 10-NHS. The resulted solution was used for labelling.

Example 10

Synthesis of Rotaxane 11

Synthesis of the Reactive, Symmetrical Cyanine

The synthesis of the indolenine 1m is analogous to the synthesis of 1d except that for the quarternization of the indolenine benzylbromide or p-sulfo-benzylbromide is used. The synthesis of the cyanine 11a is analogous to the synthesis described in U.S. Patent Application Publication No. US2002/0077487 A1.

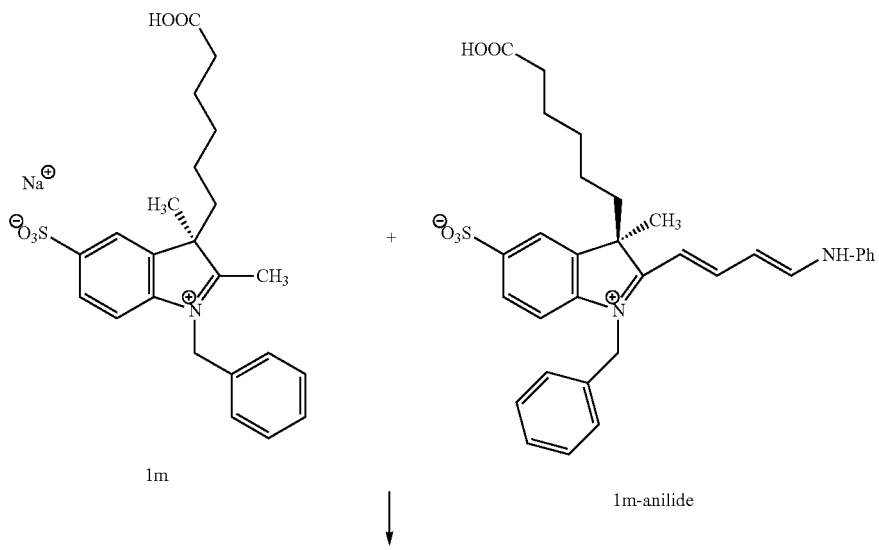

1m          1m-anilide

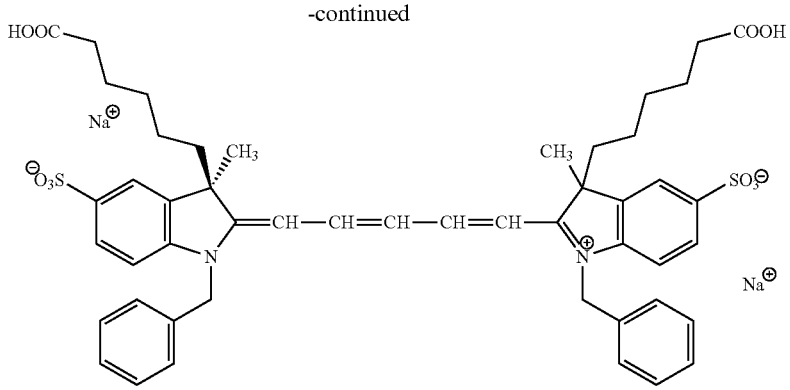

11a

Synthesis of Rotaxane 11:

2,6-pyridinedicarbonyl dichloride (0.2 mmol) and p-xylylenediamine (0.2 mmol) each dissolved in 5 mL CHCl₃ were simultaneously added dropwise over five hours to a stirred solution of 8a (0.05 mmol) and triethylamine (0.5 mmol) in 40 mL of CHCl₃/MeOH. After stirring the reaction mixture overnight, the reaction mixture was filtered, the solvent removed under reduced pressure and the resulting crude product chromatographed using a reversed-phase silica column and water/MeOH as eluent.

Example 11

Synthesis of Rotaxane 12

Synthesis of Squaraine-Rotaxane 12a:

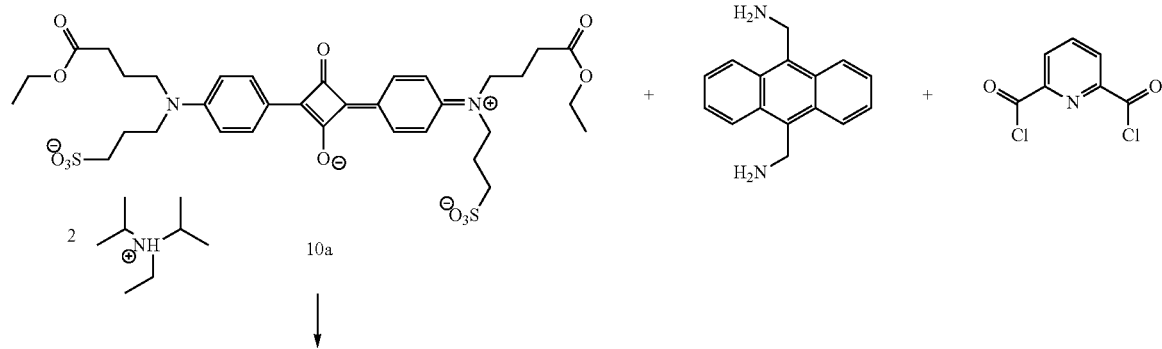

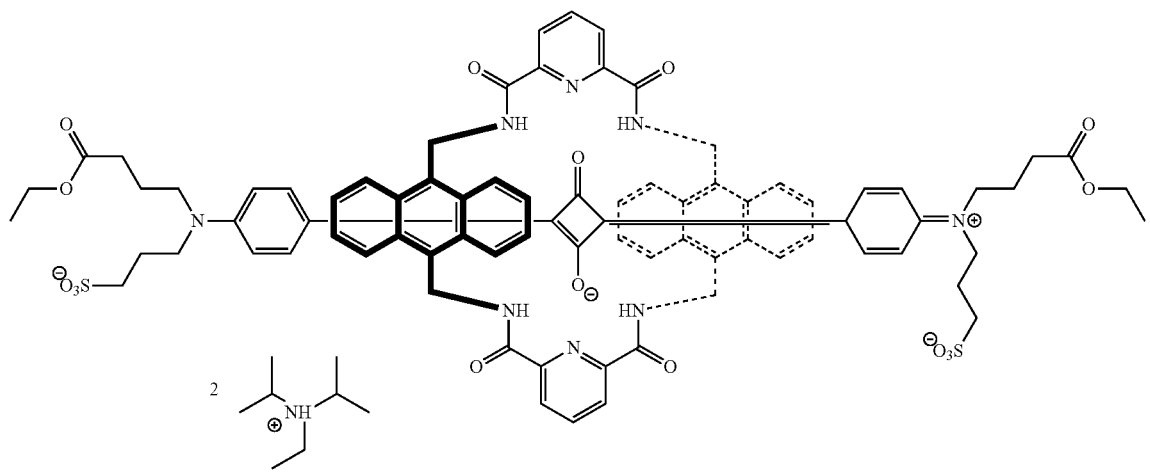

12a

Clear solutions of 2,6-pyridinedicarbonyl dichloride (112 mg, 0.55 mmol) in 20 mL of chloroform and 9,10-bis(aminomethyl)anthracene (130 mg, 0.55 mmol, synthesized according to J. J. Gassensmith et al., *J. Am. Chem., Soc.,* 2007, 129 (48), 15054-15059) in 20 mL of chloroform were simultaneously added dropwise over a 10 h period to a stirred solution of 10a (70 mg, 0.07 mmol) and triethylamine (111 mg, 1.1 mmol) in 70 mL of $CHCl_3$. After stirring overnight, the reaction mixture was filtered to remove any polymeric materials, and the resulting crude product was column purified (RP-18, methanol/water gradient) to yield 12a.

Synthesis of Squaraine-Rotaxane Dye 12:

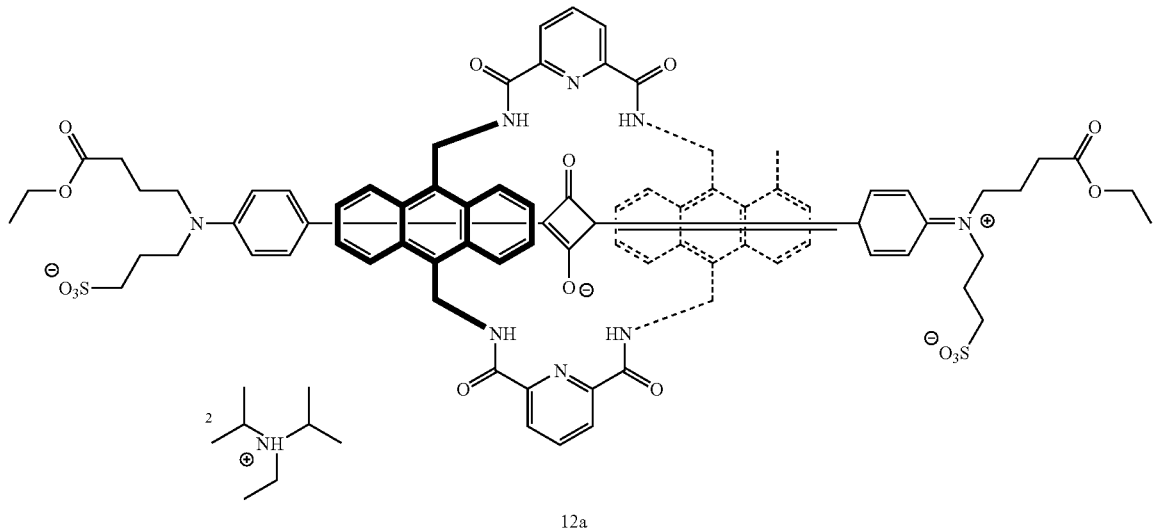

12a

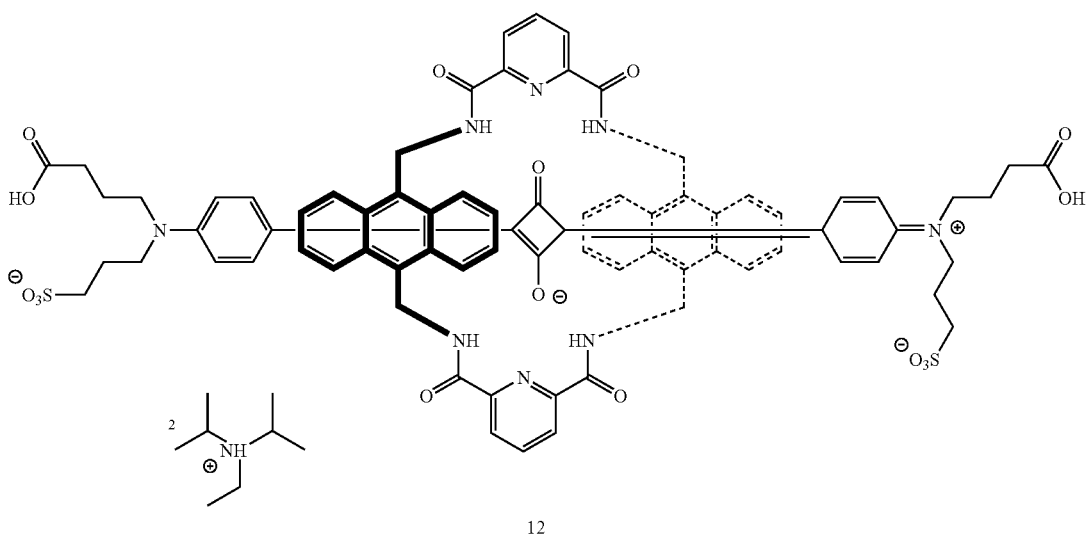

12

2 mmol 12a were stirred for 3 h at room temperature in 50 mL of 0.2 N aqueous solution of NaOH. Than the mixture was neutralized with 0.2 N HCl and the precipitate was filtered and washed successively with water, ether and chloroform. Deep purple solid was dissolved in 20 ml water consist 0.1% DIPEA and column purified (RP-18; methanol/water, gradient) to yield squaraine-rotaxane 12. $\lambda_{max}$(abs): 666 nm, $\lambda_{max}$ (em): 716 nm, Q.Y.: 60% (water).

Synthesis of the NHS Ester of Rotaxane 12
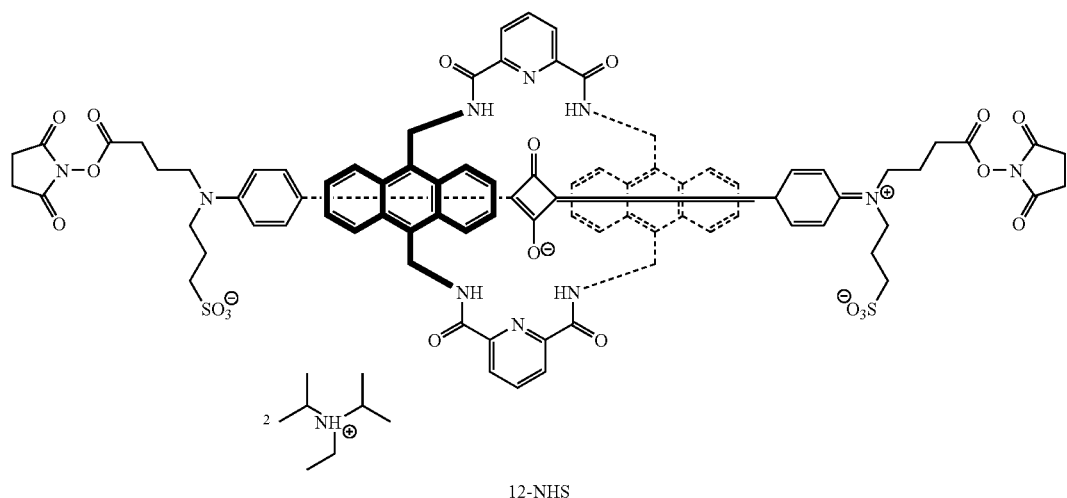
12-NHS
17.5 mg (11.63 μmol) of 1b, 10.5 mg (35 μmol) of TSTU, and 46.0 mg (35.5 μmol) of DIPEA were dissolved in 3 mL of DMF. The solution was stirred at room temperature for 1.5 h to give 1b-NHS. The resulting solution was used for labelling.
Example 12
Synthesis of the Hydrophobic Anthracene Rotaxane 13
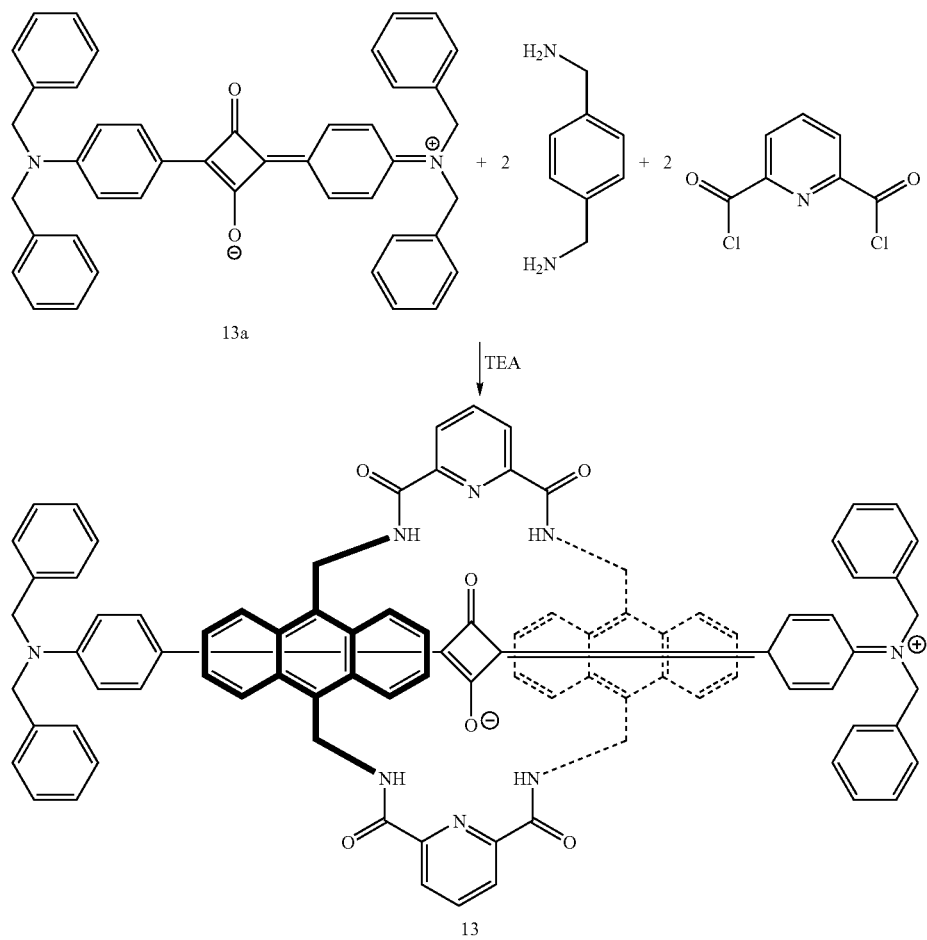
13

Clear solutions of 2,6-pyridinedicarbonyl dichloride (84 mg, 0.41 mmol) in 15 mL of chloroform and 9,10-bis(aminomethyl)anthracene (97 mg, 0.41 mmol) in 15 mL of chloroform were simultaneously added dropwise over 10 h to a stirred solution of squaraine 13a (32 mg, 0.05 mmol, synthesized according to E. Arunkumar et al. Chem. Eur. J. 2006, 12, 4884-4690) and triethylamine (81 mg, 0.8 mmol) in 30 mL of chloroform. After overnight stirring, the mixture containing rotaxane 13 and polymer co-products was filtered, washed with chloroform (100 mL) to extract rotaxane 13, and the filtrate was concentrated. Purification of the crude material by column chromatography using silica gel (gradient, 0-1% of MeOH in CHCl$_3$) gave the rotaxane 13. $\lambda_{max}$ (abs): 651 m, $\lambda_{max}$ (em): 707 nm, 59% (methanol); $\lambda_{max}$ (abs): 648 nm, $\lambda_{max}$ (em): 700 nm, Q.Y.: 65% (chloroform).

Example 13

Synthesis of the Hydrophobic Durene Rotaxane 14

Synthesis of intermediate 4-aminomethyl-2,3,5,6-tetramethyl phenylmethanamine

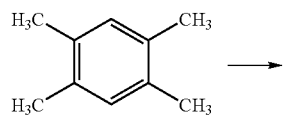

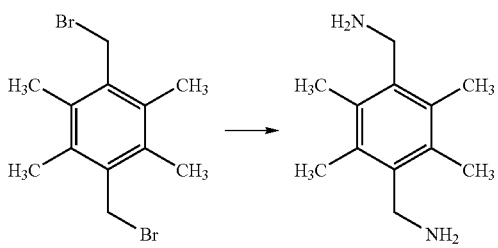

1,4-di(bromomethyl)-2,3,5,6-tetramethyl benzene was synthesized according to J. Org. Chem., 1993, 58(5), 1262-1263. 4-aminomethyl-2,3,5,6-tetramethyl phenylmethanamine was synthesized starting from 1,4-di(bromomethyl)-2,3,5,6-tetramethylbenzene alogously to the method described in J. Am. Chem. Soc., 2007, 129, 15054-15059.

Figure 11:
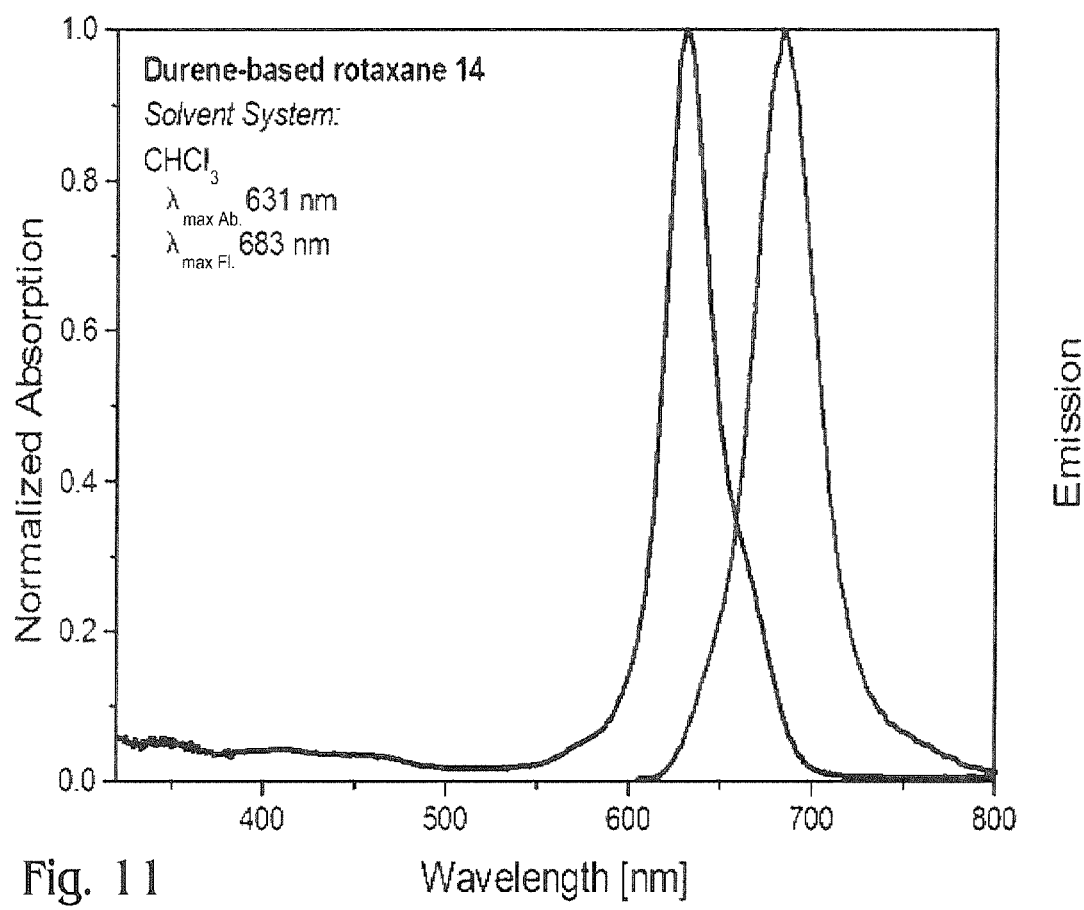
FIG. 11. A plot showing the absorption and emission spectrum of the durene-based rotaxane 14 (Example 13) with very narrow excitation and emission band widths at half-max of 30 and 40 nm in $CHCl_3$, respectively.
Figure 12:
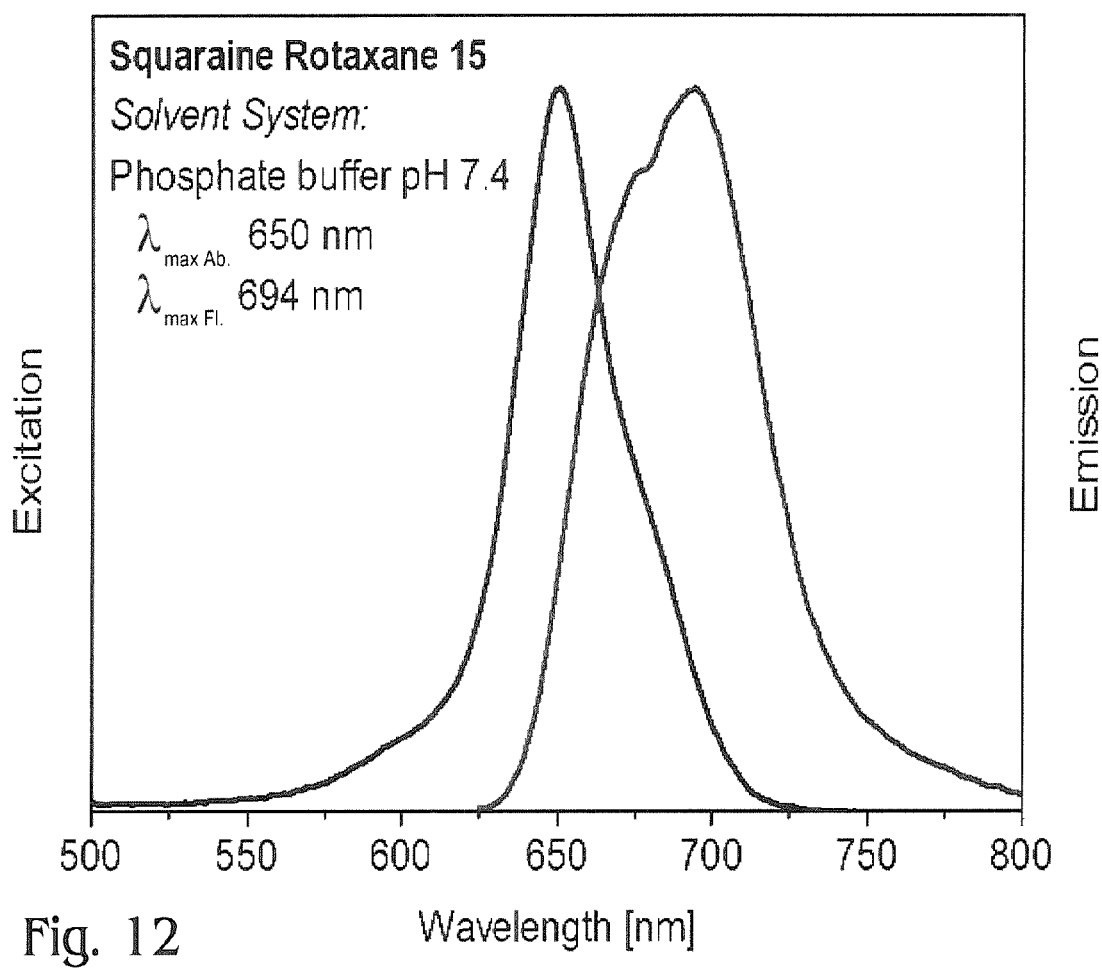
FIG. 12. A plot showing the excitation and emission spectrum of the durene-based rotaxane 15 (Example 14).

Synthesis of Squaraine-Rotaxane 14:

The squaraine-rotaxane 14 was synthesized analogously to Example 12, but instead of 9,10-bis(aminomethyl)anthracene, 4-aminomethyl-2,3,5,6-tetramethylphenylmethanamine was used. $\lambda_{max}$ (abs): 631 nm, $\lambda_{max}$ (em): 683 nm; $\tau_1$=2.92 ns (100%) (chloroform). The rotaxane 14 shows very narrow emission band with at half-max of about only 40 nm (FIG. 11).

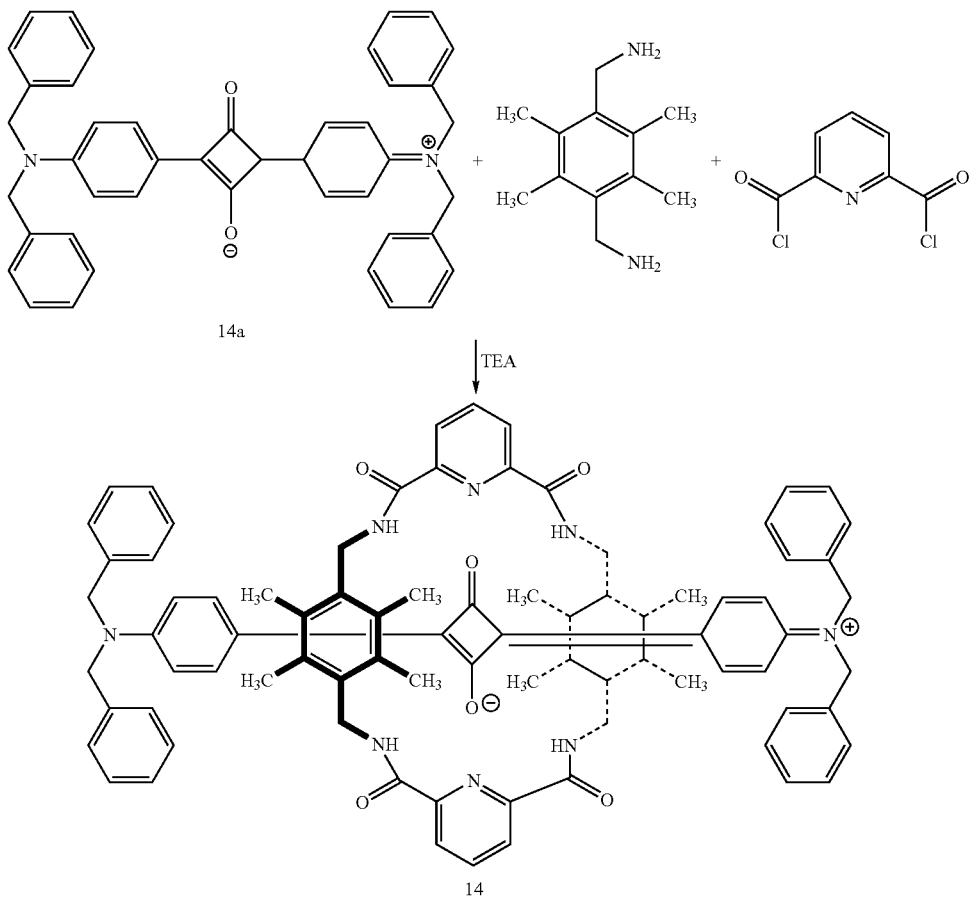

Example 14

Synthesis of the Hydrophilic Durene-Based Rotaxane 15

Synthesis of Squaraine-Rotaxane 15a:

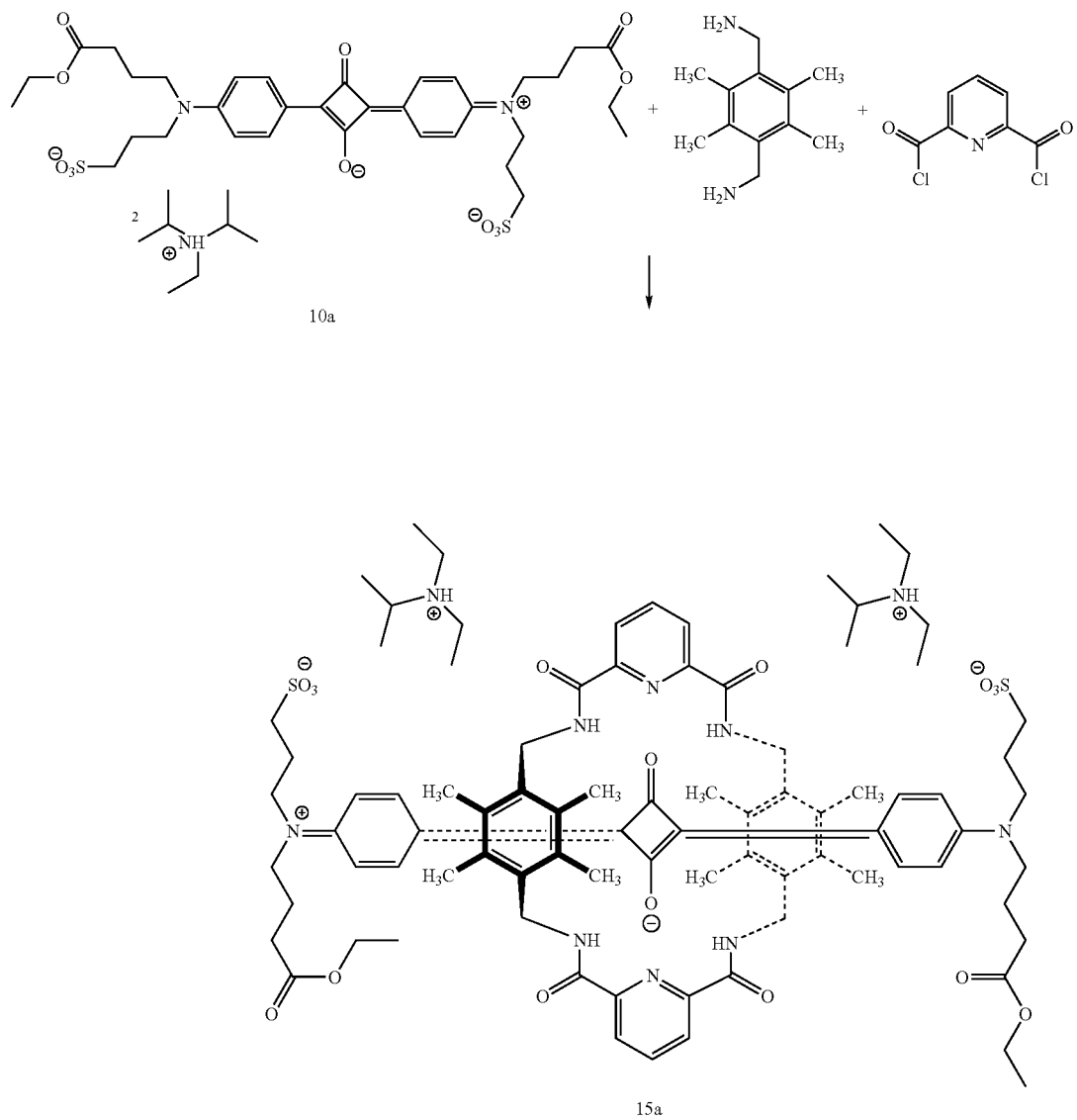

Clear solutions of 2,6-pyridinedicarbonyl dichloride (66 mg, 0.32 mmol) in 15 mL of chloroform and 4-aminomethyl-2,3,5,6-tetramethyl phenylmethanamine (62 mg, 0.32 mmol in 15 mL of chloroform were simultaneously added dropwise over a 8 h period to a stirred solution of 10a (80 mg, 0.08 mmol) and triethylamine (81 mg, 0.8 mmol) in 70 mL of $CHCl_3$. After stirring overnight, the reaction mixture was filtered to remove any polymeric materials, and the resulting crude product was column purified (RP-18, methanol/water gradient) to yield 15a.

Synthesis of Squaraine-Rotaxane Dye 15:

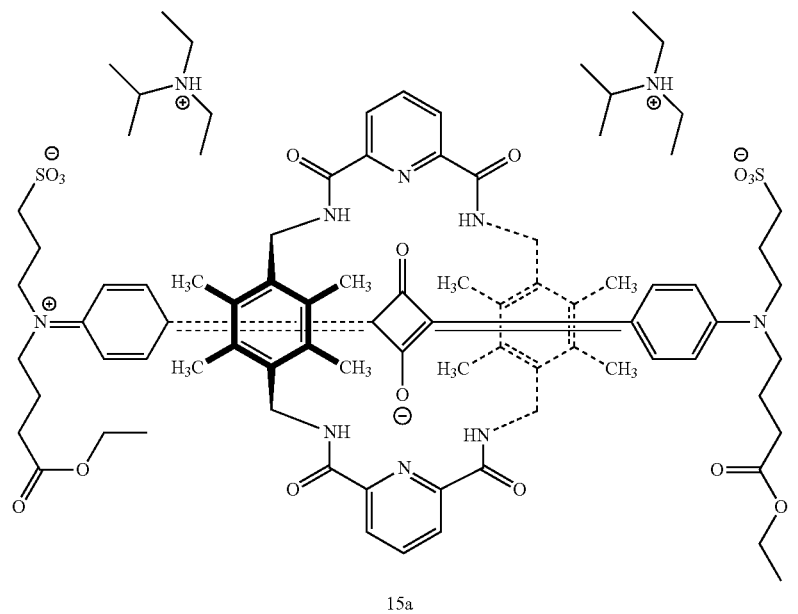

15a 0.2 N NaOH

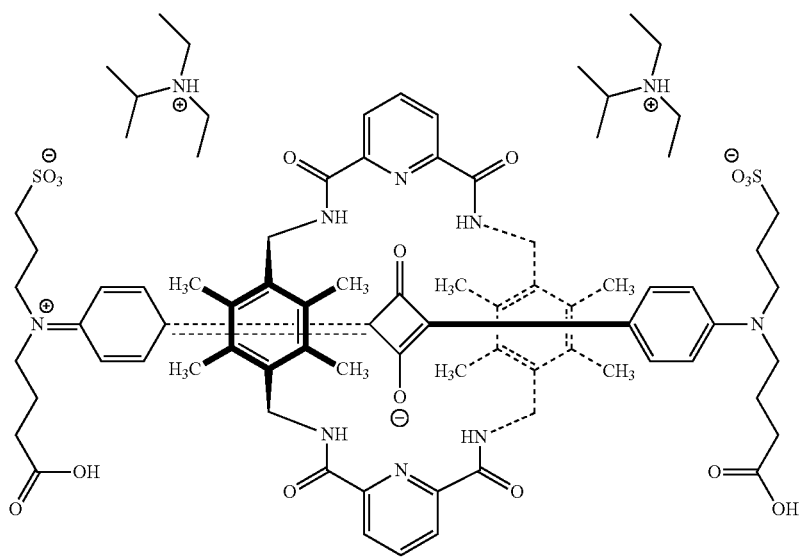

15

2 mmol of 15a were stirred at 80° C. for 3 h in 50 mL of 0.2 N aqueous solution of NaOH. Than the mixture was neutralized with 0.2 N HCl and the precipitate was filtered and washed successively with acetonitrile and ether. Deep green solid was dissolved in 20 mL water with 0.1% DIPEA and column purified (RP-18; methanol/water, gradient) to yield squaraine-rotaxane 15. $\lambda_{max}$ (abs): 650 nm, $\epsilon$=368,000 $M^{-1}$ $cm^{-1}$, $\lambda_{max}$ (em): 694 nm, Q.Y.: 61% (water).

Synthesis of the NHS Ester of Rotaxane 15
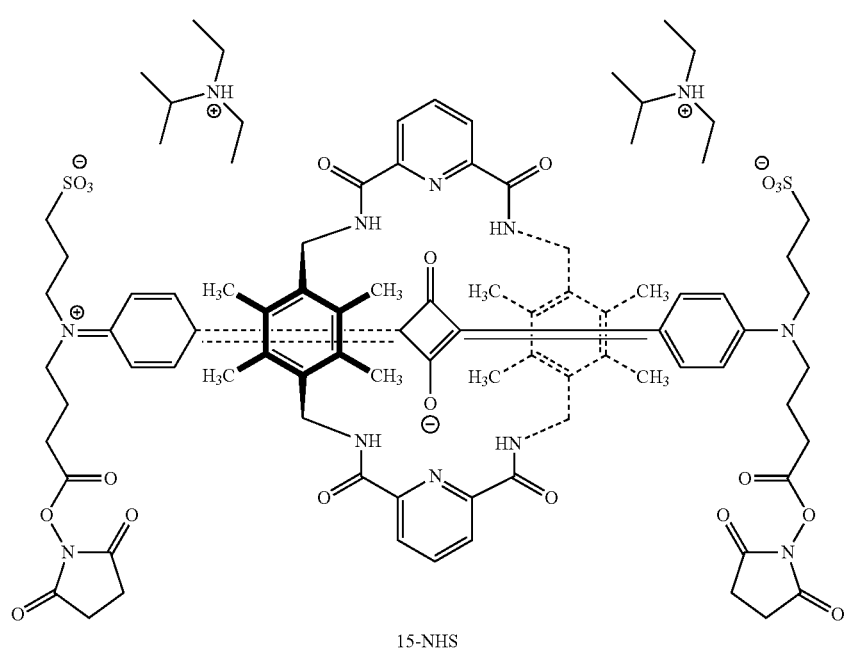
15-NHS
2 mg (1.28 µmol) of 15, 1.17 mg (3.9 µmol) of TSTU, and 6.7 mg (5.2 µmol) of DIPEA were dissolved in 5 mL of DMF. The mixture was stirred at room temperature for 5 h to give 15-NHS. The resulting solution was used for labelling.
Example 15
Examples of Novel Macrocyclic Structures
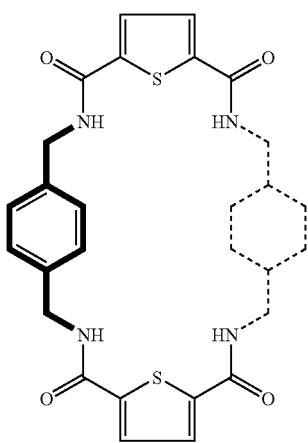
-continued
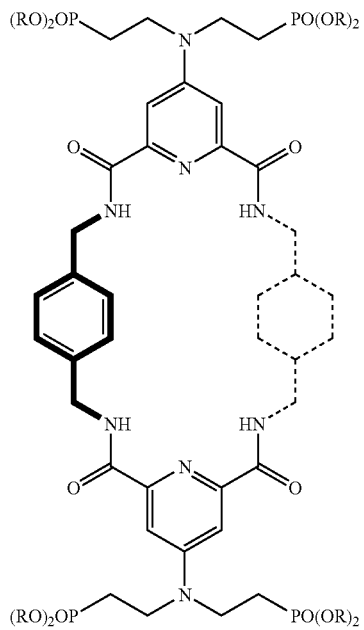

93
-continued
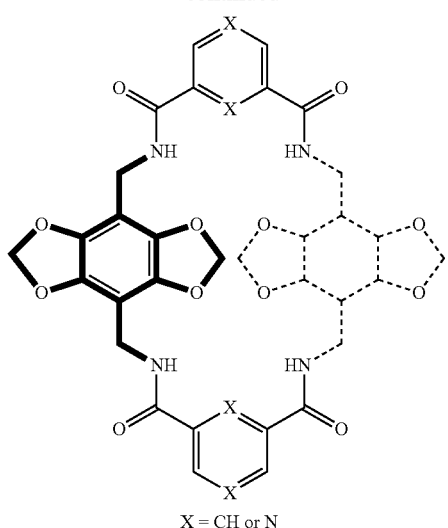
X = CH or N
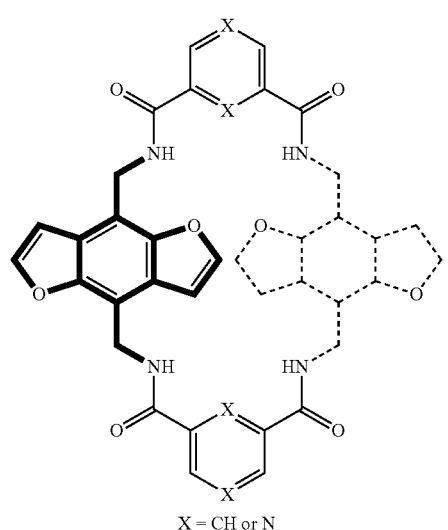
X = CH or N
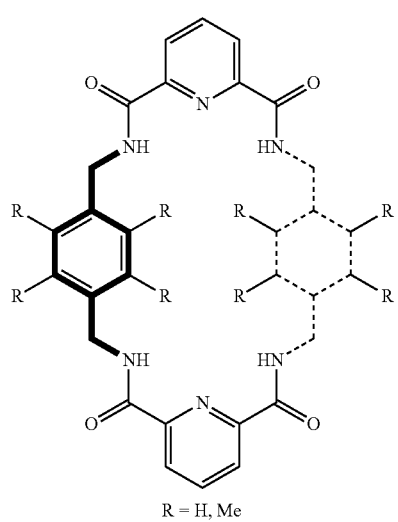
R = H, Me
94
-continued
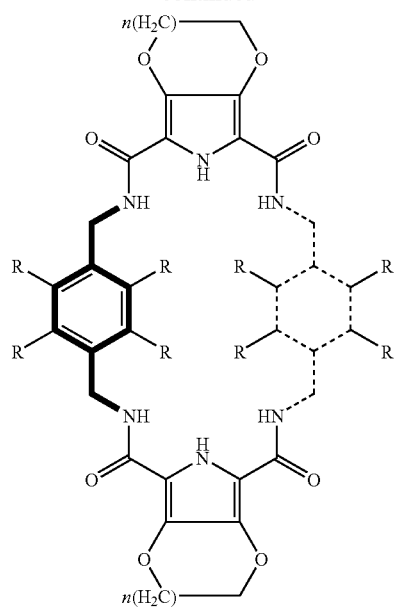
R = H, Me
n = 1, 2, 3
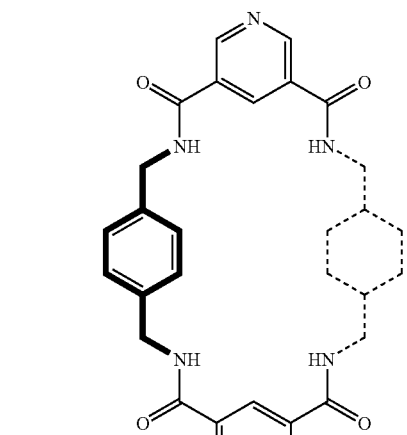
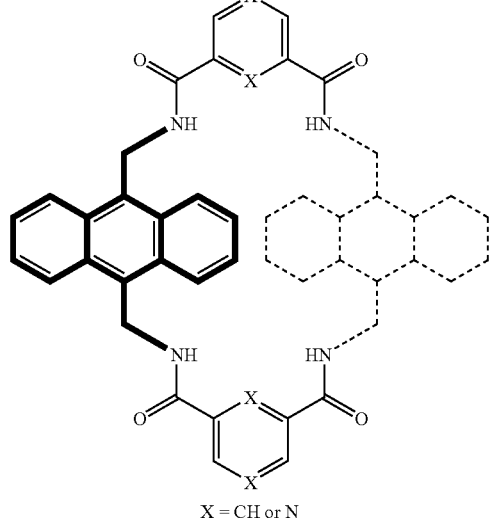
X = CH or N

95
-continued
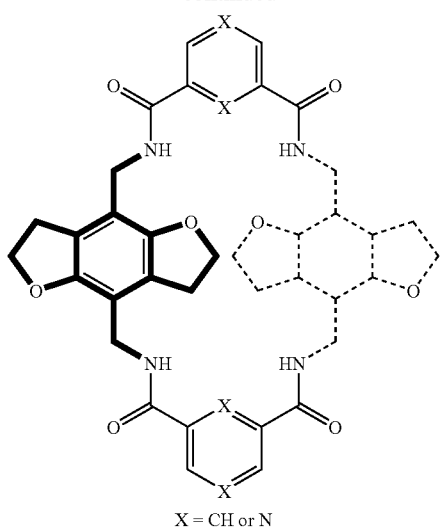
X = CH or N
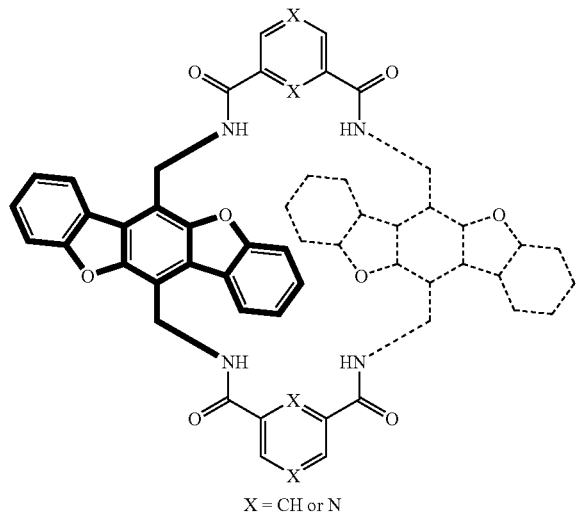
X = CH or N
96
-continued
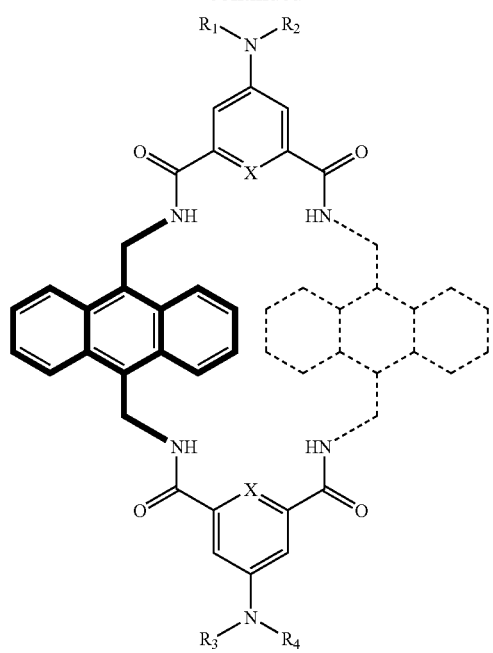
X = CH or N
$R_1, R_2, R_3, R_4$ are independently
—$(CH_2)_n$—R,
R = $CH_3$, COOH, COONHS, $SO_3H$,
—$PO(OH)_2$, —$PO(OAlk)_2$
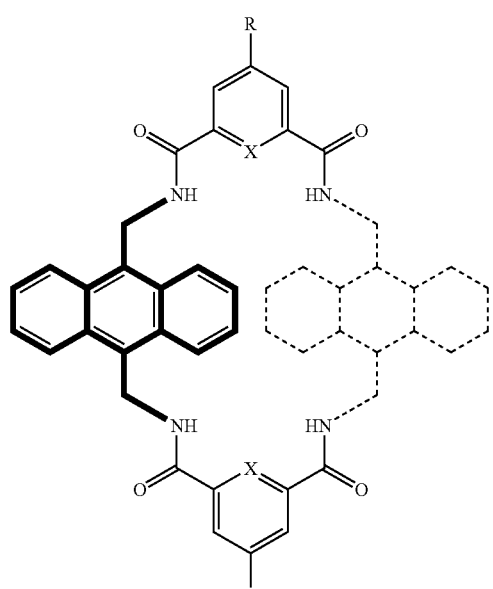
X = CH or N
R or R' is —$(CH_2)_n$—$CH_3$, OH,
—O—$(CH_2)_n$—$CH_3$,
—$(CH_2)_n$—COOH 97
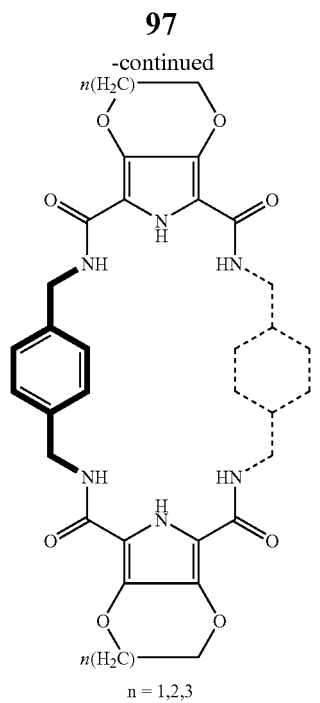
n = 1,2,3
98
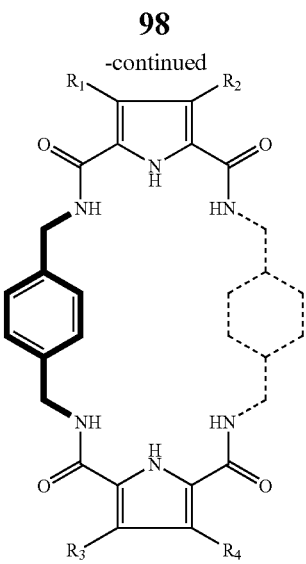
$R_1, R_2, R_3, R_4$ are independently ——$(CH_2)_n$—R,
R = $CH_3$, COOH, COONHS, SO3H,
——$PO(OH)_2$, ——$PO(OAlk)_2$
Example 16
Examples of Representative Rotaxane Structures
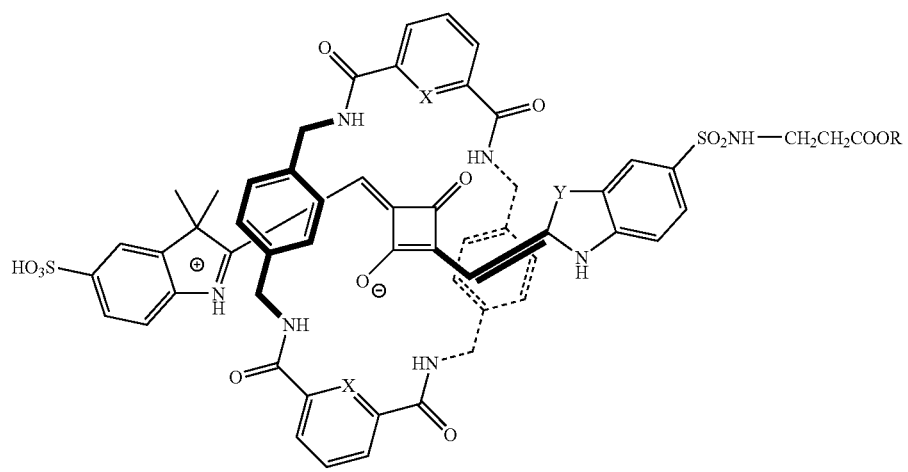
Y = N, CH
Y = $CMe_2$, O, S, Se
R = H, NHS
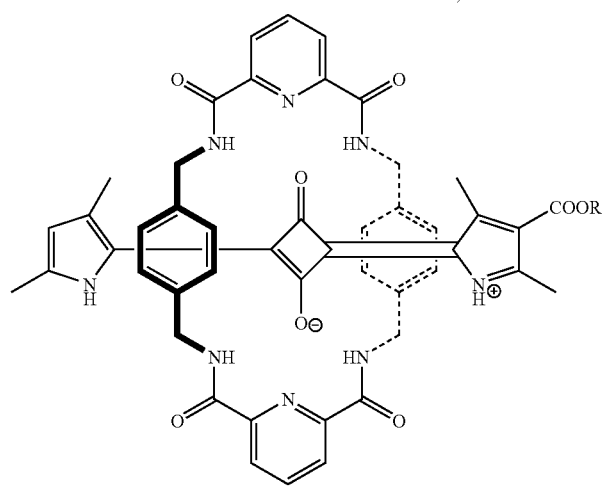
R = H, ——NHS, ——NH—$CH_2CH_2$-maleimide

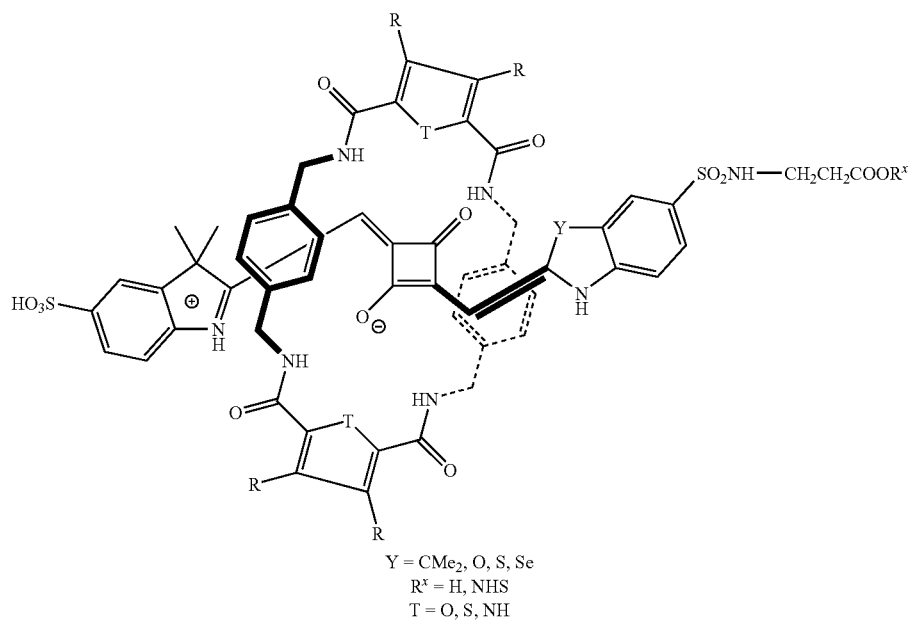
Y = CMe₂, O, S, Se
R$^x$ = H, NHS
T = O, S, NH
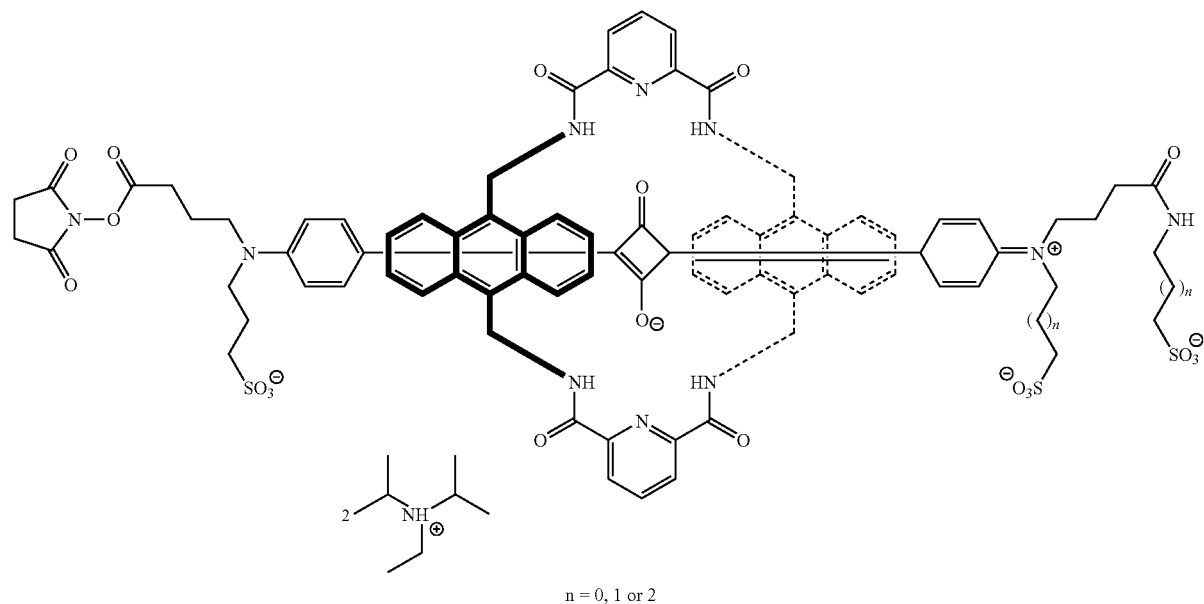
n = 0, 1 or 2

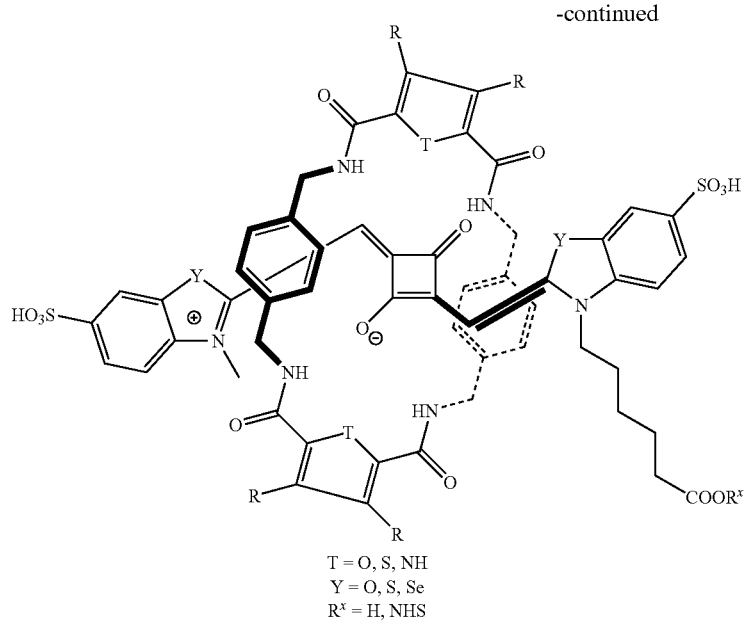
T = O, S, NH
Y = O, S, Se
R^x = H, NHS
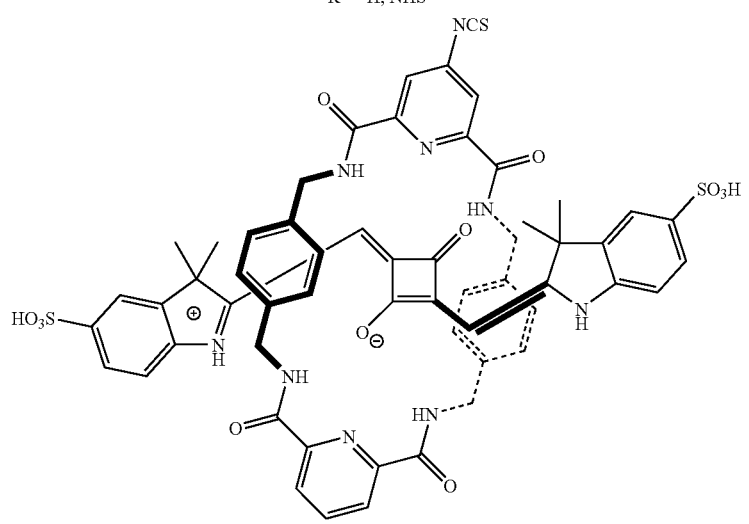
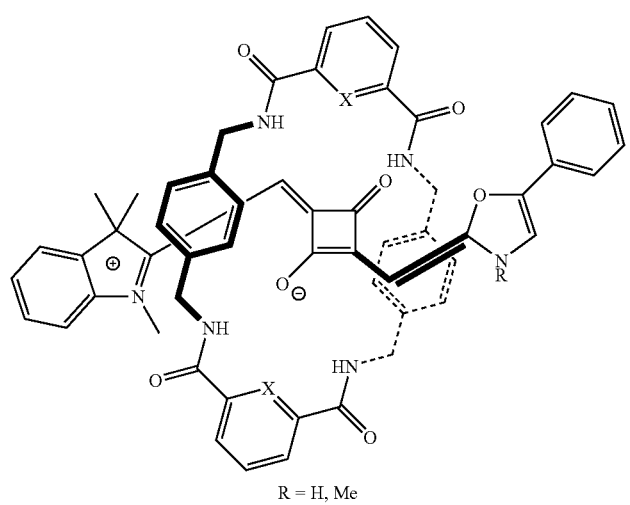
R = H, Me -continued
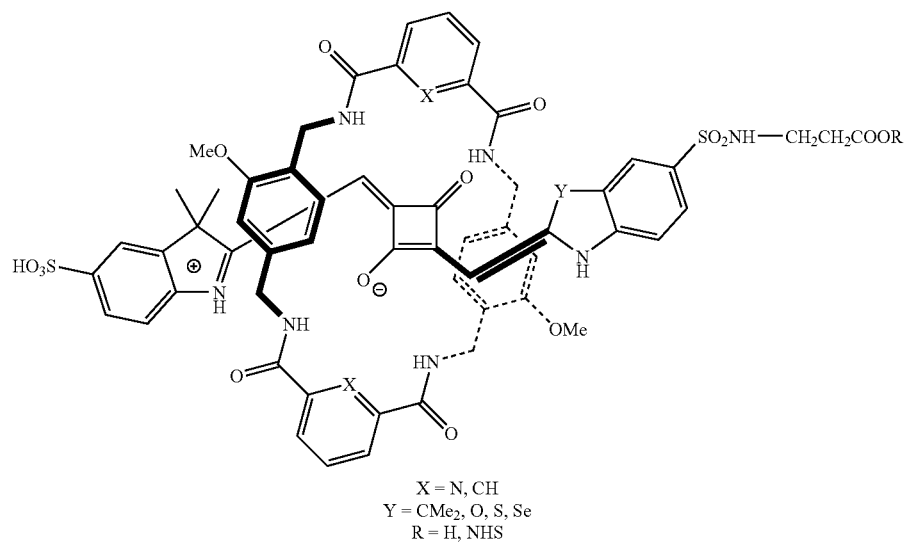
X = N, CH
Y = CMe₂, O, S, Se
R = H, NHS
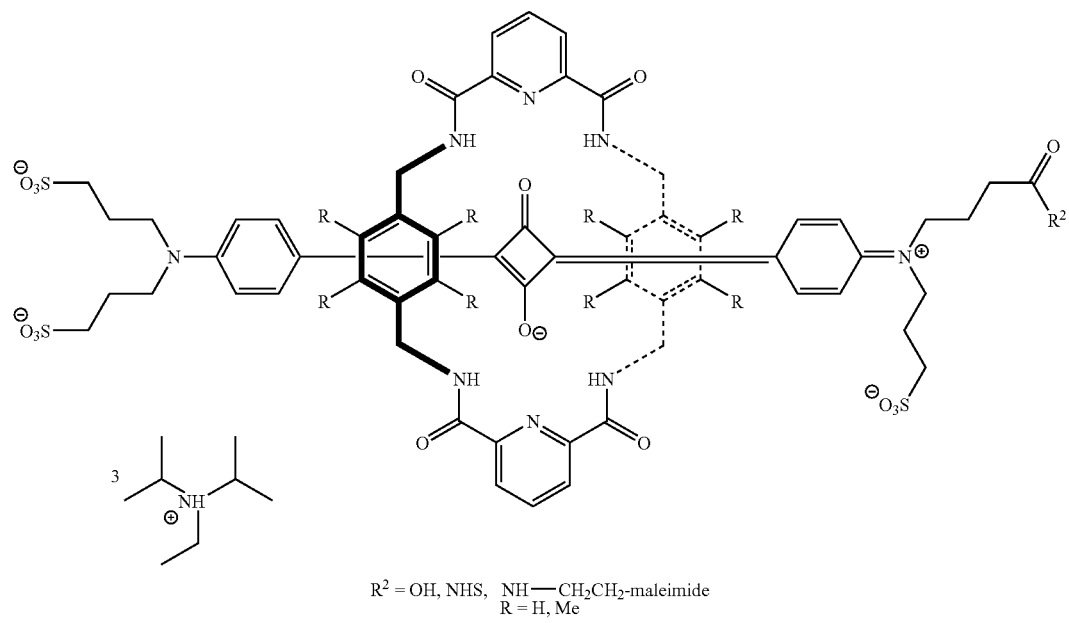
R² = OH, NHS, NH—CH₂CH₂-maleimide
R = H, Me

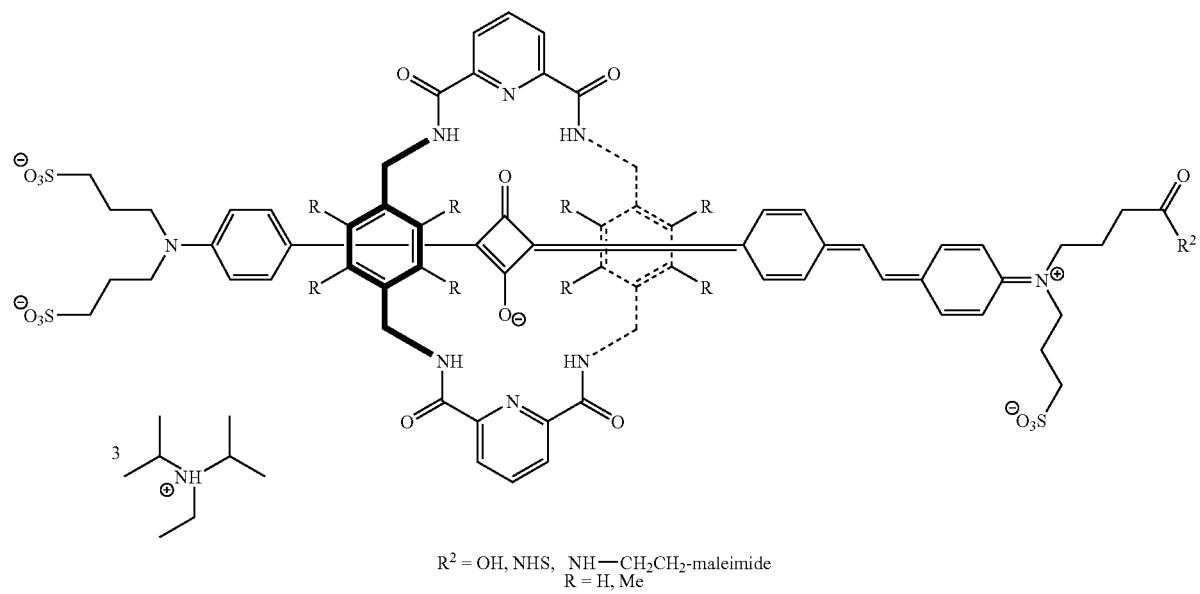
$R^2$ = OH, NHS, NH—CH$_2$CH$_2$-maleimide
R = H, Me
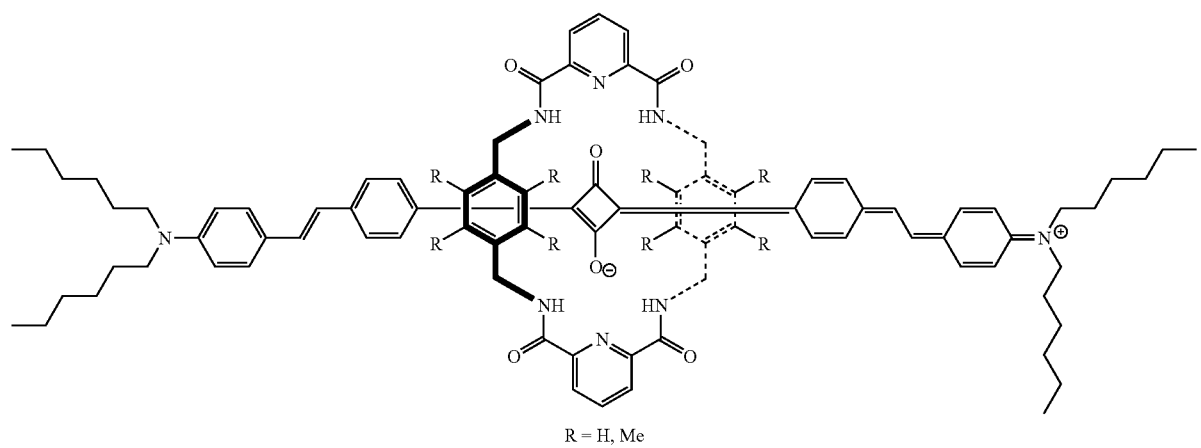
R = H, Me

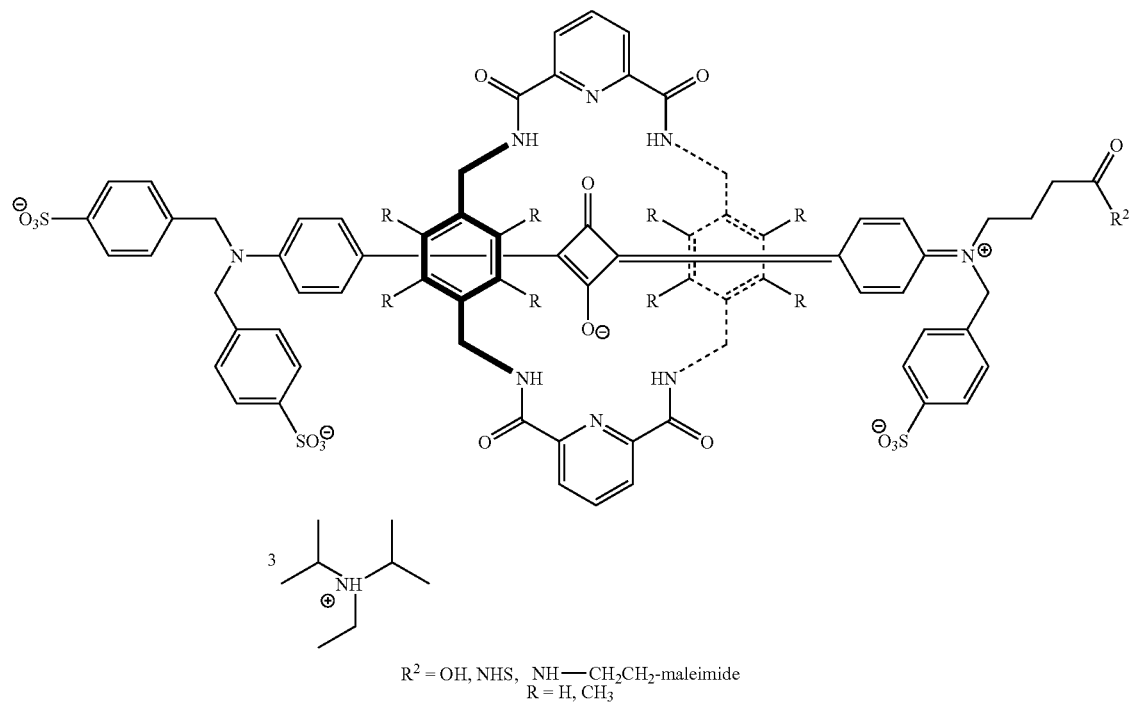
R² = OH, NHS, NH—CH₂CH₂-maleimide
R = H, CH₃
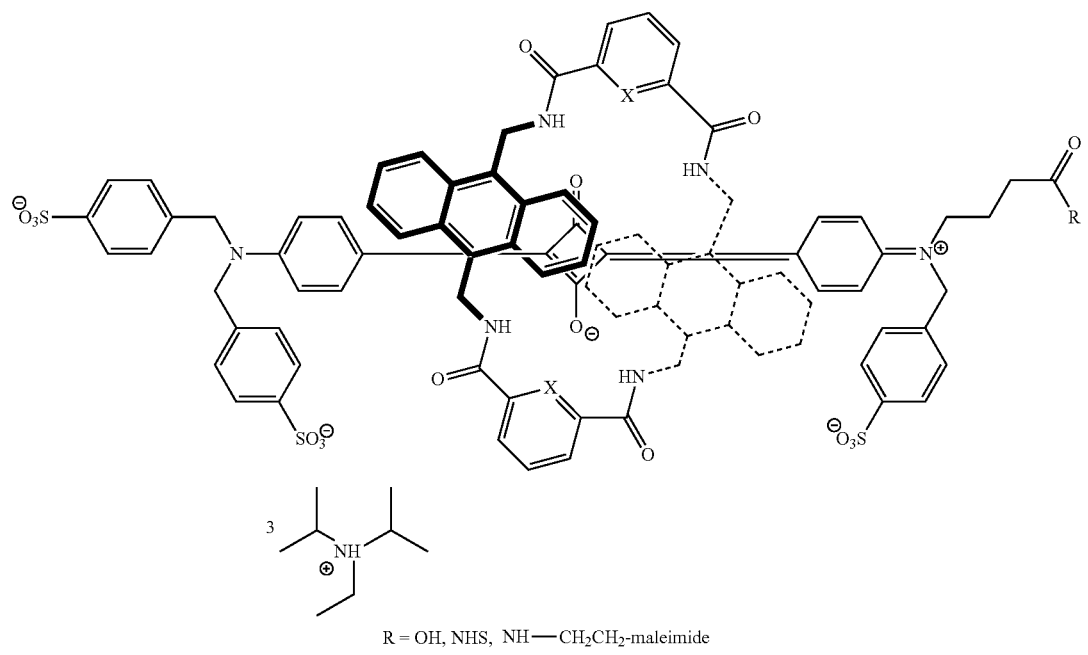
R = OH, NHS, NH—CH₂CH₂-maleimide -continued
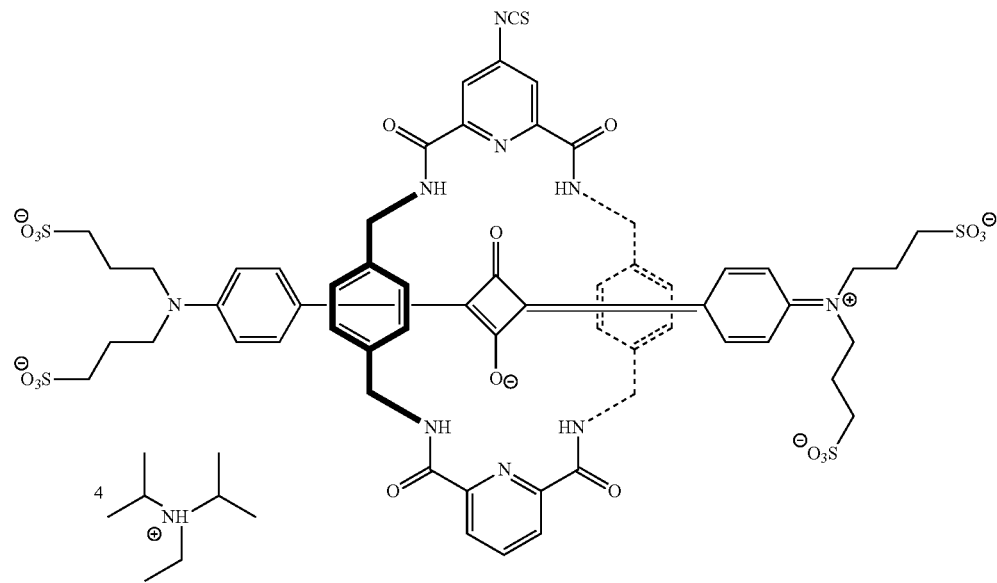
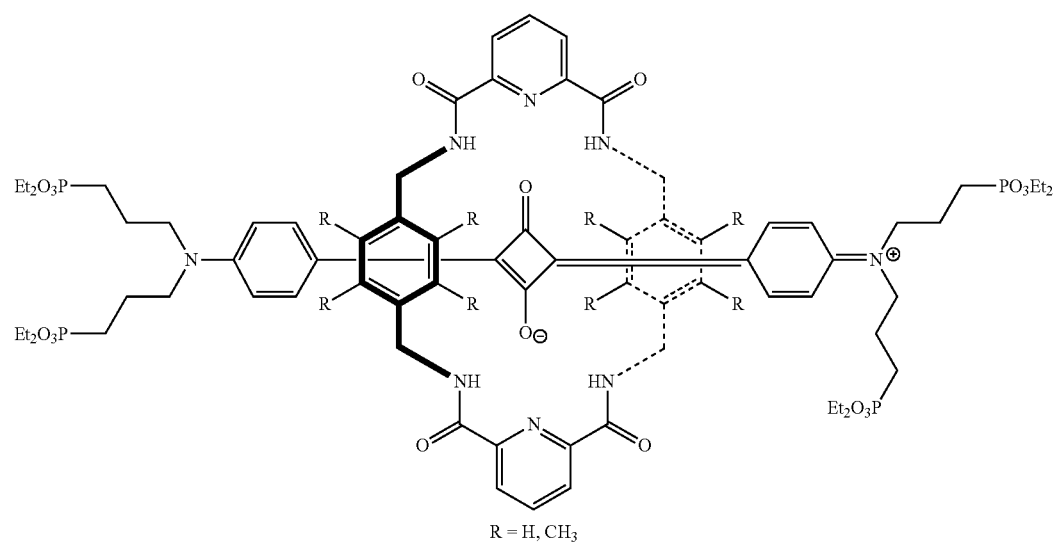
R = H, CH₃

-continued
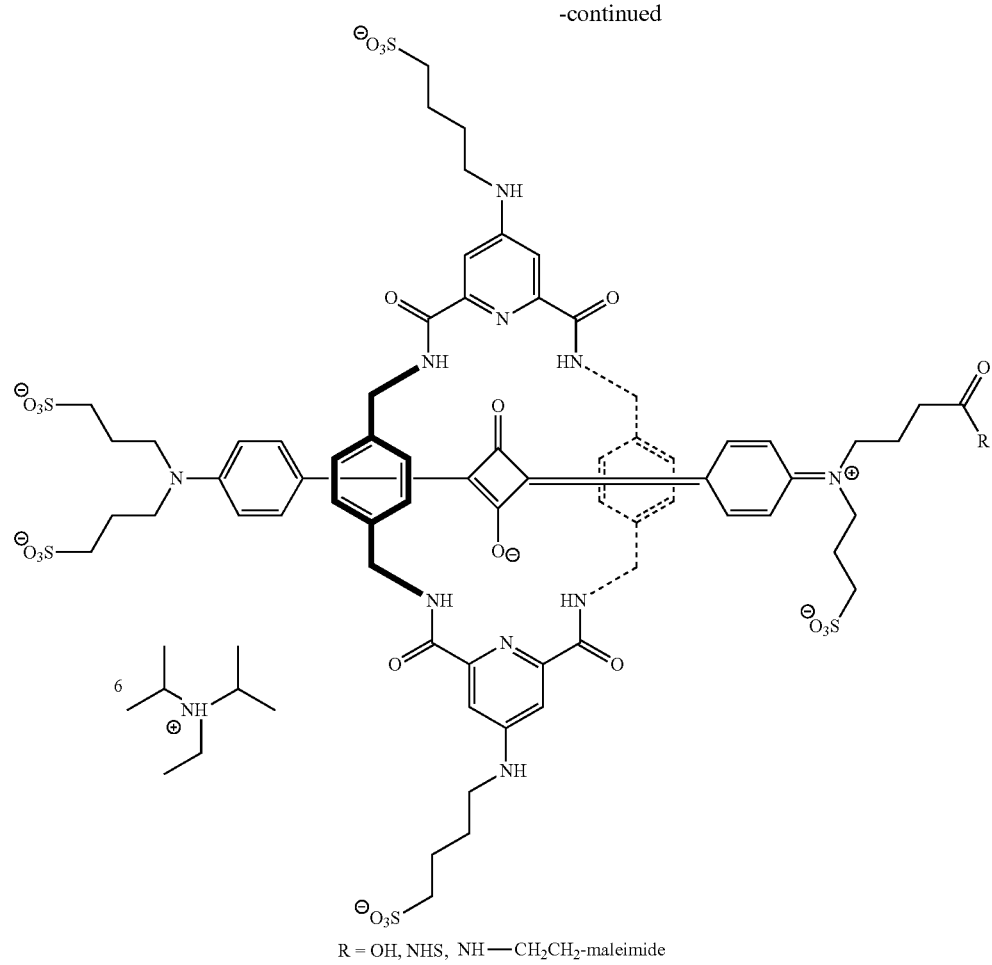
R = OH, NHS, NH—CH₂CH₂-maleimide
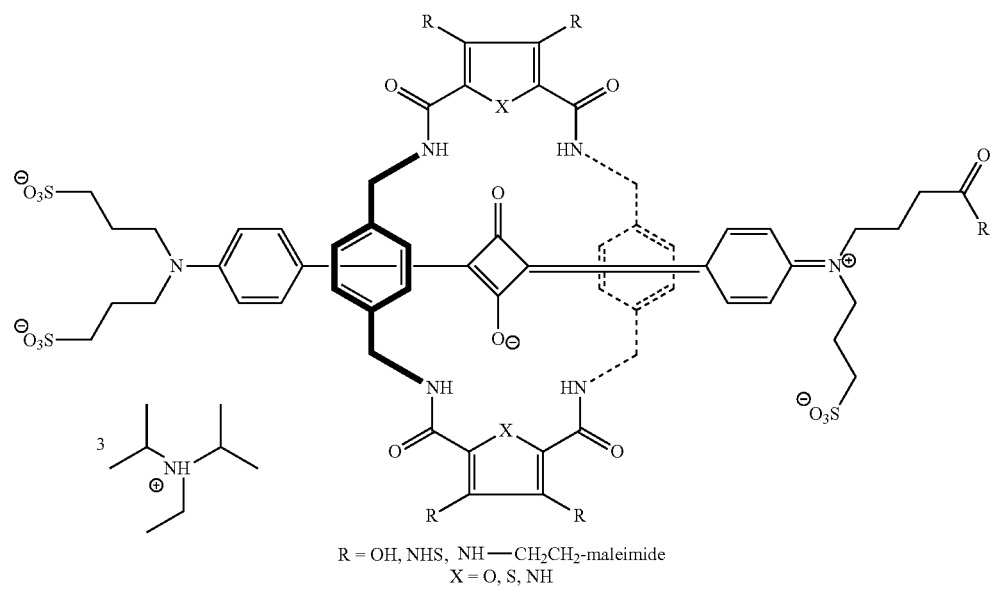
R = OH, NHS, NH—CH₂CH₂-maleimide
X = O, S, NH

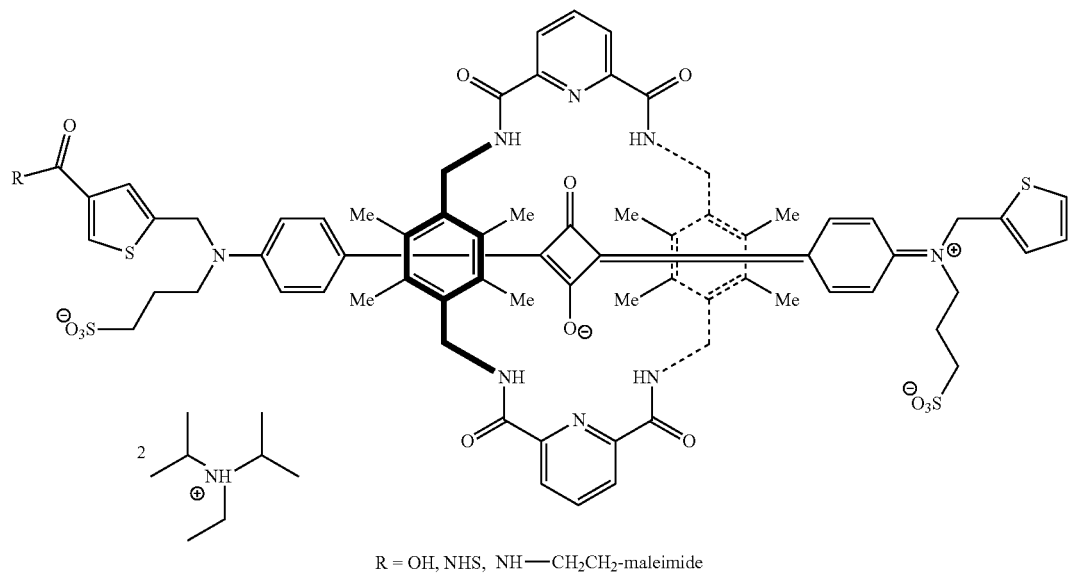
R = OH, NHS, NH—CH₂CH₂-maleimide
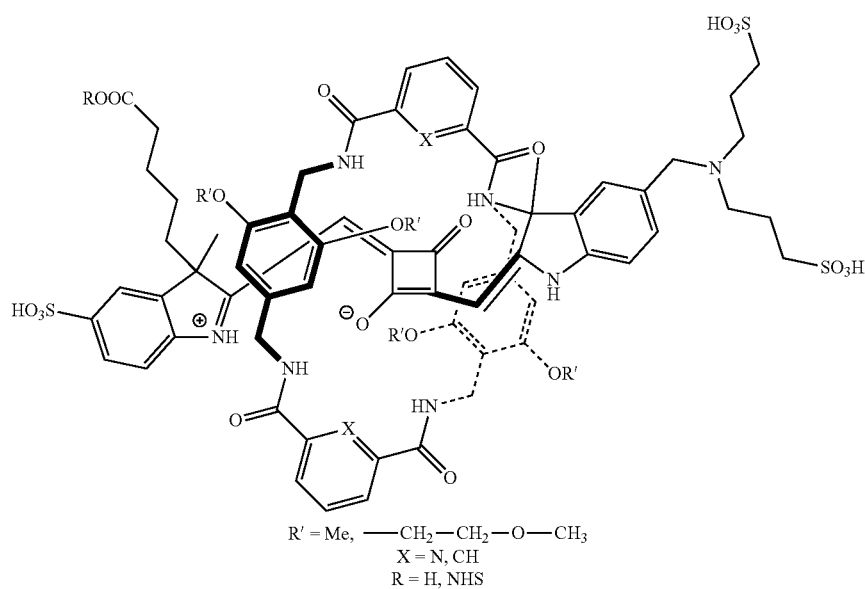
R' = Me, —CH₂—CH₂—O—CH₃
X = N, CH
R = H, NHS

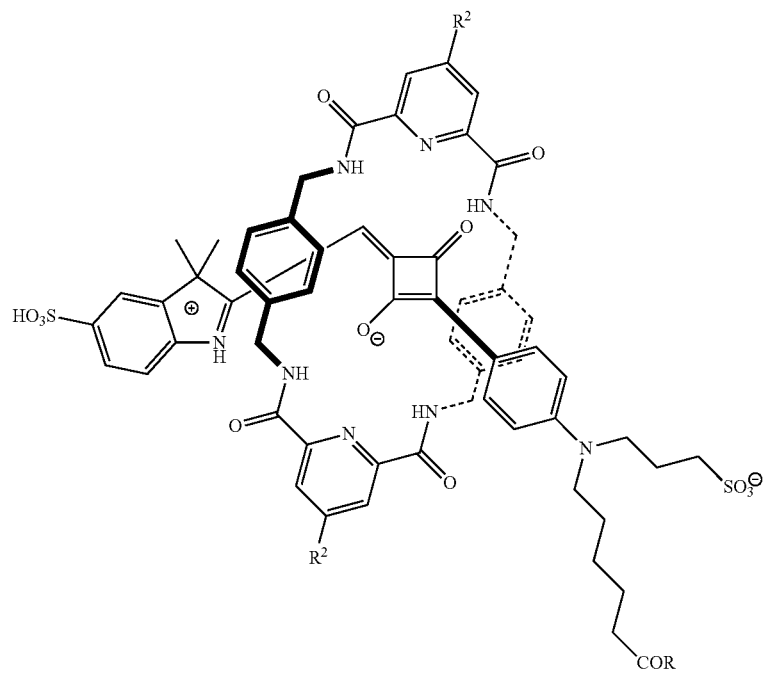
R = OH, NHS, NH—CH$_2$CH$_2$-maleimide
R$^2$ = OMe, Cl, NO$_2$
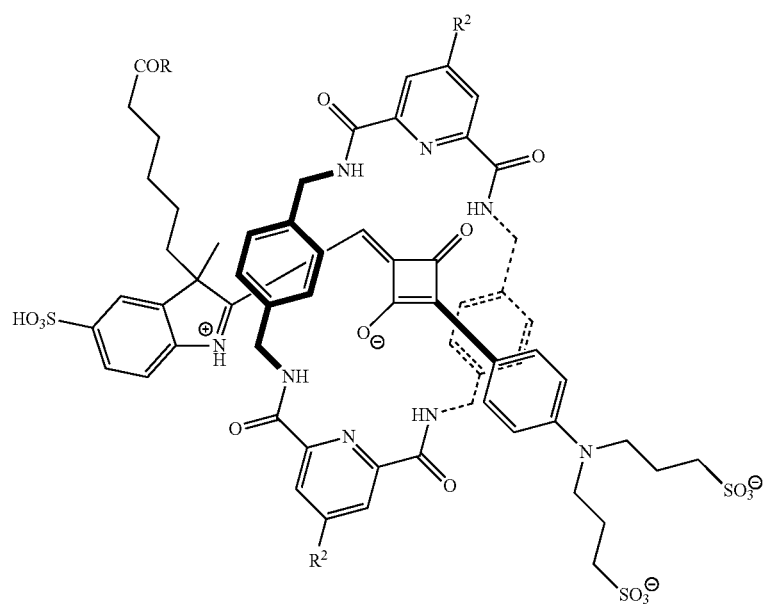
R = OH, NHS, NH—CH$_2$CH$_2$-maleimide
R$^2$ = OMe, Cl, NO$_2$

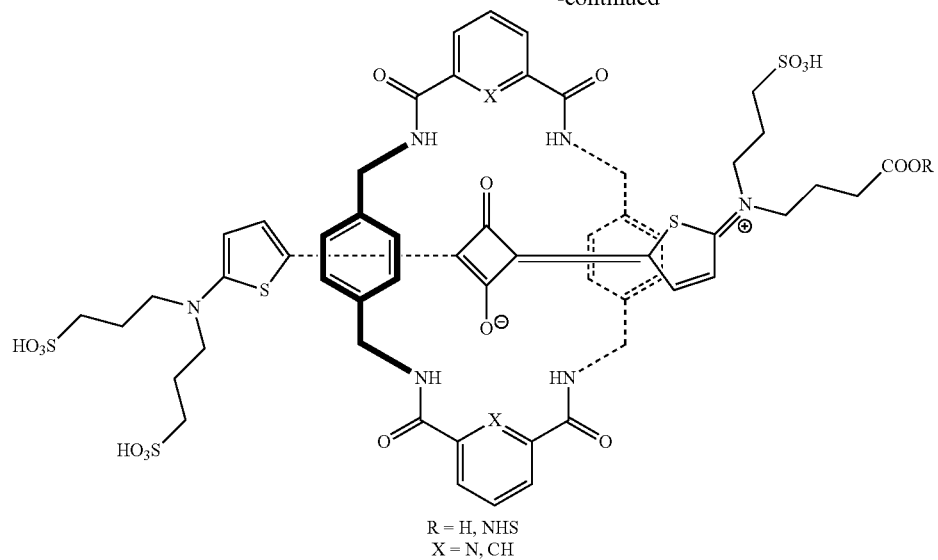
R = H, NHS
X = N, CH
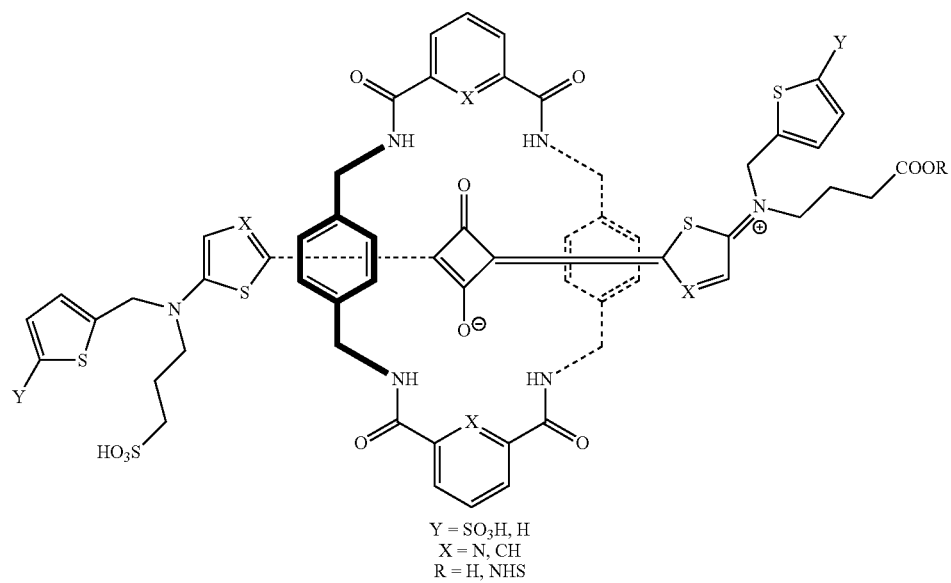
Y = SO₃H, H
X = N, CH
R = H, NHS
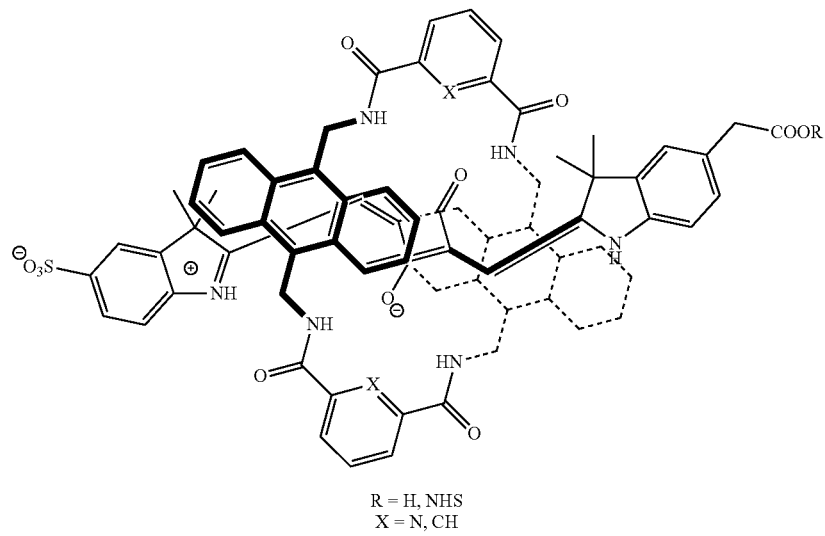
R = H, NHS
X = N, CH -continued
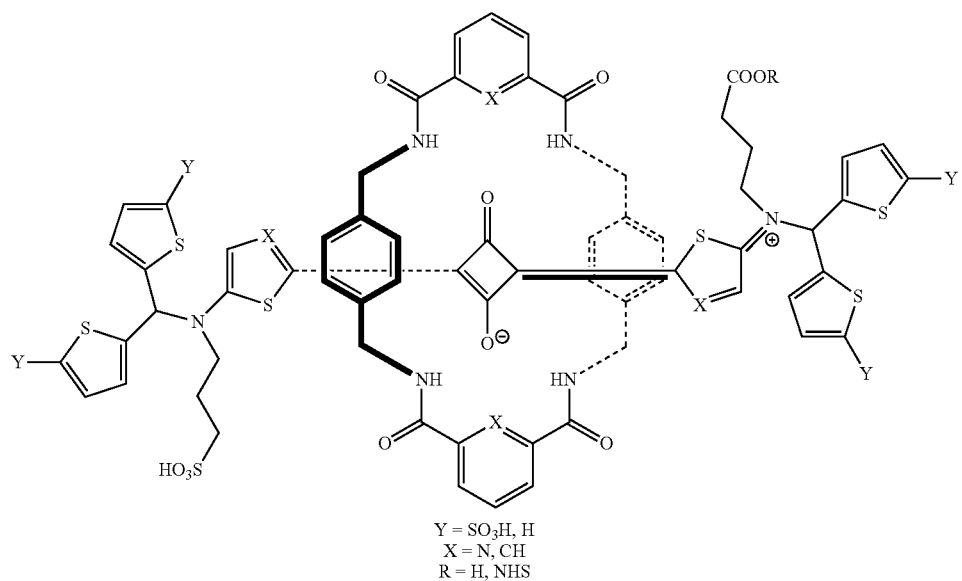
Y = SO₃H, H
X = N, CH
R = H, NHS
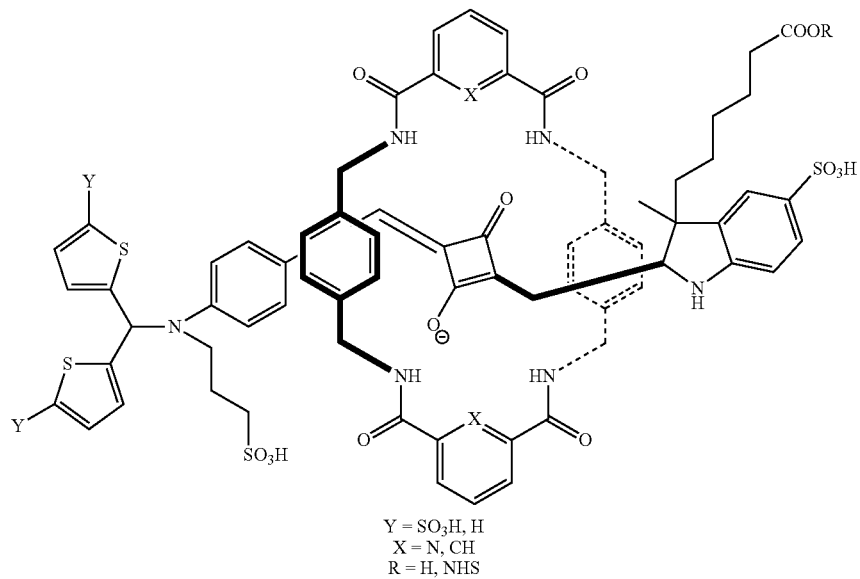
Y = SO₃H, H
X = N, CH
R = H, NHS

121    122
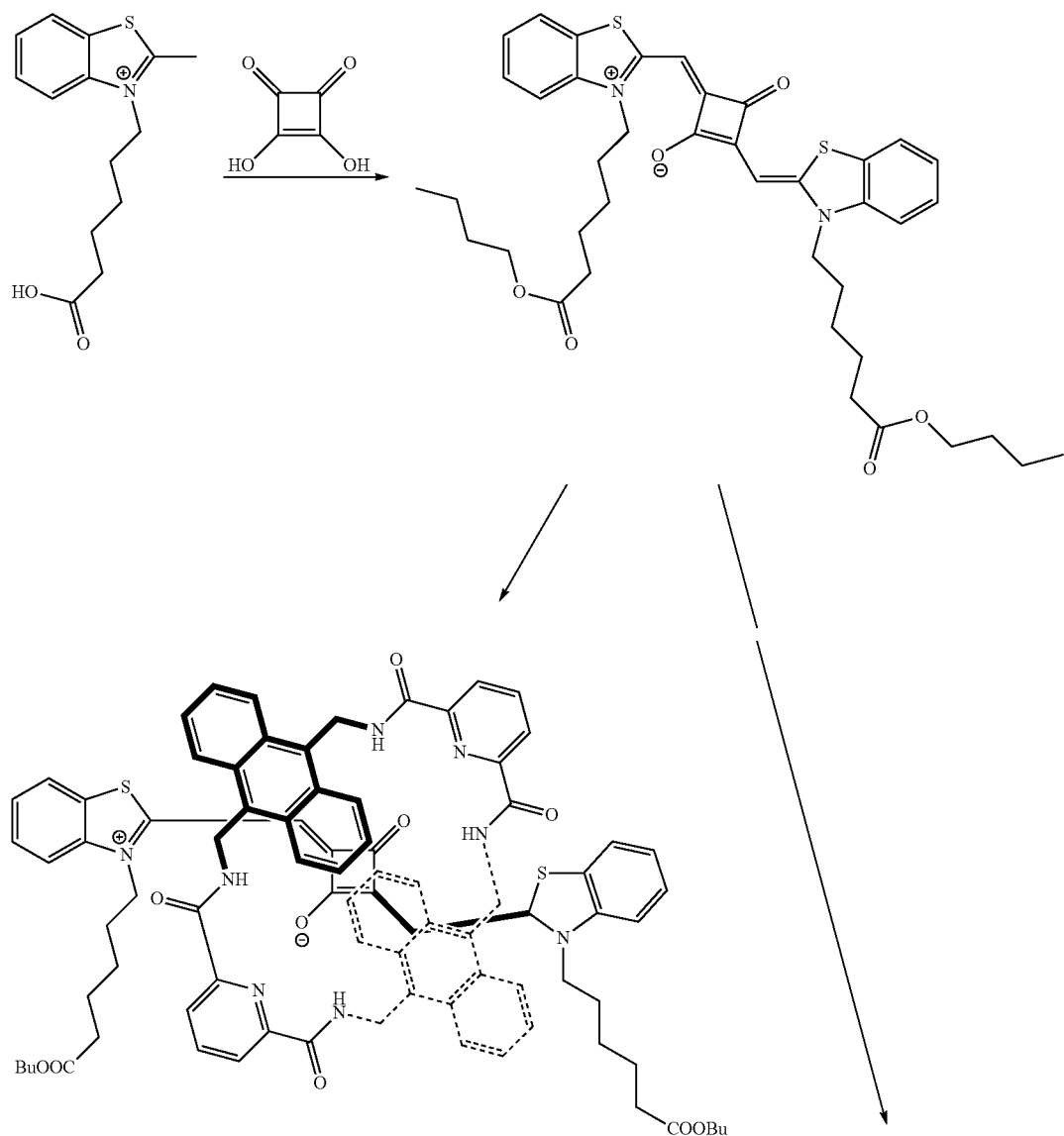
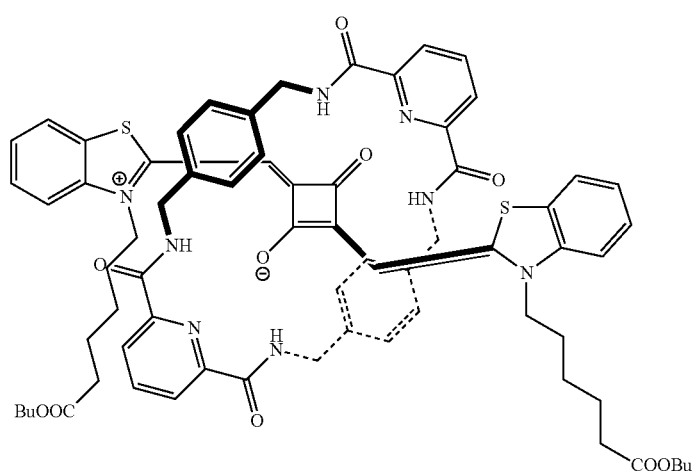

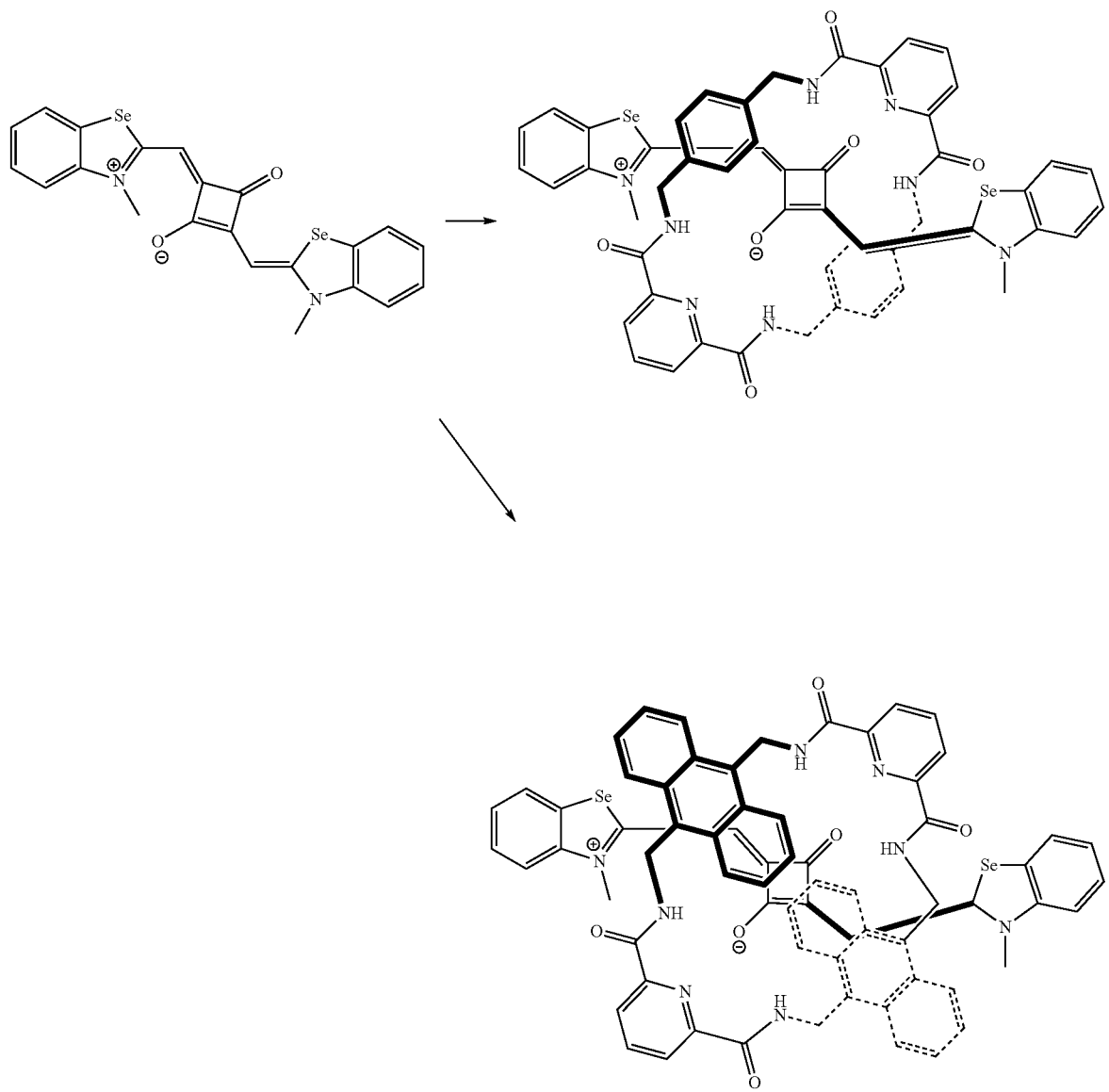

Example 17

General Protein Labelling Procedures and Determination of Dye-to-Protein Ratios Protein labelling reactions are carried out using a 50 mM bicarbonate buffer (pH 9.1). A stock solution of 1 mg of dye in 100 μL of anhydrous DMF is prepared. 10 mg of protein is dissolved in 1 mL of 100 mM bicarbonate buffer (pH 9.1). Dye from the stock solution is added, and the mixture is stirred for 8-12 h at room temperature.

Unconjugated dye is separated from labeled protein using gel permeation chromatography with SEPHADEX G50 (0.5 cm×20 cm column) and a 22 mM phosphate buffer solution (pH 7.3) as the eluent. The first colored band contains the dye-protein conjugate. The blue band with the much higher retention time contains the separated free dye. A series of labeling reactions using different dye-to-protein starting ratios are set up to obtain different dye-to-protein ratios for the labeled protein. Compared to the free forms, the protein-bound forms of the dyes sometimes show distinct changes in their spectral properties in particular when the dye is a squaraine dye.

The protein concentration is determined using either a BCA Protein Assay Reagent Kit from Pierce (Rockford, Ill.). Alternatively the protein concentration can be determined by measurement of the absorption around 280 nm. The dye-to-protein ratio (D/P) gives the number of dye molecules covalently bound to the protein.

Figure 4:
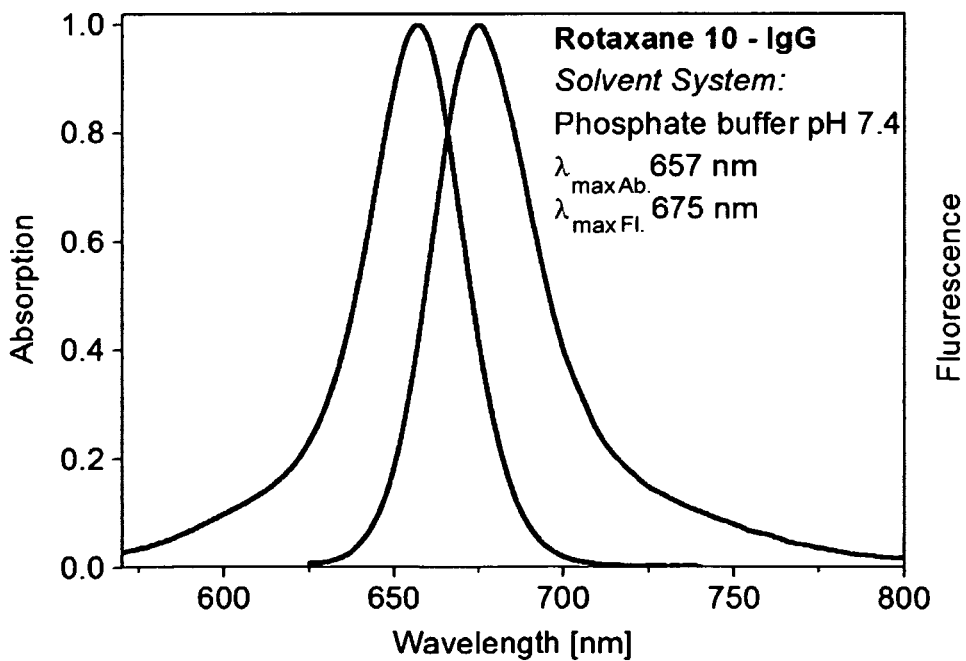
FIG. 4. A plot showing the absorption and emission spectra of the squaraine-rotaxane conjugate 10-IgG in phosphate buffer (pH 7.4, Dye-to-protein ratio=1.0).
Figure 5:
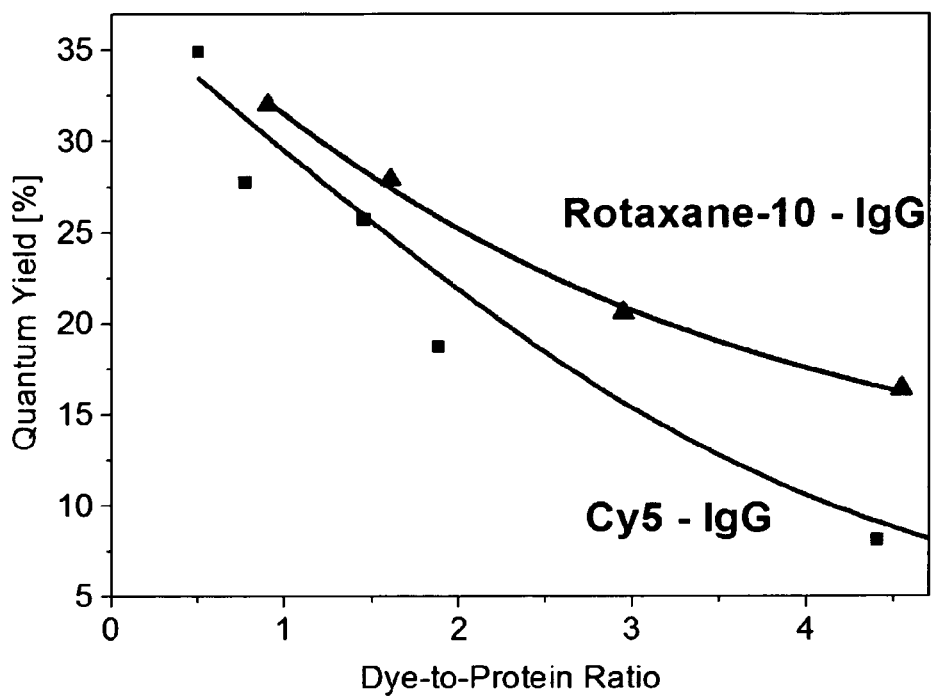
FIG. 5. A plot comparing quantum yield vs. dye-to-protein ratio for squaraine-rotaxane-conjugate 10-IgG and a Cy5-IgG conjugate in phosphate buffer (pH 7.4)

The table below is showing data on the photophysical properties for rotaxane-protein conjugates at various dye-to-protein ratios. The absorption and emission spectrum of a relevant conjugate is shown in FIG. 4. A graph of the Q.Y.'s of conjugates with different D/P ratios in comparison to Cy5, a commercially available protein marker, is shown in FIG. 5.

TABLE

| Sample | Dye-to-protein Ratio | Absorption max. [nm] | Extinction Coefficient [$M^{-1} \cdot cm^{-1}$] | Emission max. [nm] | Quantum Yield [%] |
|---|---|---|---|---|---|
| Rotaxane 10 | — | 655 | 200,000 | 673 | 25 |
| 10-IgG conjugate 1 | 1.0 | 657 | | 675 | 31 |
| 10-IgG conjugate 2 | 2.0 | 657 | | 675 | 25 |
| 10-IgG conjugate 3 | 3.0 | 657 | | 675 | 21 |
| 10-IgG conjugate 4 | 4.0 | 657 | | 675 | 18 |

Spectral and photophysical properties of compound 10 and 10-IgG

Covalent Labelling to IgG

385 µL (5.2 mg/mL) of IgG is dissolved in a 750 µL bicarbonate buffer (0.1 M, pH 9.0). 1 mg of NHS-ester (e.g. 10-NHS) is dissolved in 50 µL of DMF and slowly added to the above-prepared protein solution with stirring. After 20 h of stirring, the protein-conjugate is separated from the free dye using Sephadex G50 and a phosphate buffer (22 mM, pH 7.2). The first blue band that is isolated contains the labeled conjugate.

Conjugation to HSA 0.5 mg of the relevant NHS in 50 µL of DMF are slowly added to a stirred solution of 5 mg of HSA in 750 µL of bicarbonate buffer (0.1 M, pH 9.0). The mixture is stirred for another 6 h at room temperature. The mixture is dialyzed against a phosphate buffer (22 mM, pH 7.2) using a dialysis membrane (1500 FT, Union Carbid) with a cutoff of 10.000.

The labelling procedures of alternative reporter compounds having reactive functional groups are analoguous to the one reported here.

DESCRIPTION OF APPLICATIONS OF THE INVENTION

The above disclosed compositions exhibit utility for a variety of useful methods and for various assay formats.

The assay may be a competitive assay that includes a recognition moiety, a binding partner, and an analyte. Binding partners and analytes may be selected from the group consisting of biomolecules, drugs, and polymers, among others. In some competitive assay formats, one or more components are labeled with photoluminescent compounds in accordance with the invention. For example, the binding partner may be labeled with such a photoluminescent compound, and the displacement of the compound from an immobilized recognition moiety may be detected by the appearance of fluorescence in a liquid phase of the assay. In other competitive assay formats, an immobilized enzyme may be used to form a complex with the fluorophore-conjugated substrate.

The binding of antagonists to a receptor can be assayed by a competitive binding method in so-called ligand/receptor assays. In such assays, a labeled antagonist competes with an unlabeled ligand for the receptor binding site. One of the binding partners can be, but not necessarily has to be, immobilized. Such assays may also be performed in microplates. Immobilization can be achieved via covalent attachment to the well wall or to the surface of beads.

Other preferred assay formats are immunological assays. There are several such assay formats, including competitive binding assays, in which labeled and unlabeled antigens compete for the binding sites on the surface of an antibody (binding material). Typically, there is a certain incubation time required to provide sufficient time for equilibration. Such assays can be performed in a heterogeneous or homogeneous fashion.

Sandwich assays may use secondary antibodies and excess binding material may be removed from the analyte by a washing step.

Other types of reactions include binding between avidin and biotin, protein A and immunoglobulins, lectins and sugars (e.g., concanavalin A and glucose).

Certain dyes of the invention are charged due to the presence sulfonic groups. These compounds are impermeant to membranes of biological cells. In these cases treatments such as electroporation and shock osmosis can be used to introduce the dye into the cell. Alternatively, such dyes can be physically inserted into the cells by pressure microinjection, scrape loading etc.

The reporter compounds described here also may be used to sequence nucleic acids and peptides. For example, fluorescently-labeled oligonucleotides may be used to trace DNA fragments. Other applications of labeled DNA primers include fluorescence in-situ hybridization methods (FISH) and for single nucleotide polymorphism (SNIPS) applications, among others.

Multicolor labeling experiments may permit different biochemical parameters to be monitored simultaneously. For this purpose, two or more reporter compounds are introduced into the biological system to report on different biochemical functions. The technique can be applied to fluorescence in-situ hybridization (FISH), DNA sequencing, fluorescence microscopy, and flow cytometry. One way to achieve multicolor analysis is to label biomolecules such as nucleotides, proteins or DNA primers with different luminescent reporters having distinct luminescence properties. Luminophores with narrow emission bandwidths are preferred for multicolor labeling, because they have only a small overlap with other dyes and hence increase the number of dyes possible in a multicolor experiment. Importantly, the emission maxima have to be well separated from each other to allow sufficient resolution of the signal. A suitable multicolor triplet of fluorophores would include a Cy3-analog of this invention, TRITC, and a Cy5-analog as described herein, among others.

Figure 8:
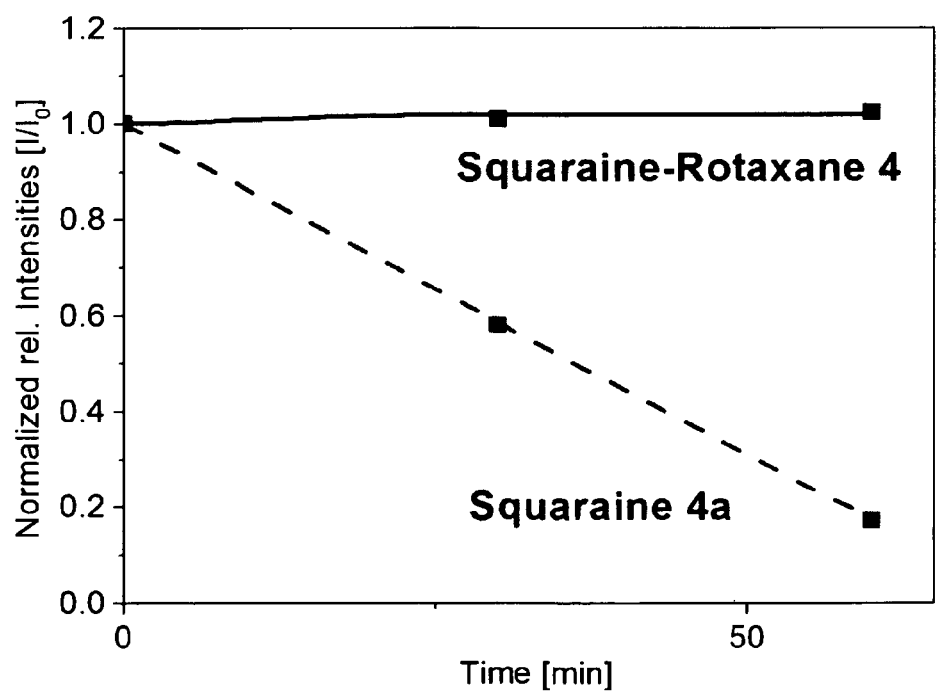
FIG. 8. A plot comparing the stability of compounds 4 and 4a in the presence of NaOH solution at pH 13. After 60 min incubation the solutions were neutralized with acid and the emission was measured. The intensities were then compared to the intensity at time=0.
Figure 9:
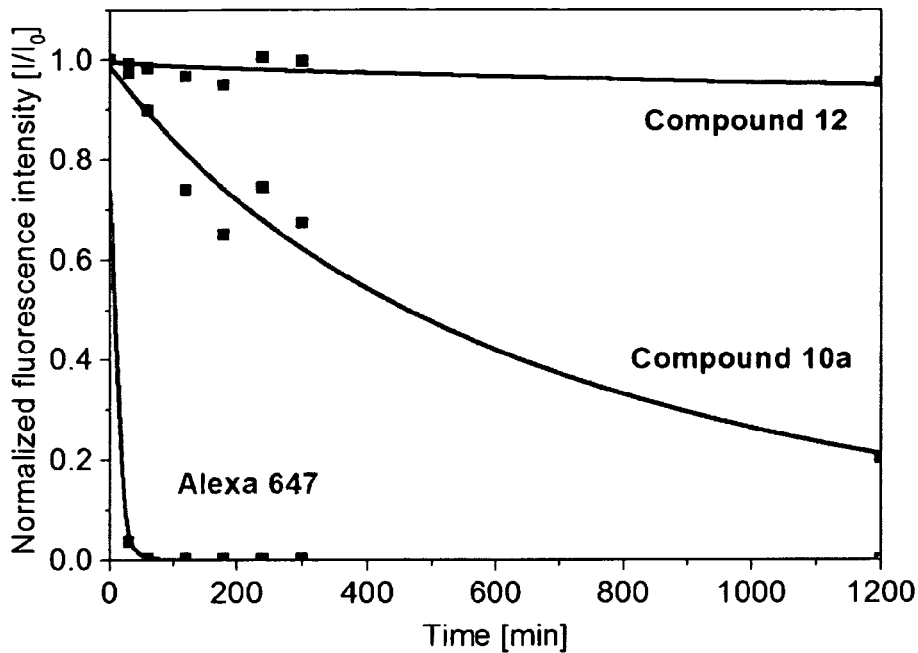
FIG. 9. A plot comparing the decrease of the fluorescence intensity of 12, 10a and Alexa 647 in buffer pH 9.4 in presence of $H_2O_2$.
Figure 10:
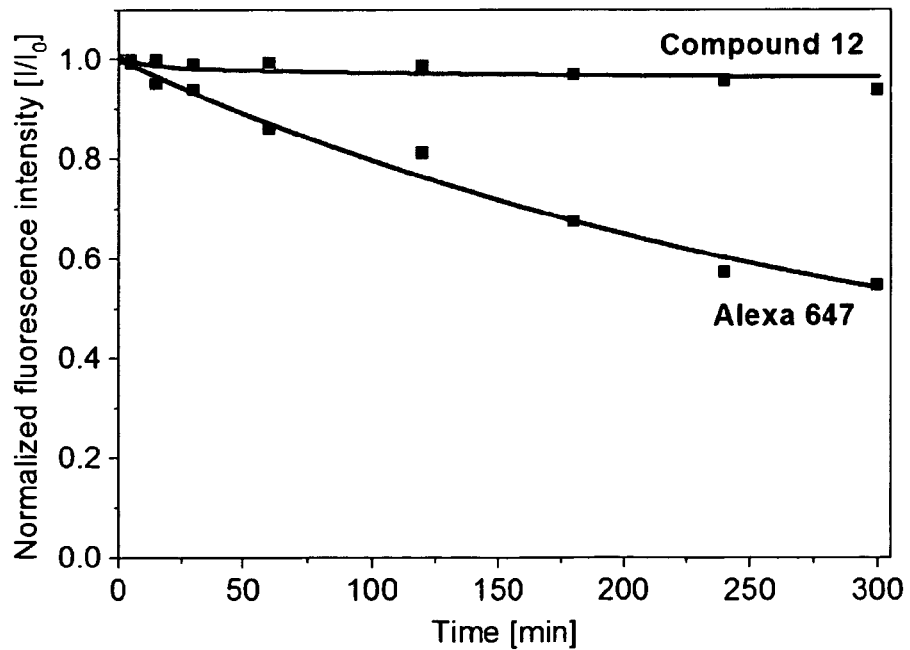
FIG. 10. A plot showing the photostability of 12 and that of Alexa 647.

Phosphoramidites are useful functionalities for the covalent attachment of dyes to oligos in automated oligonucleotide synthesizers. They are easily obtained by reacting the hydroxyalkyl-modified dyes of the invention with 2-cyanoethyl-tetraisopropyl-phosphorodiamidate and 1-H tetrazole in methylene chloride. The phosphoramidite chemistry requires these dyes to be stable against deprotection chemistries that involve treatment with a base. We therefore tested the stability of rotaxane 4 at pH 13 in comparison to the squaraine precursor 4a. The result is shown in FIG. 8.

The simultaneous use of FISH (fluorescence in-situ hybridization) probes in combination with different fluorophores is useful for the detection of chromosomal translocations, for gene mapping on chromosomes, and for tumor diagnosis, to name only a few applications. One way to achieve simultaneous detection of multiple sequences is to use combinatorial labeling. The second way is to label each nucleic acid probe with a luminophore with distinct spectral properties. Similar conjugates can be synthesized from this invention and can be used in a multicolor multi-sequence analysis approach.

In another approach the dye-compositions of this invention might be used to directly stain or label a sample so that the sample can be identified and or quantitated. Such dyes might be added/labeled to a target analyte as a tracer. Such tracers could be used e.g. in photodynamic therapy where the labeled compound is irradiated with a light source and thus producing singlet oxygen that helps to destroy tumor cells and diseased tissue samples.

The reporter compounds of the invention can also be used for screening assays for a combinatorial library of compounds. The compounds can be screened for a number of characteristics, including their specificity and avidity for a particular recognition moiety.

Assays for screening a library of compounds are well known. A screening assay is used to determine compounds that bind to a target molecule, and thereby create a signal change which is generated by a labeled ligand bound to the target molecule. Such assays allow screening of compounds that act as agonists or antagonists of a receptor, or that disrupt a protein-protein interaction. It also can be used to detect hybridization due to binding of DNA and/or RNA.

Other screening assays are based on compounds that affect the enzyme activity. For such purposes, quenched enzyme substrates of the invention could be used to trace the interaction with the substrate. In this approach, the cleavage of the fluorescent substrate leads to a change in the spectral properties such as the excitation and emission maxima, intensity and/or lifetime, which allows distinguishing between the free and the bound luminophore.

The reporter compounds disclosed above may also be relevant to single molecule fluorescence microscopy (SMFM) where detection of single probe molecules depends on the availability of a fluorophore with high fluorescence yield, high photostability, and long excitation wavelength including stability against radical oxygen species.

While anthracene and benzene-type diamines are symmetrical, rotaxanes based on naphthalene-type diamines are unsymmetrical and could be used to introduce non-linear properties in these rotaxane molecules. In addition these molecules could be useful as molecular switches.

The dye compositions are also useful for use as biological stains. There are limitations in some instances to the use of compounds as labels. For example, typically only a limited number of dyes may be attached to a biomolecules without altering the fluorescence properties of the dyes (e.g. quantum yields, lifetime, polarization, emission characteristics, etc.) and/or the biological activity of the bioconjugate. Typically quantum yields may be reduced at higher degrees of labelling. The current invention should help to overcome some of these limitations by reducing the aggregation tendencies of these dye compositions.

Another means to overcome the above limitation for the use of such compounds as fluorescent markers offers encapsulation into beads. Fluorescent beads and polymeric materials are becoming increasingly attractive as labels and materials for bioanalytical and sensing applications. Various companies offer particles with defined sizes ranging from nanometers to micrometers. Noncovalent encapsulation in beads may be achieved by swelling the polymer in an organic solvent, such as toluene or chloroform, containing the dye. Covalent encapsulation may be achieved using appropriate reactive functional groups on both the polymer and the dyes.

In general, hydrophobic versions of the invention may be used for non-covalent encapsulation in polymers, and one or more dyes could be introduced at the same time. Surface-reactive fluorescent particles allow covalent attachment to molecules of biological interest, such as antigens, antibodies, receptors etc. Hydrophobic versions of the invention such as dye having lipophilic substituents such as phospholipids will non-covalently associate with lipids, liposomes, lipoproteins. They are also useful for probing membrane structure and membrane potentials.

Dyes lacking ionic charges are used for cell-based applications where the dye conjugate is dissolved in the loading buffer and allowed to diffuse through the cell membrane into the interior of the cell. For this purpose rotaxanes with neutral groups such as phosphonate or sulfonamides that sustain water-solubility of the compound without adding ionic charges are preferred.

Hydrophobic versions of these compositions are also useful for the detection of proteins (BSA, HSA, globins etc.) based on gel and capillary electrophoresis.

Compounds of this invention may also be attached to the surface of metallic nanoparticles such as gold or silver nanoparticles or colloids. It has recently been demonstrated that fluorescent molecules may show increased quantum yields near metallic nanostructures e.g. gold or silver nanoparticles (O. Kulakovich et al., Nanoletters 2(12) 1449-52 (2002)). This enhanced fluorescence may be attributable to the presence of a locally enhanced electromagnetic field around metal nanostructures. The changes in the photophysical properties of a fluorophore in the vicinity of the metal surface may be used to develop novel assays and sensors. In one example the nanoparticle may be labeled with one member of a specific binding pair (antibody, protein, receptor, etc.) and the complementary member (antigen, ligand) may be labeled with a fluorescent molecule in such a way that the interaction of both binding partners leads to an detectable change in one or more fluorescence properties (such as intensity, quantum yield, lifetime, among others). Replacement of the labeled binding partner from the metal surface may lead to a change in fluorescence that can then be used to detect and/or quantify an analyte.

Gold colloids can be synthesized by citrate reduction of a diluted aqueous $HAuCl_4$ solution. These gold nanoparticles are negatively charged due to chemisorption of citrate ions. Surface functionalization may be achieved by reacting the nanoparticles with thiolated linker groups containing amino or carboxy functions. In another approach, thiolated biomolecules are used directly for coupling to these particles.

In recent studies (T. Fare et al., Anal. Chem. 75(17), 4672-4675 (2003)), researchers made an observation that the fluorescence signals of cyanine dyes such as CY5 dye and the ALEXA 647 dyes in microarrays are strongly dependent on the concentration of ozone during post-hybridization array washing. Controlled exposures of microarrays to ozone confirmed this factor as the root cause, and showed the susceptibility of a class of cyanine dyes (e.g., CY5 dyes, ALEXA 647 dyes) to ozone levels as low as 5-10 ppb for periods as short as 10-30 s.

One of the significant findings was the low dose level (ozone concentration multiplied by exposure time) that could induce the onset of the phenomenon, suggesting many labs may be at risk. For example, it is not uncommon that the environmental ozone levels would exceed 60 ppb during peak traffic hours on a sunny summer afternoon. Reporter compounds present on or in arrays that are exposed to these levels for as short as 1 min may begin to show significant degradation in a typical laboratory setting.

Figure 7:
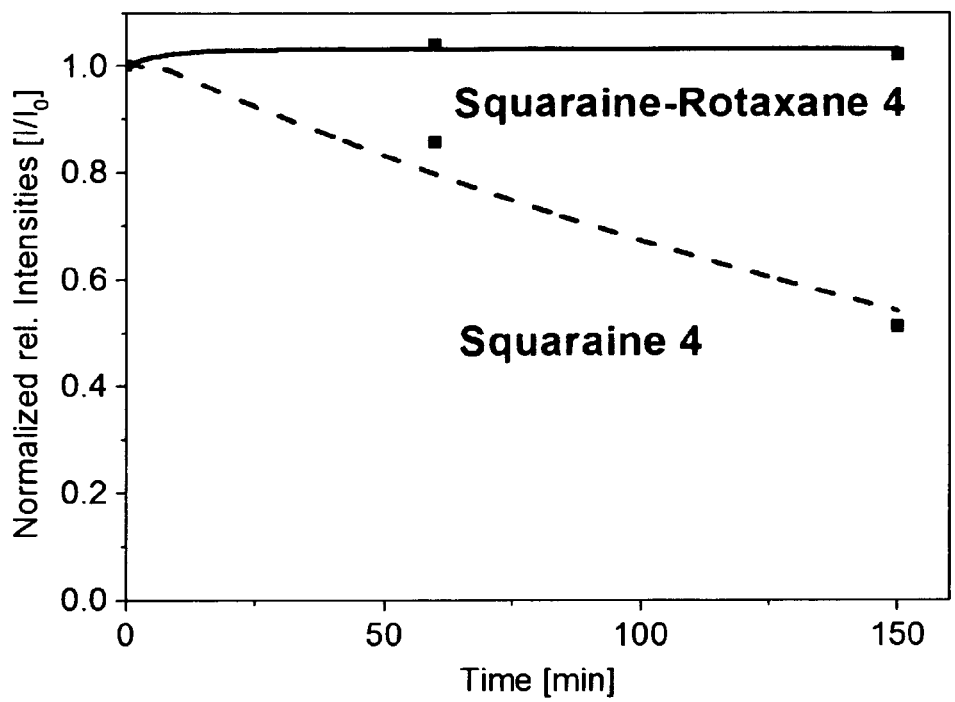
FIG. 7. A plot comparing the relative luminescent intensity changes of rotaxane 4 and its squaraine precursor 4a upon exposure to a hydrogen peroxide solution.

There are ways that help to eliminate the occurrence of ozone effects on microarrays, for example equipping laboratories with HVAC systems having filters to significantly reduce ozone levels, or the use of dye-protecting solutions to avoid signal degradation. However, each of these approaches may add additional costs and/or time to perform the assay. These findings suggest the need for dyes and labels in the 600 to 700 nm wavelength range with improved chemical and photochemical stability. Dye compositions of this invention exhibit increased photochemical but also chemical stability in particular against oxidative reagents such as peroxides (FIG. 7) and should therefore be excellent reagents for the use in microarrays.

Analytes

The invention may be used to detect an analyte that interacts with a recognition moiety in a detectable manner. As such, the invention can be attached to a recognition moiety which is known to those of skill in the art. Such recognition moieties allow the detection of specific analytes. Examples are pH- or potassium-sensing molecules, e.g., synthesized by introduction of potassium chelators such as crown-ethers (aza crowns, thia crowns etc). Dyes with N—H substitution in the heterocyclic rings such as 4 exhibit pH-sensitive absorption and emission (S. Miltsov et al., Tetrahedron Lett. 40: 4067-68 (1999), M. E. Cooper et al., J. Chem. Soc. Chem. Commun. 2000, 2323-2324). Calcium-sensors based on the BAPTA (1,2-Bis(2-aminophenoxy)ethan-N,N,N',N'-tetra-acetic acid) chelating moiety are frequently used to trace intracellular ion concentrations. The combination of a compound of the invention and the calcium-binding moiety BAPTA may lead to new long-wavelength absorbing and emitting Ca-sensors which could be used for determination of intra- and extracellular calcium concentrations (Akkaya et al., Tetrahedron Lett. 38:4513-4516 (1997)). Additionally, or in the alternative, reporter compounds already having a plurality of carboxyl functional groups may be directly used for sensing and/or quantifying physiologically and environmentally relevant ions.

Figure 6:
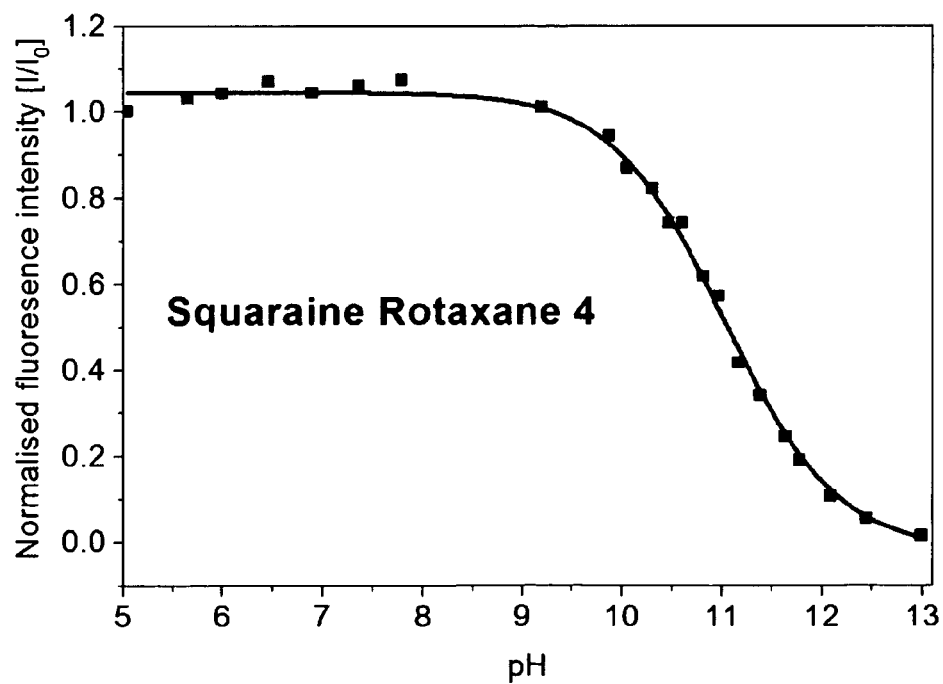
FIG. 6. A plot of the normalized fluorescence intensity vs. pH for rotaxane 4 showing a pKa of around pH 11.

NH-substituted dyes of this invention are pH sensitive and may also be useful for the assessment of the intracellular pH and for applications where the local pH of the environment changes e.g. cell-based measurements of G-protein coupled receptors as described in M. E. Cooper et al. J. Chem. Soc. Chem. Commun. 2000, 2323-2324. The water-soluble dyes may be used directly or the reactive pH-sensitive dyes of the invention are associated with specific biomolecules which bind to certain domains in cells thus enabling the pH of only that specific environment to be assessed. While the dioxo-squaraines and dioxo-squaraine-rotaxanes (see Example 3) have pKa values in the basic pH range (FIG. 6) (Miltsov et al., Tetrahedron Lett. 40, 4067-68 (1999)), the pKa's of squaraine-ring-substituted versions like the thio-derivatives may be closer to the physiological pH range, which would makes them more useful for these type of measurements. It is understood that the dyes pKa's can be tuned to cover a broad pH-range by variation of the substituents on the heterocyclic bases as well as on the squaraine bridge.

Fluorescence Methods

The disclosed reporter compounds may be detected using common intensity-based fluorescence methods. Unrotaxanated squaraine dyes are known to have lifetimes in the range of hundreds of ps to a few ns. The table below provides some of the lifetime data that were measured for the free squaraines and their rotaxanes. The lifetime for the aniline-based squaraine 10a increases about 2 fold upon conjugation to an antibody and the lifetimes of the IgG-conjugates seem to be relatively independent of the dye-to-protein ratios (Table below).

Importantly, the already long average lifetime of the water-soluble indolenine squaraine 4a further increases to 2.4 ns upon conversion into the rotaxane 4. This lifetime is comparable to that of free squaraine dyes in non-aqueous solution, where less quenching is observed.

The nanosecond lifetime and long-wavelength absorption and emission of these dyes may allow them to be measured using relatively inexpensive instrumentation that employs laser diodes for excitation and avalanche photodiodes for detection. Typical assays based on the measurement of the fluorescence lifetime as a parameter include for example FRET (fluorescence resonance energy transfer) assays. The binding between a fluorescent donor labeled species (typically an antigen) and a fluorescent acceptor labeled species may be accompanied by a change in the intensity and the fluorescence lifetime. The lifetime can be measured using intensity- or phase-modulation-based methods (J. R. LAKOWICZ, PRINCIPLES OF FLUORESCENCE SPECTROSCOPY ($2^{nd}$ ed. 1999)).

The lifetimes in the order of a few ns that have been measured for some of the rotaxane-dye structures in aqueous solution (see Table below) make these labels extremely useful as tracers for applications in fluorescence polarization based assays. Fluorescence polarization immunoassays (FPI) are widely applied to quantify low molecular weight antigens. The assays are based on polarization measurements of antigens labeled with fluorescent probes. The requirement for polarization probes used in FPIs is that emission from the unbound labeled antigen be depolarized and increase upon binding to the antibody. Low molecular weight species labeled with the compounds of the invention can be used in such binding assays, and the unknown analyte concentration can be determined by the change in polarized emission from the fluorescent tracer molecule.

The long fluorescence lifetimes of benzo-selenazole-based squaraines in chloroform suggest that water-soluble rotaxane-analogs of these dyes might be useful as polarization probes.

TABLE

Fluorescence lifetimes of squaraines and squaraine rotaxanes ($\lambda_{ex}$: 630 nm, $\lambda_{obs}$: 670 nm)

| Compound | Solvent | $\tau_1$ [ns] ($f_1$, %) | $\tau_2$ [ns] ($f_2$, %) | $\tau_{mean}$ [ns] | $\chi^2$ |
|---|---|---|---|---|---|
| Rotaxane 15 | Water | 3.1 (100) | — | 3.1 | 1.5 |
| Squaraine 10a | Water | 0.05 (100) | — | 0.05 | 1.51 |
| Rotaxane 12 | Water | 3.1 (100) | — | 3.1 | 1.01 |
| Rotaxane 10-NHS | Water | 0.90 (100) | — | 0.90 | 1.1 |
| 10-IgG, (D/P 0.90) | Water | 0.56 (14) | 2.05 (86) | 1.83 | 1.64 |
| 10-IgG, (D/P 1.60) | Water | 0.47 (13) | 2.02 (87) | 1.82 | 0.94 |
| 10-IgG, (D/P 2.95) | Water | 0.42 (15) | 1.83 (85) | 1.62 | 1.25 |
| Squaraine 5a | Chloroform | 0.616 (2) | 3.42 (98) | 3.36 | 1.65 |
| Rotaxane 5 | Chloroform | 0.86 (2) | 3.59 (98) | 3.52 | 0.78 |
| Squaraine 4a | Water | 1.56 (100) | — | 1.56 | 1.20 |
| Rotaxane 4 | Water | 2.4 (100) | — | 2.4 | 1.23 |
| Rotaxane 3 | Chloroform | 2.79 (100) | — | 2.79 | 1.1 |

Luminescent dyes of this invention are also useful as fluorescent acceptors in TR-FRET applications with luminescent lanthanides as donors. In these assays the emission from both the donor and the acceptor is collected and ratioed to increase the robustness of the assay.

The luminescent rotaxanes of the invention are also useful for in vivo near infrared diagnostic methods, as described in U.S. Pat. No. 6,083,485 (hereby incorporated by reference). Such methods typically include administering a rotaxane of the present invention, diseased tissue to light in the visible and near infrared range, and recording the emitted light produced from the rotaxane.

Compositions and Kits

The invention also provides compositions, kits and integrated systems for practicing the various aspects and embodiments of the invention, including producing the novel compounds and practicing of assays. Such kits and systems may include a reporter compound as described above, and may optionally include one or more of solvents, buffers, calibration standards, enzymes, enzyme substrates, and additional reporter compounds having similar or distinctly different optical properties.

Although the invention has been disclosed in preferred forms, the specific embodiments thereof as disclosed and illustrated herein are not to be considered in a limiting sense, because numerous variations are possible. Applicant regards the subject matter of his invention to include all novel and nonobvious combinations and subcombinations of the various elements, features, functions, and/or properties disclosed herein. No single element, feature, function, or property of the disclosed embodiments is essential. The following claims define certain combinations and subcombinations of elements, features, functions, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

We claim:

1. A rotaxane having the formula:

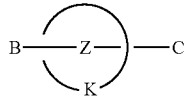

where B—Z—C is a reporter molecule and K is a macrocycle that encircles and interlocks with the reporter molecule;

K has the formula $K^1$ or $K^2$, where $K^1$ is

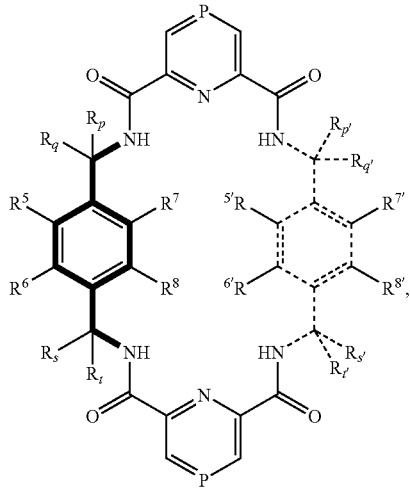

and $K^2$ is

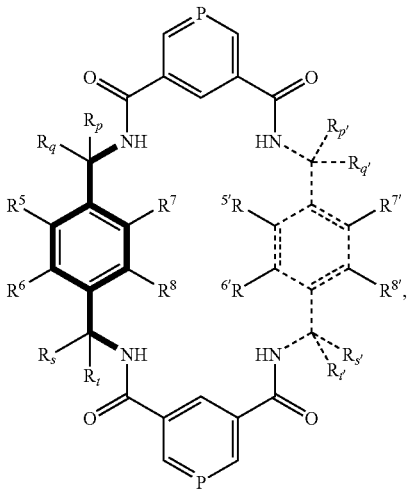

where substituents $R^5$, $R^{5'}$, $R^6$, $R^{6'}$, $R^7$, $R^{7'}$, $R^8$ and $R^{8'}$ are methyl;

$R_p$, $R_q$, $R_s$, $R_t$, $R_{p'}$, $R_{q'}$, $R_{s'}$, $R_{t'}$ are independently selected from H, $CH_3$, alkyl, —$CH_2OH$, —$CH_2O$-alkyl, L-$R^x$, L-$S_c$ and L-$R^{\pm}$;

P is either $CR^3$, N, $^+N$—$R^4$ or $^+O$;

$R^3$ when present is independently selected from H, L-$R^x$, L-$S_c$ and L-$R^{\pm}$, alkyl, aryl, alkoxy, alkyl-aryl, F, Br, Cl, I, OH, nitro, and cyano;

$R^4$ when present is independently selected from the group of H, L-$R^x$, L-$S_c$ and L-$R^{\pm}$, alkyl, aryl, alkoxy, alkyl-aryl;

L is a single covalent bond, a covalent linkage that is linear or branched, cyclic or heterocyclic, saturated or unsaturated, having 1-20 nonhydrogen atoms from the group of C, N, P, O and S, in such a way that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^x$ is a reactive group;

$S_c$ is a conjugated substance; and $R^{\pm}$ is an ionic group;

Z is a core of the reporter molecule, and has the formula

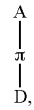

where π is a four-membered aromatic ring and A, B, C and D are substituents of the four-membered ring;

wherein B and C are separated by one of substituents A or D, and wherein B is one of $W^4$, $W^6$, $W^8$, $W^{10}$, $W^{12}$, $W^{14}$, $W^{16}$ or $W^{18}$ and C is one of $W^3$, $W^5$, $W^7$, $W^9$, $W^{11}$, $W^{13}$, $W^{15}$ or $W^{17}$, in which case one of A or D is negatively charged;

where A and D are neutral, they are selected from the group consisting of =O, =S, =Se, =Te, =N—$R^a$, and =C(R$^b$)(R$^c$), where R$^a$, R$^b$ and R$^c$ are selected from the group consisting of H, L-S$_c$, L-R$^x$, L-R$^±$, aliphatic, aromatic, alicyclic, and aryl-alkyl, where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; —COOH, —CN, —OH, —SO$_3$H, —PO$_3$H$_2$, —O—PO$_3$H$_2$, —PO$_3$R$_2{}^m$, —O—PO$_3$R$_2{}^m$, —CONHR$^m$, —CONH$_2$, COO—NHS and COO—R$^m$, where R$^m$ is selected from a group consisting of L-S$^x$, L-R$^x$, L-R$^±$, aliphatic substituents and aromatic substituents; or R$^b$ and R$^c$, taken in combination, form a cyclic or heterocyclic ring structure;

where A and D are negatively charged, they are independently selected from the group consisting of —O$^⊖$, —S$^⊖$, —Se$^⊖$, —Te$^⊖$, —(N—R$^a$)$^⊖$, —(C(R$^b$)(R$^c$))$^⊖$;

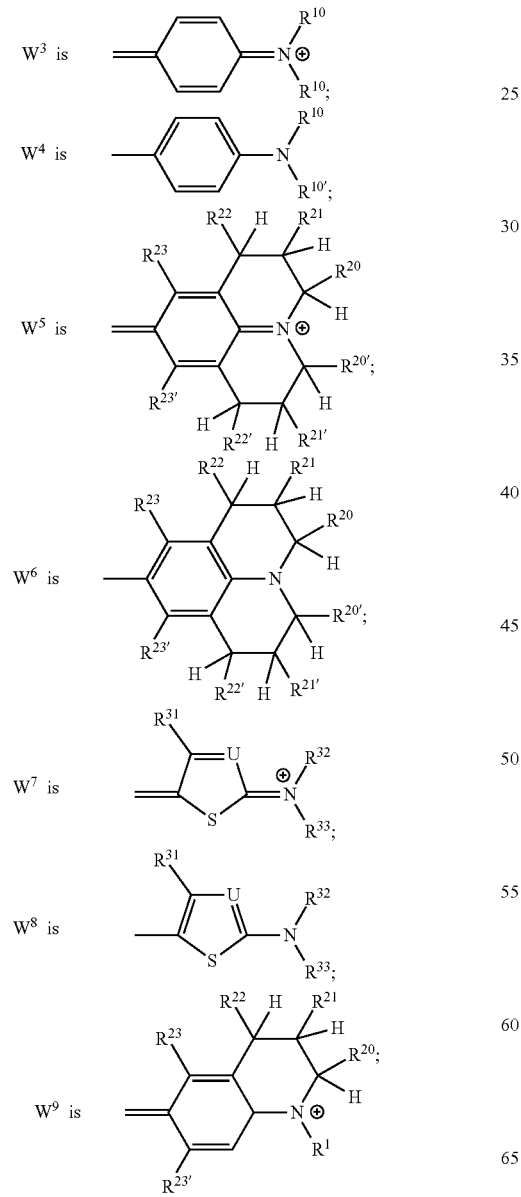

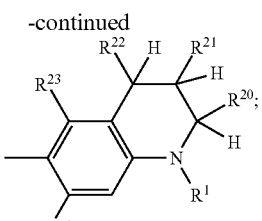

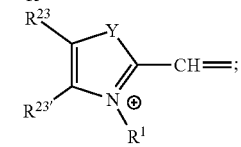

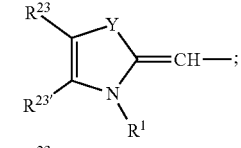

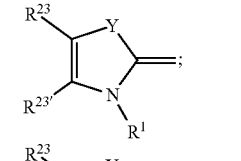

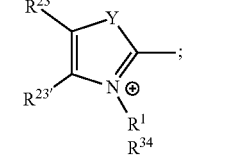

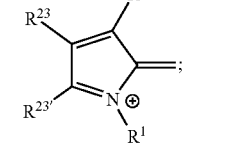

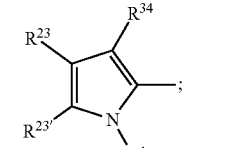

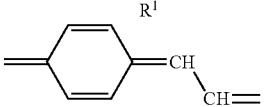

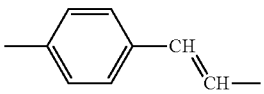

each Y is independently selected from the group consisting of O, S, N—R$^d$, CR$^e$=CR$^f$ and C(R$^i$)(R$^j$), where R$^d$ is selected from the group consisting of H, L-S$_c$, L-R$^x$, L-R$^±$, —CH$_2$—CONH—SO$_2$-Me, aliphatic groups, alicyclic groups, aromatic groups;

R$^e$ and R$^f$ are independently H, R$^x$, R$^±$, L-S$_c$, L-R$^x$, L-R$^±$, —CH$_2$—CONH—SO$_2$-Me, aliphatic groups, alicyclic groups, or aromatic groups; where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

R$^i$ and R$^j$ are independently H, L-S$_c$, L-R$^x$, L-R$^±$, —CH$_2$—CONH—SO$_2$-Me, aliphatic groups, alicyclic groups, or aromatic groups, where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; or $R^i$ and $R^j$ taken in combination form a ring-system that is optionally further substituted by one or more reactive or ionic substituents;

$R^1$ is selected from H, L-$S_c$, L-$R^x$, L-$R^\pm$, —$CH_2$—CONH—$SO_2$-Me, aliphatic groups, alicyclic groups, alkylaryl groups, aromatic groups, benzyl, substituted benzyl; where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

$R^{10}$ and $R^{10'}$ are selected from H, L-$S_c$, L-$R^x$, L-$R^\pm$, —$CH_2$—CONH—$SO_2$-Me, aliphatic groups, alicyclic groups and aromatic groups, where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium, and

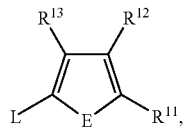

where L is a linker as defined above and E is selected from O, S, Se, $NR^{16}$, $CR^{14}$=N, $CR^{14}$=$N^+R^{16}$;

where $R^{11}$, $R^{12}$, $R^{13}$ and $R^{14}$ are independently H, L-$S_c$, L-$R^x$, L-$R^\pm$, —$CH_2$—CONH—$SO_2$-Me, aliphatic, alicyclic, aromatic, alkyl-aryl, F, Cl, Br, I, $NH_2$, —COOH, —CH=O, —CN, azido, —OH, —$NO_2$, —$SO_3H$, —$PO_3^{2\ominus}$, —O—$PO_3^{2\ominus}$, —$PO_3R^{m\ominus}$, —O—$PO_3R^{m\ominus}$, —$CONH_2$, $CONHR^m$, COO—NHS and COO—$R^m$, where $R^m$ is selected from a group consisting of L-$S_c$, L-$R^x$, L-$R^\pm$, aliphatic substituents, aromatic substituents; where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; and $R^{16}$ is selected from H, L-$S_c$, L-$R^x$, L-$R^\pm$, —$CH_2$—CONH—$SO_2$-Me, aliphatic groups, alicyclic groups, alkylaryl groups, aromatic groups, each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium, or $R^{10}$ and $R^{10'}$ may be a part of a heterocyclic ring that is itself optionally further substituted by H, L-$S_c$, L-$R^x$, L-$R^\pm$, —$R^\pm$, $R^x$, alkyl or aryl;

$R^{20}$, $R^{21}$, $R^{22}$, $R^{23}$, $R^{20'}$, $R^{21'}$, $R^{22'}$, and $R^{23'}$ of $W^5$ and $W^6$, and $R^{31}$ and $R^{34}$ of $W^7$ and $W^8$ are independently selected from H, L-$S_c$, L-$R^x$, L-$R^\pm$, —$CH_2$—CONH—$SO_2$-Me, aliphatic, alicyclic, aromatic, alkyl-aryl, F, Cl, Br, I, $NH_2$, —COOH, CH=O, —CN, azido, —OH, —$NO_2$, —$SO_3H$, —$PO_3^{2\ominus}$, —O—$PO_3^{2\ominus}$, —$PO_3R^{m\ominus}$, —O—$PO_3R^{m\ominus}$, —$CONH_2$, $CONHR^m$, COO—NHS and COO—$R^m$, where $R^m$ is selected from a group consisting of L-$S_c$, L-$R^x$, L-$R^\pm$, aliphatic substituents, aromatic substituents; where each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; and U in $W^7$ and $W^8$ is independently selected from $C(R^{34})$ or nitrogen, $R^{32}$ and $R^{33}$ are independently selected from H, L-$S_c$, L-$R^x$, L-$R^\pm$, —$CH_2$—CONH—$SO_2$-Me, aliphatic groups, alicyclic groups, alkylaryl groups, and aromatic groups; alternatively $R^{32}$ and $R^{33}$ may be a part of a heterocyclic ring that is itself optionally further substituted by H, L-$S_c$, L-$R^x$, L-$R^\pm$, $R^\pm$, $R^x$, alkyl or aryl; and the substituents of $W^9$ to $W^{18}$ are already listed above; $V^1$ in $W^{17}$ is either $W^3$ or $W^7$ and $V^2$ in $W^{18}$ is either $W^4$ or $W^8$.

2. The rotaxane of claim 1, where at least one substituent of Z includes a reactive group $R^x$ that is independently selected from acrylamide, an activated ester of a carboxylic acid, an acyl nitrile, an aldehyde, an alkyl halide, an anhydride, an aniline, an aryl halide, an aziridine, a boronate, a carboxylic acid, a diazoalkane, a haloacetamide, a halotriazine, a hydrazine, an amine, an activated double bond containing group, an imido ester, an isothiocyanate, an isocyanate, a maleimide, a phosphoramidite, a pyrylium moiety, a reactive platinum complex, a sulfuryl halide, a thiol group, or a photoactivatable group.

3. The rotaxane of claim 2, where the reactive group is selected to form a covalent bond with amine moieties selected from the group consisting of N-hydroxysuccinimide esters, isothiocyanates, and sulfonylhalogenides.

4. The rotaxane of claim 2, where the reactive group is selected to form a covalent bond with thiol moieties selected from the group consisting of iodoacetamides and maleimides.

5. The rotaxane of claim 2, where the reactive group is selected to form a covalent bond with nucleic acids that incorporate phosphoramidites.

6. The rotaxane of claim 1, where at least one substituent of Z includes a conjugated substance $S_c$.

7. The rotaxane of claim 6, where the conjugated substance $S_c$ is selected from the group consisting of a peptide, a nucleotide, a polypeptide, a polynucleotide, a bead, a microplate well surface, a phospholipid, a metallic nanoparticle, an amino acid, a nucleic acid, a sugar, polysaccharide, oligosaccharide, and a second fluorescent dye.

8. The rotaxane of claim 1, where at least one substituent of Z is an ionic substituent $R^\pm$ capable of increasing the hydrophilicity of the entire rotaxane.

9. The rotaxane of claim 8, where the ionic substituent $R^\pm$ is selected from the group consisting of —$SO_3^\ominus$, —O—$SO_3^\ominus$, —$COO^\ominus$, —$PO_3^{2\ominus}$, —O—$PO_3^{2\ominus}$, —$PO_3R^{m\ominus}$, —O—$PO_3R^{m\ominus}$ and —$N(R^i)_3^+$, where $R^m$ and $R^i$ are independently selected from the group consisting of hydrogen, aliphatic substituents, aromatic substituents, reactive substituents, reactive aromatic substituents, and conjugated substances.

10. The rotaxane of claim 1, where the substituents of Z are selected so that the reporter molecule is electrically neutral, thereby increasing the hydrophobicity of the reporter.

11. The rotaxane of claim 1, where the reporter molecule is covalently or noncovalently associated with at least one of biological cells, DNA, lipids, nucleotides, polymers, proteins, and pharmacological agents.

12. The rotaxane of claim 1, further comprising a second reporter molecule selected from the group consisting of luminophores and chromophores.

13. The rotaxane of claim 12, where one of the reporter molecules is an energy transfer donor and the other is an energy transfer acceptor.

14. The rotaxane of claim 12, where the first and second reporter molecules are linked through a conjugated linkage that includes a carbon-carbon triple bond.

15. The rotaxane of claim 1, where the reporter molecule may be induced to luminesce by exposing the reporter molecule to one or more of electromagnetic energy, chemical energy, and electrochemical energy.

16. The rotaxane of claim 1, where Z is based on squaric acid.

17. The rotaxane of claim 1, where at least one of $W^3$ or $W^4$ contains an ionic group $R^{\pm}$.

18. The rotaxane of claim 1, where at least one of $W^3$ or $W^4$ contains an ionic group $R^{\pm}$ and at least one of $W^3$ or $W^4$ contains a reactive group $R^x$ or a conjugated substance $S_c$.

19. The rotaxane of claim 18, where the ionic group is selected from $-SO_3^{\ominus}$ and $-PO_3H^{\ominus}$.

20. The rotaxane of claim 1, where the macrocycle K has the structure $K^1$.

21. The rotaxane of claim 20, where the macrocycle includes a reactive group $R^x$, an ionic group $R^{\pm}$, or a conjugated substance $S_c$.

22. The rotaxane of claim 1, where Z includes at least one reactive group $L-R^x$, or at least one ionic group $L-R^{\pm}$, or at least one conjugated substance $L-S_c$.

23. The rotaxane of claim 1, having the formula

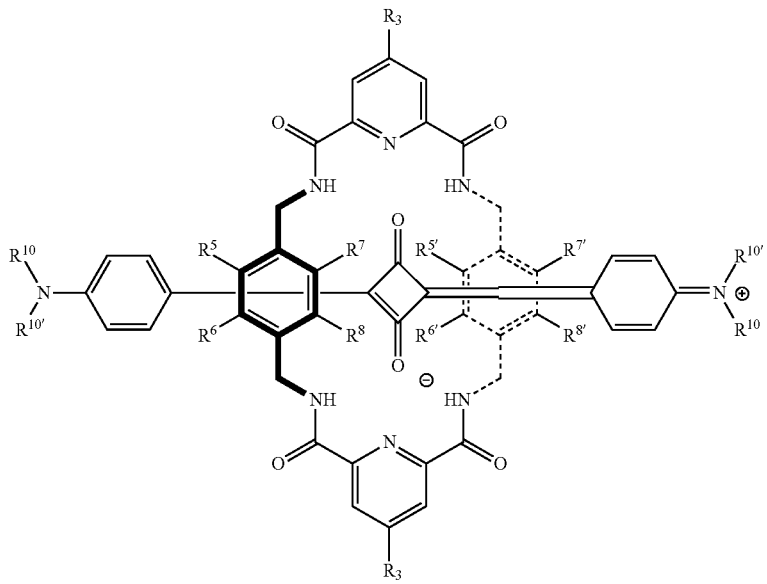

where $R^3$ is independently H, Cl, $OCH_3$, dialkylamino, morfolino, pipyridino, $-SO_2-(CH_2)_n-R^x$, $-SO_2-(CH_2)_n-R^{\pm}$, $-SO_2-(CH_2)_n-S_c$, $-S-(CH_2)_n-R^x$, $-S-(CH_2)_n-R^{\pm}$, $-S-(CH_2)_n-S_c$, $-L-R^{\pm}$, $-L-R^x$, $-L-S_c$ or $NO_2$;

n=1-6;

each $R^{10}$ and $R^{10'}$ is independently selected from H, $L-S_c$, $L-R^x$, $L-R^{\pm}$, $-CH_2-CONH-SO_2-Me$, aliphatic groups, alicyclic groups and aromatic groups;

L is alkyl having 1-20 carbons, and containing up to four amide linkages; and where $R^5$, $R^6$, $R^7$, $R^8$, $R^{5'}$, $R^{6'}$, $R^{7'}$ and $R^{8'}$ are methyl.

24. The rotaxane of claim 23 where at least one of $R^3$, $R^{10}$ or $R^{10'}$ includes a substituent $R^{\pm}$, a substituent $R^x$, or a carrier $S_c$.

25. The rotaxane of claim 24 wherein $R^{\pm}$ is selected from $-SO_3^{\ominus}$, $-PO_3^{2\ominus}$, $-O-PO_3^{2\ominus}$, $-PO_3R^{m\ominus}$, $-O-PO_3R^{m\ominus}$, where $R^m$ is selected from the group consisting of $L-S_c$, $L-R^x$, $L-R^{\pm}$, aliphatic substituents, and aromatic substituents.

26. A rotaxane having the formula

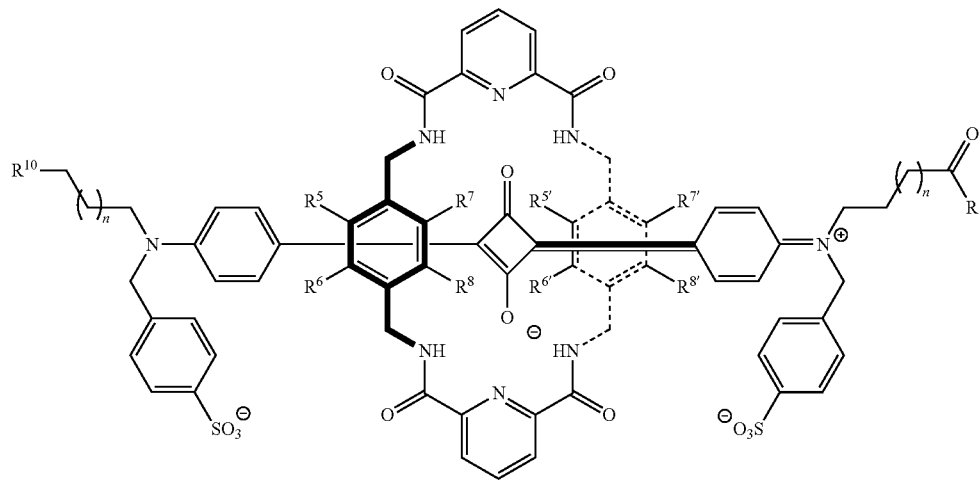

where R is selected from OH, NHS, NH—CH$_2$—CH$_2$-maleimide and S$_c$; and n is independently 0, 1, 2, or 3; R$^{10}$ is independently selected from H, COOH, SO$_3$H, CH$_2$—C$_6$H$_4$—SO$_3^\ominus$, CO—NHS, NH—CH$_2$—CH$_2$-maleimide or CONH—S$_c$;
and where R$^5$, R$^6$, R$^7$, R$^8$, R$^{5'}$, R$^{6'}$, R$^{7'}$ and R$^{8'}$ are methyl.

27. The rotaxane of claim 1, having the formula

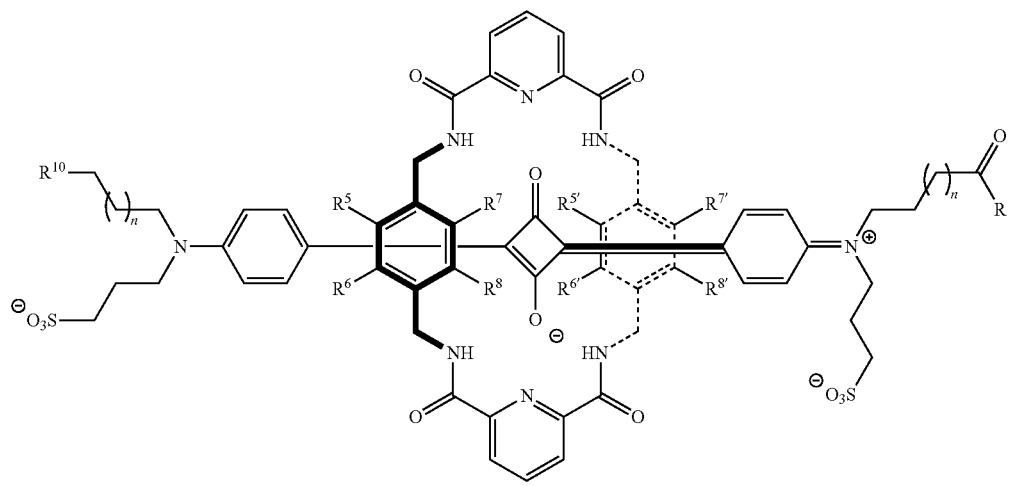

where R is OH, NHS, or NH—CH$_2$—CH$_2$-maleimide or NH—S$_c$; and n is independently 0, 1, 2 or 3;
R$^{10}$ is independently selected from H, COOH, SO$_3$H, CO—NHS, NH—CH$_2$—CH$_2$-maleimide or CONH—S$_c$;
and where R$^5$, R$^6$, R$^7$, R$^8$, R$^{5'}$, R$^{6'}$, R$^{7'}$ and R$^{8'}$ are methyl.

28. A method of performing a photoluminescence assay, the method comprising:
  selecting a photoluminescent rotaxane according to claim 1 that is covalently associated with a biological carrier molecule S$_c$;
  exciting the photoluminescent rotaxane conjugate; and
  detecting light emitted by the photoluminescent rotaxane.

29. The method of claim 28, where detecting light includes detecting emitted fluorescence.

30. The method of claim 28, where detecting light includes detecting emitted phosphorescence.

31. The method of claim 28, further comprising analyzing the emitted light and determining at least one of luminescence intensity, luminescence lifetime, and luminescence polarization.

32. The method of claim 28, further comprising associating the photoluminescent rotaxane with a second molecule.

33. A method of staining a biological sample, comprising:
  combining a solution of the rotaxane according to claim 1 with a biological sample in a concentration that is sufficient to yield a detectable optical response upon excitation.

34. The method of claim 33, where the biological sample includes biological cells.

35. The method of claim 33, where the rotaxane includes a conjugated substance S$_c$, and where the biological sample includes a member of a specific binding pair for which S$_c$ is a complementary member.

36. The method of claim 33 where the biological sample includes proteins, DNA, or oligonucleotides in a microarray.

37. A kit for fluorescent labeling of a biological or non-biological sample comprising
 a dye solution of the rotaxane of claim 1; and a buffer suitable for use with the biological or non-biological sample.

38. A method of diagnosing diseased tissue comprising administering the rotaxane of claim 1, exposing the diseased tissue to light in the visible and near infrared range and recording the emitted light produced from the rotaxane.

39. The rotaxane of claim 1, having the formula

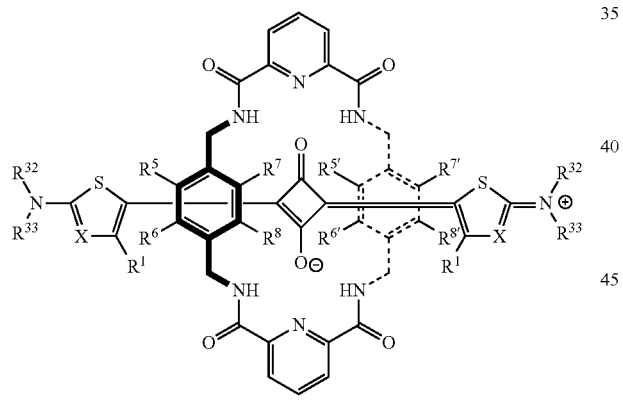

where $R^1$ is selected from H, methyl, t-butyl, and phenyl;
$R^{32}$ and $R^{33}$ are independently selected from H, L-$S_c$, L-$R^x$, L-$R^±$, —$CH_2$—CONH—$SO_2$-Me, aliphatic groups, alicyclic groups, alkylaryl groups, aromatic groups, benzyl, substituted benzyl, p-sulfo-benzyl, sulfo-butyl, sulfo-propyl, and sulfo-ethyl; or $R^{32}$ and $R^{33}$ combine to form heterocyclic rings that are optionally further substituted by L-$S_c$, L-$R^x$, L-$R^±$;
X is selected from CH and nitrogen;
L is alkyl having 1-20 carbons that includes up to 4 amide linkages;
$R^x$ is selected from COOH, NHS, maleimide, iodoacetamide; and phosphoramidite;
$R^±$ is selected from —$SO_3H$, —$PO_3^{2⊖}$, -and —O—$PO_3^{2⊖}$;
Sc is selected from peptides, proteins, nucleotides, oligonucleotides, phospholipids, amino acids, drugs and tyramide; and
where substituents $R^5$, $R^{5'}$, $R^6$, $R^{6'}$, $R^7$, $R^{7'}$, $R^8$ and $R^{8'}$ are methyl.

40. The rotaxane of claim 1, having the formula

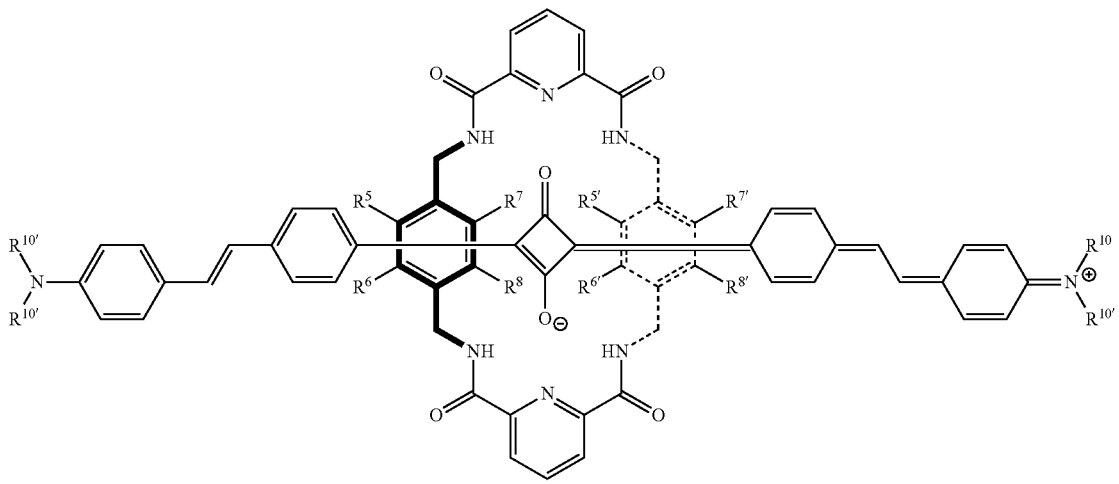

where $R^{10}$ and $R^{10'}$ are independently selected from H, L-$S_c$, L-$R^x$, L-$R^±$, —$CH_2$—CONH—$S0_2$-Me, aliphatic groups, alicyclic groups, alkylaryl groups, aromatic groups, benzyl, substituted benzyl, p-sulfo-benzyl, sulfo-butyl, sulfo-propyl, and sulfo-ethyl; or $R^{10}$ and $R^{10'}$ combine to form heterocyclic rings that are optionally further substituted by L-$S_c$, L-$R^x$, L-$R^±$;
L is alkyl having 1-20 carbons that includes up to 4 amide linkages;
$R^x$ is selected from COOH, NHS, maleimide, iodoacetamide, and phosphoramidite;
$R^±$ is selected from —$SO_3H$, —$PO_3^{2⊖}$, -and —O—$PO_3^{2⊖}$;
Sc is selected from peptides, proteins, nucleotides, oligonucleotides, phospholipids, amino acids, drugs and tyramide; and
where substituents $R^5$, $R^{5'}$, $R^6$, $R^{6'}$, $R^7$, $R^{7'}$, $R^8$ and $R^{8'}$ are methyl.

41. The rotaxane of claim 1, having the formula

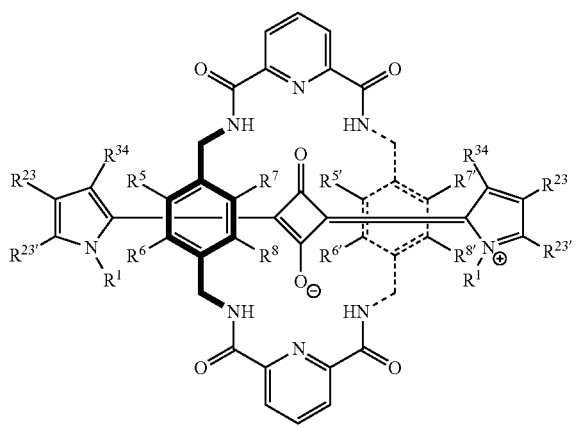

where $R^1$ is independently selected from H, $CH_3$, sulfo-propyl, sulfo-ethyl, —$(CH_2)_k$—$R^x$, —$(CH_2)_k$—$R^\pm$, or —$(CH_2)_k$—$S_c$; and k=2-5;

$R^{23}$ and $R^{23'}$ are independently H, alkyl, aryl, substituted aryl, carboxyl, —COOEt, sulfo-propyl, sulfo-ethyl, —$R^x$, —$R^\pm$, —$S_c$, —$(CH_2)_k$—$R^x$, —$(CH_2)_k$—$R^\pm$, or —$(CH_2)_k$—$S_c$;

$R^{34}$ is independently selected from H and methyl;

L is alkyl having 1-20 carbons that includes up to 4 amide linkages;

$R^x$ is selected from COOH, NHS, maleimide, iodoacetamide, and phosphoramidite;

$R^\pm$ is selected from —$SO_3H$, —$PO_3^{2\ominus}$, -and —O—$PO_3^{2\ominus}$;

Sc is selected from peptides, proteins, nucleotides, oligonucleotides, phospholipids, amino acids, drugs and tyramide; and where substituents $R^5$, $R^{5'}$, $R^6$, $R^{6'}$, $R^7$, $R^{7'}$, $R^8$ and $R^{8'}$ are methyl;

\* \* \* \* \*